(12) United States Patent
Chou et al.

(10) Patent No.: US 11,667,709 B2
(45) Date of Patent: Jun. 6, 2023

(54) ANTI-TIGIT ANTIBODIES AND METHODS OF USE

(71) Applicant: Industrial Technology Research Institute, Hsinchu (TW)

(72) Inventors: Min-Yuan Chou, Taipei (TW); Li-Tsen Lin, New Taipei (TW); Chung-Yuan Sun, Hsinchu County (TW); Ya-Ping Lai, Hsinchu (TW); Chin-Pen Lai, Hsinchu County (TW); Ssu-Yuan Wu, Hsinchu (TW); Mei-Wei Lin, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 268 days.

(21) Appl. No.: 16/948,563

(22) Filed: Sep. 23, 2020

(65) Prior Publication Data
US 2021/0087266 A1 Mar. 25, 2021

Related U.S. Application Data

(60) Provisional application No. 62/904,752, filed on Sep. 24, 2019.

(51) Int. Cl.
*C07K 16/28* (2006.01)
*A61P 35/00* (2006.01)
*A61K 45/06* (2006.01)

(52) U.S. Cl.
CPC .......... *C07K 16/2803* (2013.01); *A61P 35/00* (2018.01); *A61K 45/06* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| 9,334,331 | B2 * | 5/2016 | Igawa ..................... A61P 43/00 |
| 9,713,641 | B2 | 7/2017 | Hicklin et al. |
| 10,017,572 | B2 | 7/2018 | Grogan et al. |
| 10,047,158 | B2 | 8/2018 | Grogan et al. |
| 10,112,997 | B2 | 10/2018 | Gurney et al. |
| 10,189,902 | B2 | 1/2019 | Maurer et al. |

(Continued)

FOREIGN PATENT DOCUMENTS

| TW | 201915026 | 4/2019 |
| WO | WO 2009/126688 A2 | 10/2009 |

(Continued)

OTHER PUBLICATIONS

Hummer et al. Advances in computational structure-based antibody design Current Opinion in Structural Biology 2022, 74:102379 (Year: 2022).*

(Continued)

*Primary Examiner* — Scarlett Y Goon
*Assistant Examiner* — Miles Joseph Delahoussaye
(74) *Attorney, Agent, or Firm* — Finnegan, Henderson, Farabow, Garrett & Dunner, LLP

(57) ABSTRACT

Antibodies and antigen-binding fragments that bind to TIGIT are disclosed. The disclosure further relates to methods and compositions for use in treating an immune-related disease (e.g., a cancer or an infection or infectious disease) by administering a composition disclosed herein.

33 Claims, 27 Drawing Sheets

Specification includes a Sequence Listing.

(56) References Cited

U.S. PATENT DOCUMENTS

| | | |
|---|---|---|
| 10,213,505 B2 | 2/2019 | White et al. |
| 10,329,349 B2 | 6/2019 | Cooper et al. |
| 2018/0066055 A1 | 3/2018 | Williams et al. |
| 2021/0252059 A1* | 8/2021 | Pu .......................... C07K 14/57 |

FOREIGN PATENT DOCUMENTS

| | | |
|---|---|---|
| WO | WO 2014/089169 A2 | 6/2014 |
| WO | WO 2015/009856 A2 | 1/2015 |
| WO | WO 2016/028656 A1 | 2/2016 |
| WO | WO 2016/106302 A1 | 6/2016 |
| WO | WO 2018/102536 A1 | 6/2018 |
| WO | WO 2018/204363 A1 | 11/2018 |
| WO | WO 2019/023504 A1 | 1/2019 |
| WO | WO 2019/154415 A1 | 8/2019 |

OTHER PUBLICATIONS

Edwards et al. The Remarkable Flexibility of the Human Antibody Repertoire; Isolation of Over One Thousand Different Antibodies to a Single Protein, BLys. J. Mo/. Biol. (2003) 334, 103-118 (Year: 2003).*

Chauvin et al., (2015) "TIGIT and PD-1 impair tumor antigen-specific CD8+ T cells in melanoma patients", The Journal of Clinical Investigation, 125(5):2046-2058.

Fan et al., (2017) "De novo protein sequencing, humanization and in vitro effects of an antihuman CD34 mouse monoclonal antibody", Biochemistry and Biophysics Reports, 9:51-60.

Hung et al., (2018) "TIGIT and PD-1 dual checkpoint blockade enhances antitumor immunity and survival in GBM", Oncoimmunology, 7(8):e1466769 (13 pages).

Johnston et al., (2014) "The Immunoreceptor TIGIT Regulates Antitumor and Antiviral CD8+ T Cell Effector Function" Cancer Cell, 26:923-937.

Lazar et al., (2006) "Engineered antibody Fc variants with enhanced effector function", PNAS, 103(11):4005-4010.

Lozano et al., (2012) "The TIGIT/CD226 Axis Regulates Human T Cell Function", J. Immunol., 188:3869-3875.

Srivastava et al., (2017) "Anti-TIGIT induces T cell-mediated anti-tumor immune responses and combines with immune checkpoint inhibitors to enhance strong and long term anti-tumor immunity" OncoMed Pharmaceuticals, Inc., Redwood City, CA.

Stengel et al., (2012) "Structure of TIGIT immunoreceptor bound to poliovirus receptor reveals a cell-cell adhesion and signaling mechanism that requires cis-trans receptor clustering", PNAS, 109(14):5399-5404.

Yu et al., (2009) "The surface protein TIGIT suppresses T cell activation by promoting the generation of mature immunoregulatory dendritic cells", Nature Immunology, 10(1):48-57.

Chew et al., (2016) "TIGIT Marks Exhausted T Cells, Correlates with Disease Progression, and Serves as a Target for Immune Restoration in HIV and SIV Infection", Plos Pathogens, 12(1):e1005349 (28 pages).

European Application No. 20197922.6, filed Sep. 23, 2020, by Industrial Technology Research Institute: Extended European Search Report, dated Feb. 12, 2021 (12 pages).

Li et al., (2019) "Phage display screening of TIGIT-specific antibody for antitumor immunotherapy", Bioscience, Biotechnology, and Biochemistry, 83(9):1683-1696.

Liu et al., (2014) "In vitro and in vivo modifications of recombinant and human IgG antibodies", mAbs, 6(5):1145-1154.

* cited by examiner

SEQUENCE LISTING

```
<160> NUMBER OF SEQ ID NOS: 97

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Thr Phe Thr Asn Tyr Trp Ile Gly
1               5

<210> SEQ ID NO 2
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 2

Asp Ile Tyr Pro Gly Ser Ser Phe Thr Asn Ser Asn Glu Lys Phe Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gly Arg Gly Tyr Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Ser Ser Ser Val Ser Tyr Ile His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Thr Ser Asn Leu Ala Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Gln Trp Ser Arg Tyr Pro Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Thr Phe Thr Asp Ser Tyr Ile Asn
1               5
```

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Phe Tyr Pro Gly Ser Gly Asn Thr Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Ala Trp Leu Leu Phe Tyr Gly Met Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Asn Ser Ser Val Ser Tyr Met Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Thr Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr His Ser Tyr Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Thr Phe Thr Ser Tyr Trp Met His
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Ile Asp Pro Ser Asp Ser Ala Thr His
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Ile Asp Tyr Gly Ser Ser Tyr Phe Asp Tyr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Gln Ser Val Ser Thr Ser Ser Tyr Ser Tyr Ile His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ala Ser Asn Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln His Asn Trp Glu Ile Pro Arg Thr
1               5

<210> SEQ ID NO 19
<211> LENGTH: 10

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Met Val Gly Tyr Trp Tyr Phe Asp Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ile Val Gly Tyr Trp Tyr Phe Asp Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Arg Leu Gly Tyr Trp Tyr Phe Asp Val
1               5                   10

<210> SEQ ID NO 22
<211> LENGTH: 244
<212> TYPE: PRT
<213> ORGANISM: Homo sapiens

<400> SEQUENCE: 22

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Ala Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175
```

Gly Asp Leu Arg Arg Lys Ser Ala Gly Gln Glu Trp Ser Pro Ser
              180                 185                 190

Ala Pro Ser Pro Pro Gly Ser Cys Val Gln Ala Glu Ala Pro Ala
          195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Leu Phe Arg Ser Gly Ser Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Thr Phe Thr Val Ile Asn Leu
1               5

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Lys His Ser Gly Ala Glu Leu Val Arg Pro Gly Thr
1               5                   10                  15

Ser Val Lys Met Ser Cys Lys Ala Ser Gly Tyr Thr Phe Thr Asn Tyr
            20                  25                  30

Trp Ile Gly Trp Ala Lys Gln Arg Pro Gly His Gly Leu Glu Trp Ile
        35                  40                  45

Gly Asp Ile Tyr Pro Gly Ser Ser Phe Thr Asn Ser Asn Glu Lys Phe
    50                  55                  60

Lys Gly Lys Ala Thr Leu Thr Ala Asp Lys Ser Ser Ser Thr Ala Tyr
65                  70                  75                  80

Met Gln Phe Ser Ser Leu Thr Ser Glu Asp Ser Ala Ile Tyr Tyr Cys
                85                  90                  95

Ala Lys Leu Gly Arg Gly Tyr Trp Tyr Phe Asp Val Trp Gly Thr Gly
            100                 105                 110

Thr Ser Val Thr Val Ser Ala
        115

```
<210> SEQ ID NO 26
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Ile
            20                  25                  30

His Trp Tyr Gln Gln Lys Ser Gly Thr Ser Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Arg Tyr Pro Thr Phe
                85                  90                  95

Gly Gly Gly Thr Lys Leu Glu Ile Lys
            100                 105

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Ser
            20                  25                  30

Tyr Ile Asn Trp Val Lys Gln Arg Pro Gly Gln Gly Leu Glu Trp Ile
        35                  40                  45

Ala Arg Phe Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Ala Trp Leu Leu Phe Tyr Gly Met Asp Tyr Trp Gly Gln
            100                 105                 110

Gly Thr Thr Val Thr Val Ser Ser
        115                 120

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Leu Thr Gln Ser Pro Ala Ile Met Ser Ala Ser Pro Gly
1               5                   10                  15
```

Glu Lys Val Thr Ile Ser Cys Ser Ala Asn Ser Ser Val Ser Tyr Met
            20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
50                      55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys
            100                 105

<210> SEQ ID NO 29
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Ile Gln Gly Leu Glu Trp Ile
            35                  40                  45

Gly Asn Ile Asp Pro Ser Asp Ser Ala Thr His Tyr Asn Gln Lys Phe
        50                  55                  60

Lys Asp Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Thr Gly Ile Asp Tyr Gly Ser Ser Tyr Phe Asp Tyr Trp Gly
            100                 105                 110

Gln Gly Thr Ile Leu Thr Val Ser Ser
        115                 120

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Ile His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Asn Trp
            85                  90                  95

Glu Ile Pro Arg Thr Phe Gly Gly Gly Thr Lys Leu Glu Ile Lys
            100                 105                 110

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
                20                  25                  30

Trp Ile Gly Trp Val Arg Gln Thr Pro Gly Lys Gly Leu Glu Trp Val
            35                  40                  45

Gly Asp Ile Tyr Pro Gly Ser Ser Phe Thr Asn Ser Asn Glu Lys Phe
        50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Gly Arg Gly Tyr Trp Tyr Phe Asp Val Trp Gly Gln Gly
            100                 105                 110

Thr Leu Val Thr Val Ser Ser
        115

<210> SEQ ID NO 32
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Ser Val Ser Tyr Ile
                20                  25                  30

His Trp Tyr Gln Gln Lys Pro Gly Gln Ala Pro Lys Leu Leu Ile Tyr
            35                  40                  45

Thr Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys His Gln Trp Ser Arg Tyr Pro Thr Phe
                85                  90                  95

Gly Gly Gly Thr Lys Leu Glu Ile Lys
            100                 105

<210> SEQ ID NO 33
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 33

Asp Ile Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
        35                  40                  45

Gly Asp Ile Tyr Pro Gly Ser Ser Phe Thr Asn Ser Asn Glu Lys Phe
50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Met Val Gly Tyr Trp Tyr Phe Asp Val Trp Gly Gln Gly
            100                 105                 110

Thr Leu Val Thr Val Ser Ser
        115

<210> SEQ ID NO 34
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Ser Val Ser Tyr Ile
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys His Gln Trp Ser Arg Tyr Pro Thr Phe
                85                  90                  95

Gly Gly Gly Thr Lys Leu Glu Ile Lys
            100                 105

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30
```

Trp Ile Gly Trp Val Arg Gln Thr Pro Gly Lys Gly Leu Glu Trp Val
            35                  40                  45

Gly Asp Ile Tyr Pro Gly Ser Ser Phe Thr Asn Ser Asn Glu Lys Phe
        50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Ile Val Gly Tyr Trp Tyr Phe Asp Val Trp Gly Gln Gly
            100                 105                 110

Thr Leu Val Thr Val Ser Ser
        115

<210> SEQ ID NO 36
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys His Gln Trp Ser Arg Tyr Pro Thr Phe
                85                  90                  95

Gly Gly Gly Thr Lys Leu Glu Ile Lys
            100                 105

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
            35                  40                  45

Gly Asp Ile Tyr Pro Gly Ser Ser Phe Thr Asn Ser Asn Glu Lys Phe
        50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ile Arg Leu Gly Tyr Trp Tyr Phe Asp Val Trp Gly Gln Gly
            100                 105                 110

Thr Leu Val Thr Val Ser Ser
        115

<210> SEQ ID NO 38
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr
            35                  40                  45

Thr Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys His Gln Trp Ser Arg Tyr Pro Thr Phe
                85                  90                  95

Gly Gly Gly Thr Lys Leu Glu Ile Lys
            100                 105

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
            35                  40                  45

Gly Asp Ile Tyr Pro Gly Ser Ser Phe Thr Asn Ser Asn Glu Lys Phe
        50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Gly Arg Gly Tyr Trp Tyr Phe Asp Val Trp Gly Gln Gly
            100                 105                 110

Thr Leu Val Thr Val Ser Ser
        115

<210> SEQ ID NO 40
<211> LENGTH: 105
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 40

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys Gln Leu Phe Arg Ser Gly Ser Ala Phe
                85                  90                  95

Gly Gly Gly Thr Lys Leu Glu Ile Lys
            100                 105

<210> SEQ ID NO 41
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
        35                  40                  45

Gly Asp Ile Tyr Pro Gly Ser Ser Phe Thr Asn Ser Asn Glu Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Gly Arg Gly Tyr Trp Tyr Phe Asp Val Trp Gly Gln Gly
            100                 105                 110

Thr Leu Val Thr Val Ser Ser
        115

<210> SEQ ID NO 42
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr

```
                35                  40                  45
Thr Thr Ser Asn Leu Ala Ser Gly Val Pro Ser Arg Phe Ser Gly Ser
         50                  55                  60
Gly Ser Gly Thr Asp Phe Thr Leu Thr Ile Ser Ser Leu Glu Ala Glu
 65                  70                  75                  80
Asp Phe Ala Thr Tyr Tyr Cys Ser Thr Phe Thr Val Ile Asn Leu Phe
                 85                  90                  95
Gly Gly Gly Thr Lys Leu Glu Ile Lys
            100                 105

<210> SEQ ID NO 43
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 44
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 46
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
        35                  40                  45

Gly Asp Ile Tyr Pro Gly Ser Ser Phe Thr Asn Ser Asn Glu Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Gly Arg Gly Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 47
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
        35                  40                  45

Gly Asp Ile Tyr Pro Gly Ser Ser Phe Thr Asn Ser Asn Glu Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys

```
                85                  90                  95
Ala Arg Leu Gly Arg Gly Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 48
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

```
Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr
            35                  40                  45

Thr Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys Gln Leu Phe Arg Ser Gly Ser Ala Phe
                85                  90                  95

Gly Gly Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 49
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
            35                  40                  45

Gly Asp Ile Tyr Pro Gly Ser Ser Phe Thr Asn Ser Asn Glu Lys Phe
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Gly Arg Gly Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 50
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Gln Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Trp Ile Gly Trp Val Arg Gln Thr Pro Gly Lys Gly Leu Glu Trp Val
        35                  40                  45

Gly Asp Ile Tyr Pro Gly Ser Ser Phe Thr Asn Ser Asn Glu Lys Phe

```
            50                  55                  60
Lys Gly Arg Phe Thr Ile Ser Ala Asp Lys Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ala Arg Leu Gly Arg Gly Tyr Trp Tyr Phe Asp Val Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 51
<211> LENGTH: 212
<212> TYPE: PRT
<213> ORGANISM: Artificial Sequence
```

<220> FEATURE:
<223> OTHER INFORMATION: Description of Artificial Sequence: Synthetic
       polypeptide

<400> SEQUENCE: 51

Asp Ile Val Leu Thr Gln Ser Pro Ala Thr Leu Ser Ala Ser Leu Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Glu Ala Glu
65                  70                  75                  80

Asp Phe Ala Thr Tyr Tyr Cys Ser Thr Phe Thr Val Ile Asn Leu Phe
                85                  90                  95

Gly Gly Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 52
<211> LENGTH: 5
<212> TYPE: PRT
<213> ORGANISM: Homo sapiens

<400> SEQUENCE: 52

Tyr Phe Cys Ile Tyr
1               5

<210> SEQ ID NO 53
<211> LENGTH: 7
<212> TYPE: PRT
<213> ORGANISM: Homo sapiens

<400> SEQUENCE: 53

Gly Glu Tyr Phe Cys Ile Tyr
1               5

<210> SEQ ID NO 54
<211> LENGTH: 10
<212> TYPE: PRT
<213> ORGANISM: Homo sapiens

<400> SEQUENCE: 54

Asn Asp Thr Gly Glu Tyr Phe Cys Ile Tyr

<210> SEQ ID NO 55
<211> LENGTH: 13
<212> TYPE: PRT
<213> ORGANISM: Homo sapiens

<400> SEQUENCE: 55

Thr Val Asn Asp Thr Gly Glu Tyr Phe Cys Ile Tyr His
1               5                   10

<210> SEQ ID NO 56
<211> LENGTH: 7
<212> TYPE: PRT
<213> ORGANISM: Homo sapiens

<400> SEQUENCE: 56

Gly Ser Gly Ser Gly Ser Gly
1               5

<210> SEQ ID NO 57
<211> LENGTH: 7
<212> TYPE: PRT
<213> ORGANISM: Homo sapiens

<400> SEQUENCE: 57

Thr Ile Glu Thr Thr Gly Asn
1               5

<210> SEQ ID NO 58
<211> LENGTH: 7
<212> TYPE: PRT
<213> ORGANISM: Homo sapiens

<400> SEQUENCE: 58

Ala Glu Lys Gly Gly Ser Ile
1               5

<210> SEQ ID NO 59
<211> LENGTH: 7
<212> TYPE: PRT
<213> ORGANISM: Homo sapiens

<400> SEQUENCE: 59

Gln Cys His Leu Ser Ser Thr
1               5

<210> SEQ ID NO 60
<211> LENGTH: 7
<212> TYPE: PRT
<213> ORGANISM: Homo sapiens

<400> SEQUENCE: 60

Gln Val Thr Gln Val Asn Trp
1               5

<210> SEQ ID NO 61
<211> LENGTH: 7
<212> TYPE: PRT
<213> ORGANISM: Homo sapiens

<400> SEQUENCE: 61

Gln Asp Gln Leu Leu Ala Ile
1               5

```
<210> SEQ ID NO 62
<211> LENGTH: 7
<212> TYPE: PRT
<213> ORGANISM: Homo sapiens

<400> SEQUENCE: 62

Ala Asp Leu Gly Trp His Ile
1               5

<210> SEQ ID NO 63
<211> LENGTH: 7
<212> TYPE: PRT
<213> ORGANISM: Homo sapiens

<400> SEQUENCE: 63

Ser Phe Lys Asp Arg Val Ala
1               5

<210> SEQ ID NO 64
<211> LENGTH: 7
<212> TYPE: PRT
<213> ORGANISM: Homo sapiens

<400> SEQUENCE: 64

Pro Gly Leu Gly Leu Thr Leu
1               5

<210> SEQ ID NO 65
<211> LENGTH: 7
<212> TYPE: PRT
<213> ORGANISM: Homo sapiens

<400> SEQUENCE: 65

Leu Thr Val Asn Asp Thr Gly
1               5

<210> SEQ ID NO 66
<211> LENGTH: 7
<212> TYPE: PRT
<213> ORGANISM: Homo sapiens

<400> SEQUENCE: 66

Phe Cys Ile Tyr His Thr Tyr
1               5

<210> SEQ ID NO 67
<211> LENGTH: 7
<212> TYPE: PRT
<213> ORGANISM: Homo sapiens

<400> SEQUENCE: 67

Gly Thr Tyr Thr Gly Arg Ile
1               5

<210> SEQ ID NO 68
<211> LENGTH: 7
<212> TYPE: PRT
<213> ORGANISM: Homo sapiens

<400> SEQUENCE: 68

Glu Val Leu Glu Ser Ser Val
1               5

<210> SEQ ID NO 69
```

```
<211> LENGTH: 7
<212> TYPE: PRT
<213> ORGANISM: Homo sapiens

<400> SEQUENCE: 69

His Gly Ala Arg Phe Gly Ser
1               5

<210> SEQ ID NO 70
<211> LENGTH: 10
<212> TYPE: PRT
<213> ORGANISM: Homo sapiens

<400> SEQUENCE: 70

Ser Gly Ser Gly Thr Gly Thr Ile Glu Thr
1               5                   10

<210> SEQ ID NO 71
<211> LENGTH: 10
<212> TYPE: PRT
<213> ORGANISM: Homo sapiens

<400> SEQUENCE: 71

Thr Thr Gly Asn Ile Ser Ala Glu Lys Gly
1               5                   10

<210> SEQ ID NO 72
<211> LENGTH: 10
<212> TYPE: PRT
<213> ORGANISM: Homo sapiens

<400> SEQUENCE: 72

Gly Gly Ser Ile Ile Leu Gln Cys His Leu
1               5                   10

<210> SEQ ID NO 73
<211> LENGTH: 10
<212> TYPE: PRT
<213> ORGANISM: Homo sapiens

<400> SEQUENCE: 73

Leu Ser Ser Thr Thr Ala Gln Val Thr Gln
1               5                   10

<210> SEQ ID NO 74
<211> LENGTH: 10
<212> TYPE: PRT
<213> ORGANISM: Homo sapiens

<400> SEQUENCE: 74

Gln Val Asn Trp Glu Gln Gln Asp Gln Leu
1               5                   10

<210> SEQ ID NO 75
<211> LENGTH: 10
<212> TYPE: PRT
<213> ORGANISM: Homo sapiens

<400> SEQUENCE: 75

Leu Leu Ala Ile Cys Asn Ala Asp Leu Gly
1               5                   10

<210> SEQ ID NO 76
<211> LENGTH: 10
<212> TYPE: PRT
```

<213> ORGANISM: Homo sapiens

<400> SEQUENCE: 76

Gly Trp His Ile Ser Pro Ser Phe Lys Asp
1               5                   10

<210> SEQ ID NO 77
<211> LENGTH: 10
<212> TYPE: PRT
<213> ORGANISM: Homo sapiens

<400> SEQUENCE: 77

Asp Arg Val Ala Pro Gly Pro Gly Leu Gly
1               5                   10

<210> SEQ ID NO 78
<211> LENGTH: 10
<212> TYPE: PRT
<213> ORGANISM: Homo sapiens

<400> SEQUENCE: 78

Gly Leu Thr Leu Gln Ser Leu Thr Val Asn
1               5                   10

<210> SEQ ID NO 79
<211> LENGTH: 10
<212> TYPE: PRT
<213> ORGANISM: Homo sapiens

<400> SEQUENCE: 79

Tyr His Thr Tyr Pro Asp Gly Thr Tyr Thr
1               5                   10

<210> SEQ ID NO 80
<211> LENGTH: 10
<212> TYPE: PRT
<213> ORGANISM: Homo sapiens

<400> SEQUENCE: 80

Thr Gly Arg Ile Phe Leu Glu Val Leu Glu
1               5                   10

<210> SEQ ID NO 81
<211> LENGTH: 10
<212> TYPE: PRT
<213> ORGANISM: Homo sapiens

<400> SEQUENCE: 81

Glu Ser Ser Val Ala Glu His Gly Ala Arg
1               5                   10

<210> SEQ ID NO 82
<211> LENGTH: 13
<212> TYPE: PRT
<213> ORGANISM: Homo sapiens

<400> SEQUENCE: 82

Gly Ser Gly Ser Gly Ser Gly Thr Gly Thr Ile Glu Thr
1               5                   10

<210> SEQ ID NO 83
<211> LENGTH: 13
<212> TYPE: PRT
<213> ORGANISM: Homo sapiens

```
<400> SEQUENCE: 83

Thr Ile Glu Thr Thr Gly Asn Ile Ser Ala Glu Lys Gly
1               5                   10

<210> SEQ ID NO 84
<211> LENGTH: 13
<212> TYPE: PRT
<213> ORGANISM: Homo sapiens

<400> SEQUENCE: 84

Ala Glu Lys Gly Gly Ser Ile Ile Leu Gln Cys His Leu
1               5                   10

<210> SEQ ID NO 85
<211> LENGTH: 13
<212> TYPE: PRT
<213> ORGANISM: Homo sapiens

<400> SEQUENCE: 85

Gln Cys His Leu Ser Ser Thr Thr Ala Gln Val Thr Gln
1               5                   10

<210> SEQ ID NO 86
<211> LENGTH: 13
<212> TYPE: PRT
<213> ORGANISM: Homo sapiens

<400> SEQUENCE: 86

Gln Val Thr Gln Val Asn Trp Glu Gln Gln Asp Gln Leu
1               5                   10

<210> SEQ ID NO 87
<211> LENGTH: 13
<212> TYPE: PRT
<213> ORGANISM: Homo sapiens

<400> SEQUENCE: 87

Gln Asp Gln Leu Leu Ala Ile Cys Asn Ala Asp Leu Gly
1               5                   10

<210> SEQ ID NO 88
<211> LENGTH: 13
<212> TYPE: PRT
<213> ORGANISM: Homo sapiens

<400> SEQUENCE: 88

Ala Asp Leu Gly Trp His Ile Ser Pro Ser Phe Lys Asp
1               5                   10

<210> SEQ ID NO 89
<211> LENGTH: 13
<212> TYPE: PRT
<213> ORGANISM: Homo sapiens

<400> SEQUENCE: 89

Ser Phe Lys Asp Arg Val Ala Pro Gly Pro Gly Leu Gly
1               5                   10

<210> SEQ ID NO 90
<211> LENGTH: 13
<212> TYPE: PRT
<213> ORGANISM: Homo sapiens

<400> SEQUENCE: 90
```

```
Pro Gly Leu Gly Leu Thr Leu Gln Ser Leu Thr Val Asn
1               5                   10
```

<210> SEQ ID NO 91
<211> LENGTH: 13
<212> TYPE: PRT
<213> ORGANISM: Homo sapiens

<400> SEQUENCE: 91

```
Leu Thr Val Asn Asp Thr Gly Glu Tyr Phe Cys Ile Tyr
1               5                   10
```

<210> SEQ ID NO 92
<211> LENGTH: 13
<212> TYPE: PRT
<213> ORGANISM: Homo sapiens

<400> SEQUENCE: 92

```
Phe Cys Ile Tyr His Thr Tyr Pro Asp Gly Thr Tyr Thr
1               5                   10
```

<210> SEQ ID NO 93
<211> LENGTH: 13
<212> TYPE: PRT
<213> ORGANISM: Homo sapiens

<400> SEQUENCE: 93

```
Gly Thr Tyr Thr Gly Arg Ile Phe Leu Glu Val Leu Glu
1               5                   10
```

<210> SEQ ID NO 94
<211> LENGTH: 13
<212> TYPE: PRT
<213> ORGANISM: Homo sapiens

<400> SEQUENCE: 94

```
Glu Val Leu Glu Ser Ser Val Ala Glu His Gly Ala Arg
1               5                   10
```

<210> SEQ ID NO 95
<211> LENGTH: 140
<212> TYPE: PRT
<213> ORGANISM: Homo sapiens

<400> SEQUENCE: 95

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125
```

```
Ser Ser Val Ala Glu His Gly Ala Arg Phe Gln Ile
    130                 135                 140

<210> SEQ ID NO 96
<211> LENGTH: 141
<212> TYPE: PRT
<213> ORGANISM: Macaca fascicularis

<400> SEQUENCE: 96

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile
    130                 135                 140

<210> SEQ ID NO 97
<211> LENGTH: 138
<212> TYPE: PRT
<213> ORGANISM: Mus sp.

<400> SEQUENCE: 97

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala
    130                 135
```

ANTI-TIGIT ANTIBODIES AND METHODS OF USE

The present disclosure claims the benefit of priority to U.S. Provisional Patent Application No. 62/904,752, filed Sep. 24, 2019, which is incorporated herein by reference in its entirety.

The instant application contains a Sequence Listing which has been submitted electronically in ASCII format and is hereby incorporated by reference in its entirety. Said ASCII copy, created on Sep. 23, 2020, is named 09708_0019-00000_SL.txt and is 64,693 bytes in size.

The present disclosure relates to antibodies and antigen-binding fragments thereof that bind to T cell immunoglobulin and ITIM domain (TIGIT). The disclosure further relates to methods and compositions for using the anti-TIGIT antibodies and antigen-binding fragments disclosed herein, e.g., in treating an immune-related disease (e.g., a cancer or an infection or infectious disease). Methods and compositions for screening and producing the disclosed anti-TIGIT antibodies and antigen-binding fragments are also provided.

In the context of chronic antigen exposure, such as in cancer or viral infections, T cells can become exhausted/dysfunctional. Exhausted T cells can exhibit defective proliferative capacities and cytokine production. Exhausted T cells can also upregulate inhibitory receptors/immune checkpoints that bind to ligands expressed by tumor cells and by antigen-presenting cells (APCs) (Zarour (2016) Clin Cancer Res. 22(8):1856-64).

TIGIT, an immune checkpoint protein, is a member of the immunoglobulin superfamily and is composed of multiple domains, including an extracellular IgV domain, a type I transmembrane region, and a cytoplasmic tail. The tail consists of an immunoreceptor tyrosine-based inhibitory motif (ITIM), and an immunoglobulin tail tyrosine (ITT)-like motif, both of which are involved in the post-translational modification and the ensuing regulation of TIGIT activation (Manieri et al. (2017) Trends Immunol. 38(1):20-8).

TIGIT acts as a coinhibitory receptor and is expressed on natural killer (NK) cells and T cells, which can interact with APCs through different proteins. TIGIT binds with high affinity to CD155 (PVR) and weakly interacts with CD112 (PVRL2, nectin-2) (Levin et al. (2011) Eur J Immunol. 41(4):902-15; Stanietsky et al. (2009) Proc Natl Acad Sci USA. 106(42):17858-63; Yu et al. (2009) Nat Immunol. 10(1):48-57). Both of these ligands are expressed on APCs as well as on a variety of non-hematopoietic cell types (including tumor cells) and are shared with CD226 (Bottino et al. (2003) J Exp Med. 198(4):557-67; Casado et al. (2009) Cancer Immunol Immunother. 58(9):1517-26; Mendelsohn et al. (1989) Cell. 56(5):855-65). CD226, a costimulatory receptor, binds the two ligands with about 10 times lower affinity than TIGIT, which can inhibit the interaction between CD226 and CD155 in a dose-dependent manner (Lozano et al. (2012) J Immunol. doi: 10.4049/jimmunol.1103627). In addition to ligand competition, TIGIT can also directly bind to CD226 in cis and disrupt its homodimerization and its costimulatory function (Johnston et al. (2014) Cancer Cell. 26(6):923-37).

In effector T cells, TIGIT can act as a cell intrinsic inhibitor, e.g., by dampening effector cell activation, inhibiting proliferation and thereby limiting the effector cell pool, and/or by reducing effector cell function and cytokine production (Joller and Kuchroo (2017) Curr Top Microbiol Immunol. 410:127-56). TIGIT is also highly expressed on regulatory T cells (Tregs), where it promotes their suppressive function. TIGIT$^+$ Tregs express higher levels of Treg signature genes, such as Foxp3, CD25, and CTLA-4 and show enhanced demethylation in Treg-specific demethylated regions (TSDR), leading to higher lineage stability (Joller et al. (2014) Immunity 40(4):569-81; Fuhrman et al. (2015) J Immunol. 195(1):145-55). Thus, in regulatory cells, TIGIT can contribute to lineage stability and enhance their inhibitory function through the direct induction of suppressive mediators. TIGIT's functions in effector and regulatory cells, particularly those which may restrict the ability of immune cells to mount effective responses against tumors and persistent pathogens, make it an attractive immunotherapy target.

Agents capable of targeting TIGIT have been described (Johnston et al. (2014) Cancer Cell. 26(6):923-37; Chauvin et al. (2015) J Clin Invest. 125(5):2046-58; Srivastava et al. (2017) In: Proceedings of the AACR Annual Meeting; Cancer Res. 77(13 Suppl):Abstract 2612; Hung et al. (2018) Oncoimmunology 7(8):e1466769; see also ClinicalTrials.gov, e.g., NCT04256421, NCT04165070, NCT02913313, NCT04262856). However, these agents have shown limited therapeutic utility in the clinic, particularly when used as monotherapies (see, e.g., Johnston et al. (2014) Cancer Cell. 26(6):923-37). Thus, there remains a need for TIGIT-targeting agents that can modulate its function and overcome the limitations of current treatment options.

In some embodiments, the present disclosure provides, in part, novel antibodies and antigen-binding fragments that bind, e.g., specifically bind, to TIGIT. These may be administered as single agents or as part of combination therapies.

In some embodiments, the antibodies and antigen-binding fragments disclosed herein specifically bind to TIGIT. In some embodiments, the antibodies and antigen-binding fragments disclosed herein are capable of reducing or blocking the interaction of TIGIT and CD155. In some embodiments, the antibodies and antigen-binding fragments disclosed herein possess one or more superior properties as compared to a reference anti-TIGIT antibody or antigen-binding fragment. In some embodiments, these properties are desirable for a therapeutic antibody and may include one or more of: high binding affinity to human TIGIT; cross-reactivity between human TIGIT, cynomolgus monkey (cyno) TIGIT, and/or mouse TIGIT; effective T cell activation activity; effective in vivo anti-cancer activity; and/or potent antibody-dependent cell-mediated cytotoxicity (e.g., against regulatory T cells), e.g., as compared to a reference anti-TIGIT antibody or antigen-binding fragment. By virtue of some or all of these improved properties, the anti-TIGIT antibodies and antigen-binding fragments disclosed herein may be useful for treating human patients suffering from an immune-related disease (e.g., a cancer or an infection or infectious disease).

In some embodiments, the present disclosure provides an isolated antibody or antigen-binding fragment that specifically binds to TIGIT, wherein the antibody or antigen-binding fragment comprises:

(a) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3);

(b) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 24 (LCDR3);

(c) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);

(d) three heavy chain complementarity determining regions (HCDRs) comprising amino acid sequences of SEQ ID NO: 1 (HCDR1), SEQ ID NO: 2 (HCDR2), and SEQ ID NO: 19 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);

(e) three heavy chain complementarity determining regions (HCDRs) comprising amino acid sequences of SEQ ID NO: 1 (HCDR1), SEQ ID NO: 2 (HCDR2), and SEQ ID NO: 20 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);

(f) three heavy chain complementarity determining regions (HCDRs) comprising amino acid sequences of SEQ ID NO: 1 (HCDR1), SEQ ID NO: 2 (HCDR2), and SEQ ID NO: 21 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);

(g) three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3); or (h) three heavy chain complementarity determining regions (HCDRs) comprising amino acid sequences of SEQ ID NO: 13 (HCDR1), SEQ ID NO: 14 (HCDR2), and SEQ ID NO: 15 (HCDR3); and three light chain complementarity determining regions (LCDRs) comprising amino acid sequences of SEQ ID NO: 16 (LCDR1), SEQ ID NO: 17 (LCDR2), and SEQ ID NO: 18 (LCDR3).

In some embodiments, the antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the antibody or antigen-binding fragment comprises human germline heavy and light chain framework regions, or human germline heavy and light chain framework regions mutated to comprise one or more amino acid substitutions. In some embodiments, the antibody or antigen-binding fragment comprises a heavy chain variable region that is at least 90% identical to an amino acid sequence of SEQ ID NO: 39, and a light chain variable region that is at least 90% identical to an amino acid sequence of SEQ ID NO: 40. In some embodiments, the antibody or antigen-binding fragment comprises a heavy chain variable region comprising an amino acid sequence of SEQ ID NO: 39, and a light chain variable region comprising an amino acid sequence of SEQ ID NO: 40.

In some embodiments, the antibody or antigen-binding fragment comprises a human IgG1 heavy chain constant region, or a human IgG1 heavy chain constant region mutated to modify effector function. In some embodiments, the antibody or antigen-binding fragment comprises a heavy chain constant region comprising an amino acid sequence of SEQ ID NO: 43. In some embodiments, the antibody or antigen-binding fragment comprises a heavy chain constant region comprising an amino acid sequence of SEQ ID NO: 43 mutated to comprise amino acid substitutions at positions 239, 330, and 332. In some embodiments, the S at position 239 of SEQ ID NO: 43 is substituted with D; the A at position 330 of SEQ ID NO: 43 is substituted with L; and the I at position 332 of SEQ ID NO: 43 is substituted with E. In some embodiments, the antibody or antigen-binding fragment comprises a heavy chain constant region comprising an amino acid sequence of SEQ ID NO: 44. In some embodiments, the heavy chain constant region further comprises a C-terminal lysine (K).

In some embodiments, the antibody or antigen-binding fragment comprises a human Ig kappa light chain constant region. In some embodiments, the antibody or antigen-binding fragment comprises a light chain constant region comprising an amino acid sequence of SEQ ID NO: 45.

In some embodiments, the antibody or antigen-binding fragment comprises:

(a) a heavy chain constant region comprising an amino acid sequence of SEQ ID NO: 43, and a light chain constant region comprising an amino acid sequence of SEQ ID NO: 45; or (b) a heavy chain constant region comprising an amino acid sequence of SEQ ID NO: 44, and a light chain constant region comprising an amino acid sequence of SEQ ID NO: 45.

In some embodiments, the antibody or antigen-binding fragment comprises:

(a) a heavy chain comprising an amino acid sequence of SEQ ID NO: 46, and a light chain comprising an amino acid sequence of SEQ ID NO: 48; or (b) a heavy chain comprising an amino acid sequence of SEQ ID NO: 47, and a light chain comprising an amino acid sequence of SEQ ID NO: 48.

In some embodiments, the antibody or antigen-binding fragment comprises a heavy chain constant region comprising an amino acid sequence of SEQ ID NO: 44, and a light chain constant region comprising an amino acid sequence of SEQ ID NO: 45. In some embodiments, the antibody or antigen-binding fragment comprises a heavy chain comprising an amino acid sequence of SEQ ID NO: 47, and a light chain comprising an amino acid sequence of SEQ ID NO: 48. In some embodiments, the heavy chain constant region or heavy chain further comprises a C-terminal lysine (K).

In some embodiments, the present disclosure provides an isolated antibody or antigen-binding fragment that specifically binds to human TIGIT, wherein the antibody or antigen-binding fragment binds to a region of human TIGIT comprising the Y at position 106 of SEQ ID NO: 22. In some embodiments, the region further comprises one or more of: the Q at position 56 of SEQ ID NO: 22; the G at position 74 of SEQ ID NO: 22; the Y at position 110 of SEQ ID NO: 22; and the H at position 111 of SEQ ID NO: 22. In some embodiments, the region comprises at least the Q at position 56 of SEQ ID NO: 22; and the Y at position 106 of SEQ ID NO: 22. In some embodiments, the region comprises at least: the Q at position 56 of SEQ ID NO: 22; the G at position 74 of SEQ ID NO: 22; the Y at position 106 of SEQ ID NO: 22; and the Y at position 110 of SEQ ID NO: 22. In some embodiments, the region is non-linear.

In some embodiments, the antibody or antigen-binding fragment competes for binding to human TIGIT with a reference antibody or antigen-binding fragment, wherein the reference antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the antibody or antigen-binding fragment binds to the same region of human TIGIT as a reference antibody or antigen-binding fragment, wherein the reference antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the reference antibody or antigen-binding fragment comprises human germline heavy and light chain framework regions, or human germline heavy and light chain framework regions mutated to comprise one or more amino acid substitutions. In some embodiments, the reference antibody or antigen-binding fragment comprises a heavy chain variable region comprising an amino acid sequence of SEQ ID NO: 39, and a light chain variable region comprising an amino acid sequence of SEQ ID NO: 40. In some embodiments, the reference antibody or antigen-binding fragment comprises a heavy chain constant region comprising an amino acid sequence of SEQ ID NO: 44, and a light chain constant region comprising an amino acid sequence of SEQ ID NO: 45. In some embodiments, the reference antibody or antigen-binding fragment comprises a heavy chain comprising an amino acid sequence of SEQ ID NO: 47, and a light chain comprising an amino acid sequence of SEQ ID NO: 48. In some embodiments, the heavy chain constant region or heavy chain further comprises a C-terminal lysine (K).

In some embodiments, the present disclosure provides pharmaceutical compositions comprising the described antibodies and/or antigen-binding fragments. In some embodiments, a pharmaceutical composition comprises one or more antibodies and/or one or more antigen-binding fragments, along with at least a pharmaceutically acceptable carrier.

Also provided herein, in some embodiments, are therapeutic methods and uses for the described antibodies and/or antigen-binding fragments, e.g., in activating and/or killing one or more immune cells.

In some embodiments, the present disclosure provides a method of activating and/or killing one or more immune cells in a subject in need thereof, comprising administering to the subject an effective amount of an antibody or antigen-binding fragment described herein, or a pharmaceutical composition described herein. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides an antibody or antigen-binding fragment described herein, or a pharmaceutical composition described herein, for use in activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein, or a pharmaceutical composition described herein, for activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein in the manufacture of a medicament for activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, provided herein are therapeutic methods and uses for the described antibodies and/or antigen-binding fragments, e.g., in treating a cancer.

In some embodiments, the present disclosure provides a method of treating a cancer in a subject in need thereof, comprising administering to the subject a therapeutically effective amount of an antibody or antigen-binding fragment described herein, or a pharmaceutical composition described herein. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides an antibody or antigen-binding fragment described herein, or a pharmaceutical composition described herein, for use in treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein, or a pharmaceutical composition described herein, for treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein in the manufacture of a medicament for treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, provided herein are therapeutic methods and uses for the described antibodies and/or antigen-binding fragments, e.g., in treating an infection or infectious disease.

In some embodiments, the present disclosure provides a method of treating an infection or infectious disease in a subject in need thereof, comprising administering to the subject a therapeutically effective amount of an antibody or antigen-binding fragment described herein, or a pharmaceutical composition described herein. In some embodiments, the infection or infectious disease is a human T cell leukemia virus type 1-associated disease. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides an antibody or antigen-binding fragment described herein, or a pharmaceutical composition described herein, for use in treating an infection or infectious disease in a subject in need thereof. In some embodiments, the infection or infectious disease is a human T cell leukemia virus type 1-associated disease. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein, or a pharmaceutical composition described herein, for treating an infection or infectious disease in a subject in need thereof. In some embodiments, the infection or infectious disease is a human T cell leukemia virus type 1-associated disease. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, the present disclosure provides a use of an antibody or antigen-binding fragment described herein in the manufacture of a medicament for treating an infection or infectious disease in a subject in need thereof. In some embodiments, the infection or infectious disease is a human T cell leukemia virus type 1-associated disease. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody (e.g., pembrolizumab).

In some embodiments, nucleic acid(s) encoding an antibody or antigen-binding fragment of the disclosure also provided. The nucleic acids may be in the form of an isolated nucleic acid and/or a nucleic acid incorporated into an isolated vector.

In still other embodiments, the present disclosure provides methods of producing the described antibodies and/or antigen-binding fragments. In some embodiments, the present disclosure provides a method of producing an antibody or antigen-binding fragment, comprising culturing a host cell or cell population modified to comprise one or more nucleic acids encoding an antibody or antigen-binding fragment under conditions suitable to produce the antibody or antigen-binding fragment. In some embodiments, the method further comprises isolating, purifying, and/or recovering the produced antibody or antigen-binding fragment.

BRIEF DESCRIPTION OF THE DRAWINGS

FIG. 9A shows human regulatory T cell-like phenotypic markers (CD3+CD4+ CD25$^{high}$CD127$^{low}$FoxP+) expressed by MJ[G11] cells. MJ[G11] cells were stained with fluorescent dye-conjugated anti-human antibodies, including anti-CD4-Per-CP, anti-CD25-APC, anti-CD127-PE, and anti-FoxP3-Alexa 488. FoxP3 stained intracellularly, whereas the other antibodies stained the cell surface. FIG. 9B shows a flow cytometry plot showing constitutive expression of human TIGIT by MJ[G11] cells. Cells were stained with anti-TIGIT antibody, MBSA43, conjugated with PE fluorescent dye.

FIG. 15A shows a dot blot analysis of different antibodies against denatured (DeNat) and native (Nat) forms of human TIGIT protein. FIG. 15B shows a graph of microarray analyses showing conformational epitope mapping of the 7D4 antibody binding to human TIGIT peptide loops comprising 7-, 10-, and 13-amino acid residues. The conserved 7D4 binding peptide loop, with amino acid residue Y106 in the consensus motif of YFCIY (SEQ ID NO: 52), is identified. FIG. 15B discloses SEQ ID NOs. 53-78, 54, 79-94, respectively, in order of appearance.

FIG. 16 discloses SEQ ID NOs. 95-97, respectively, in order of appearance.

DETAILED DESCRIPTION

Figure 1:
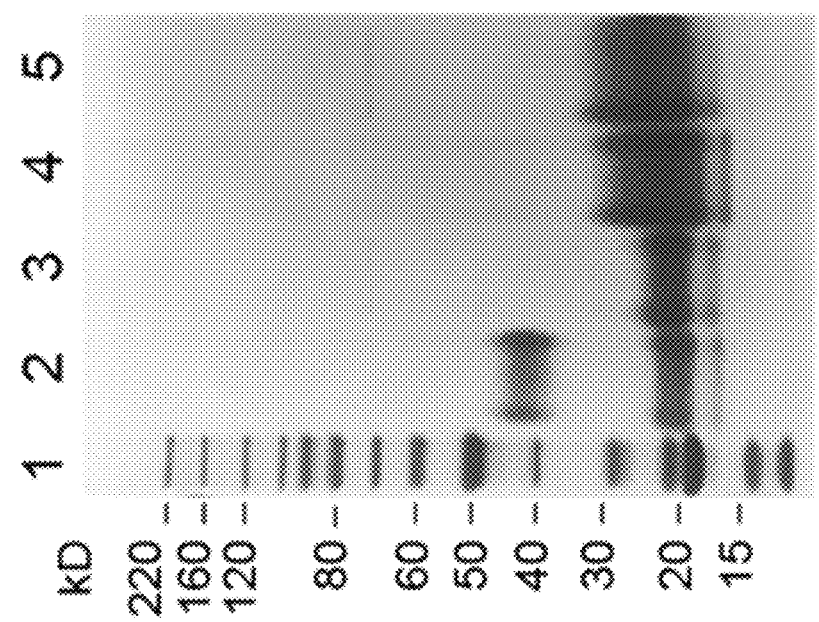
FIG. 1 shows an SDS-PAGE gel showing the purities of recombinant human and mouse TIGIT IgV domains expressed in NS0 cells. Proteins from culture media were individually purified by Strep-Tactin XT Superflow columns prior to SDS-PAGE analysis. Lane 1: Bench Mark; Lane 2: human TIGIT, 3 μg (non-reduced); Lane 3: human TIGIT, 3 μg (reduced); Lane 4: mouse TIGIT, 3 μg (non-reduced; Lane 5: mouse TIGIT, 3 μg (reduced).
Figure 2B:
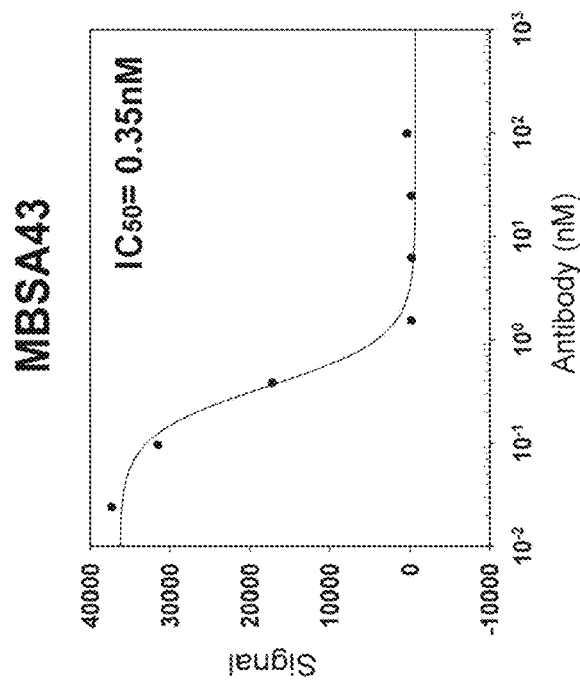
FIG. 2A-2E show graphs showing the inhibition of human TIGIT binding to human CD155 by different anti-TIGIT antibodies, including reference antibodies 15A6 (FIG. 2A) and MBSA43 (FIG. 2B), and antibodies 7D4 (FIG. 2C), 2C9 (FIG. 2D), and 3A9 (FIG. 2E). Assays were performed by AlphaLISA using a TIGIT:CD155 homogeneous assay. The half maximal inhibitory concentration ($IC_{50}$) of each antibody is indicated.
Figure 2A:
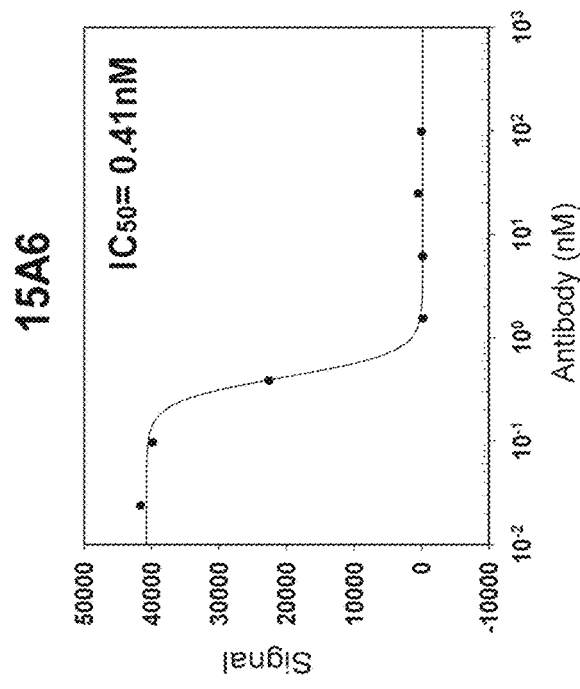
Figure 2D:
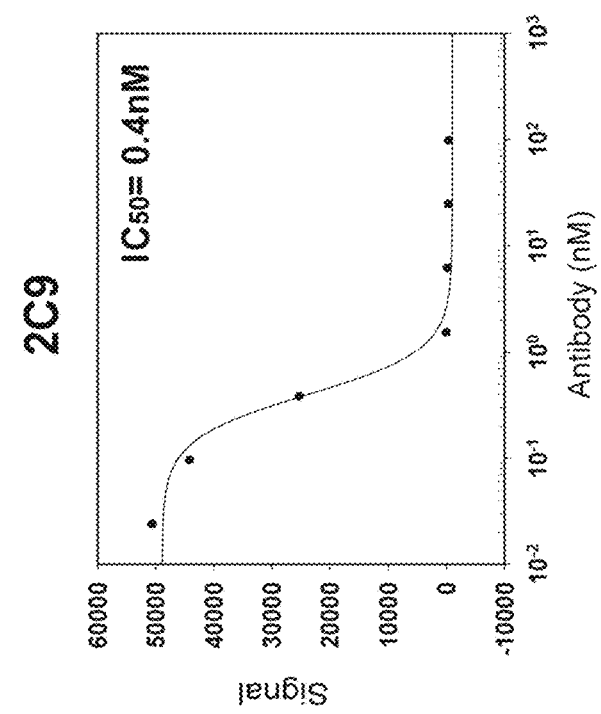
Figure 2C:
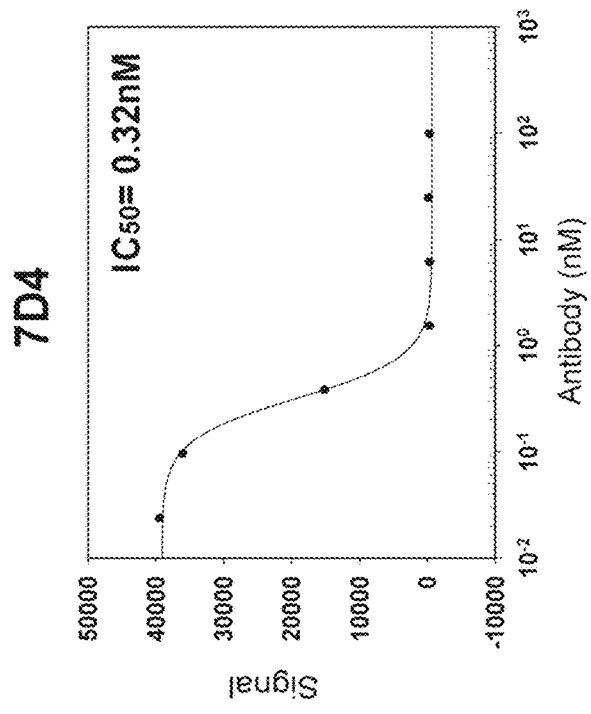
Figure 2E:
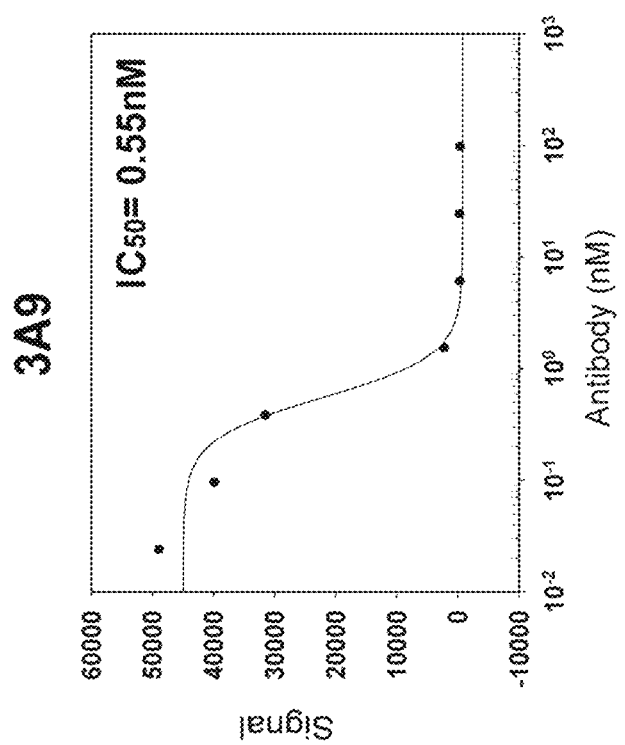

The disclosed compositions and methods may be understood more readily by reference to the following detailed description. Unless defined otherwise herein, all scientific and technical terms used in connection with the present disclosure have the same meaning as commonly understood by those of ordinary skill in the art.

All references cited herein are incorporated by reference for any purpose. To the extent a cited reference conflicts with the disclosure herein, the specification will control.

As used herein, the singular forms of a word also include the plural form, unless the context clearly dictates otherwise; as examples, the terms "a," "an," and "the" are understood to be singular or plural. By way of example, "an element" means one or more element. The term "or" means "and/or" unless the specific context indicates otherwise. All ranges, including those stated in the form of "between value X and value Y," include the endpoints and all points in between unless the context indicates otherwise.

The term "antibody" is used in the broadest sense to refer to an immunoglobulin molecule that recognizes and binds to a target, such as a protein, polypeptide, carbohydrate, polynucleotide, lipid, or combinations thereof, through at least one antigen recognition site within the variable region of the immunoglobulin molecule. The heavy chain of an antibody is composed of a heavy chain variable region ($V_H$) and a heavy chain constant region ($C_H$). The light chain is composed of a light chain variable region ($V_L$) and a light chain constant region ($C_L$). For the purposes of this application, the mature heavy chain and light chain variable regions each comprise three complementarity determining regions (CDR1, CDR2, and CDR3) and four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. An antibody may comprise one or more than one heavy chain and/or light chain. The term "antibody" includes full-length monoclonal antibodies and full-length polyclonal antibodies, as well as antibody fragments such as Fab, Fab', F(ab')$_2$, Fv, and single chain antibodies. An antibody can be any one of the five major classes of immunoglobulins: IgA, IgD, IgE, IgG, and IgM, or subclasses thereof (e.g., isotypes IgG1, IgG2 (e.g., IgG2a, IgG2b), IgG3, IgG4). The term further encompasses human antibodies, chimeric antibodies, humanized antibodies, and any modified immunoglobulin molecule containing an antigen recognition site, so long as it demonstrates one or more of the desired biological activities (e.g., binding TIGIT, etc.).

Numbering systems to describe the locations of CDR and FR regions in antibodies have been defined by various groups. One such system is the Kabat numbering system (see, e.g., Kabat et al. "Sequences of Proteins of Immunological Interest," Diane Publishing Company (1992); see also Kabat et al. "Sequences of Proteins of Immunological Interest," U.S. Department of Health and Human Services, U.S. Government Printing Office (1987 and 1991)). Exemplary CDR sequences as defined by the Kabat numbering system are set forth in Table 2 and may be used in any of the exemplary antibodies and antigen-binding fragments disclosed herein. In some embodiments, the antibodies and antigen-binding fragments of the disclosure comprise CDR sequences that match with 100% identity to the CDR sequences described herein. In some embodiments, the antibodies and antigen-binding fragments of the disclosure comprise CDR sequences that match with 90%, 91%, 92%, 93%, 94%, 95%, 96%, 97%, 98%, or 99% identity to the CDR sequences described herein.

Additional numbering systems for defining the locations of CDR and FR regions in antibodies include, e.g., the IMGT numbering system (International ImMunoGeneTics Information System (IMGT®), the Chothia numbering system (see, e.g., Al-Lazikani et al. J Mol Biol. 1997; 273:927-48), and the Chemical Computing Group (CCG) numbering system (see, e.g., Molecular Operating Environment (MOE), 2013.08; Chemical Computing Group ULC, Montreal, QC, Canada, H3A 2R7, 2018).

The term "monoconal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies and is not to be construed as requiring production of the antibody by any particular method. Exemplary methods for the production of monoclonal antibodies are described herein and others are known in the art.

The monoclonal antibodies described herein specifically include "chimeric" antibodies, in which a portion of the heavy and/or light chain is identical with or homologous to corresponding sequences in antibodies derived from a particular species or belonging to a particular antibody class or subclass, while the remainder of the chain is identical or homologous to corresponding sequences in antibodies derived from another species or belonging to another antibody class or subclass, as well as fragments of such antibodies, so long as they bind to TIGIT and/or exhibit the desired biological activity.

The term "chimeric antibody," as used herein, refers to antibodies in which (a) the constant region is altered, replaced, or exchanged such that the antigen binding site (variable region) is linked to a constant region of a different or altered class, effector function, and/or species; and/or (b) the variable region, or a portion thereof, is altered, replaced, or exchanged with a variable region, or a portion thereof, having a different or altered antigen specificity. The modifier "chimeric" indicates the character of the antibody as having structural elements from more than one species and is not to be construed as requiring production of the antibody by any particular method. For example, to create a chimeric antibody, the variable region sequences from a non-human donor antibody (e.g., a mouse donor antibody) can be linked to human constant regions using methods known in the art. For instance, a mouse anti-human TIGIT antibody can be modified by replacing its constant region with the constant region from a human immunoglobulin. Due to the replacement with a human constant region, the chimeric antibody can retain its specificity in recognizing human TIGIT while having reduced immunogenicity in human as compared to the original mouse antibody.

As used herein, the term "humanized antibody" refers to forms of antibodies that contain at least some human sequence and at least some non-human sequence. Typically, the antibody contains mainly human sequences and a minor portion of non-human sequences which confer binding specificity to the target antigen. Such antibodies include chimeric antibodies which contain minimal sequence derived from a non-human antibody and retain the reactivity of a non-human antibody while being less immunogenic in human. Typically, humanized antibodies are generated by replacing hypervariable region sequences from a human acceptor antibody with hypervariable region sequences from a non-human donor antibody (e.g., a mouse donor antibody) that binds to an antigen of interest (e.g., human TIGIT). In some cases, framework region sequences of the acceptor antibody may also be replaced with the corresponding sequences of the donor antibody (e.g., via back mutation). In addition to the sequences derived from the donor and acceptor antibodies, the humanized antibody can be further modified by the substitution of residues, either in the framework region and/or within the replaced non-human residues to refine and optimize antibody specificity, selectivity, affinity, and/or activity, as discussed herein.

In some embodiments, the antibodies and antigen-binding fragments disclosed herein are humanized. In some embodiments, the disclosed antibodies and antigen-binding fragments contain minimal sequences derived from a non-human antibody. In some embodiments, the disclosed antibodies and antigen-binding fragments retain the affinity of the non-human antibody but comprise modifications in one or more CDRs and/or frameworks. In some embodiments, the disclosed antibodies and antigen-binding fragments also exhibit one or more desirable properties not exhibited by the non-human antibody, including but not limited to lower immunogenicity and reduced toxicity. In some embodiments, the non-human antibody is a mouse antibody. In some embodiments, the non-human antibody is a mouse anti-human TIGIT antibody. Exemplary mouse anti-human TIGIT antibodies are described herein and include, but are not limited to, 7D4, 2C9, and 3A9. In some embodiments, the non-human antibody, or an antigen-binding fragment or antigen-binding domain thereof, is used as a comparator or "reference" antibody, antigen-binding fragment, or antigen-binding domain, e.g., to evaluate comparative binding affinity.

The term "antigen-binding fragment" of an antibody, as used herein, refers to one or more fragments of an antibody or protein that retain the ability to bind to an antigen (e.g., TIGIT). Antigen-binding fragments may also retain immune effector activity. It has been shown that fragments of a full-length antibody can perform the antigen binding function of a full-length antibody. Examples of binding fragments encompassed within the term "antigen-binding fragment" of an antibody include (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment, which comprises a single variable domain, e.g., a $V_H$ domain (see, e.g., Ward et al. (1989) Nature 341:544-6; and Intl. Pub. No. WO 1990/005144); and (vi) an isolated complementarity determining region (CDR). Furthermore, although the two domains of the Fv fragment, $V_L$ and $V_H$, are coded for by separate genes, they can be joined (e.g., using recombinant methods) by a synthetic linker that enables them to be made as a single protein chain in which the $V_L$ and $V_H$ regions pair to form monovalent molecules (known as single chain Fv (scFv)). See, e.g., Bird et al. (1988) Science 242:423-6; and Huston et al. (1988) Proc Natl Acad Sci. USA 85:5879-83. Such single chain antibodies are also intended to be encompassed within the term "antigen-binding fragment" of an antibody. In some embodiments, scFv molecules are incorporated into a fusion protein. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc Natl Acad Sci. USA 90:6444-8; and Poljak et al. (1994) Structure 2:1121-3). Antigen-binding fragments may be obtained using conventional techniques known to those of skill in the art, and the binding fragments may be screened for utility (e.g., binding affinity) in the same manner as are intact antibodies. Antigen-binding fragments may be prepared by cleavage of the intact protein, e.g., by protease or chemical cleavage.

The term "T cell immunoglobulin and ITIM domain" or "TIGIT," as used herein, refers to any native form of TIGIT from any vertebrate source, including mammals such as primates (e.g., humans and monkeys) and rodents (e.g., mice and rats), unless otherwise indicated. TIGIT is also known in the art as DKFZp667A205, FLJ39873, V-set and immunoglobulin domain-containing protein 9, V-set and transmembrane domain-containing protein 3, VSIG9, VSTM3, and WUCAM. The term encompasses "full-length" unprocessed TIGIT (e.g., full-length human TIGIT having the amino acid sequence of SEQ ID NO: 22), as well as any form of TIGIT that results from cellular expression or processing, such as alternative splicing events, variable promoter usage, post-transcriptional modifications, post-translational modifications, etc. (e.g., processed human TIGIT without a signal sequence, i.e., TIGIT having the amino acid sequence of amino acids 22-244 of SEQ ID NO: 22). The term also encompasses functional variants or fragments of TIGIT, including but not limited to splice variants, allelic variants, and isoforms that retain one or more biologic functions of TIGIT (i.e., variants and fragments are encompassed unless the context indicates that the term is used to refer to the wild-type protein only). The amino acid sequence of an exemplary human TIGIT may be found under UniProt Accession No. Q495A1.

The term "anti-TIGIT antibody" or "antibody that binds to TIGIT" refers to any form of antibody or antigen-binding fragment thereof that binds, e.g., specifically binds, to TIGIT. The terms encompass monoclonal antibodies (including full-length monoclonal antibodies), polyclonal antibodies, and biologically functional antibody fragments so long as they bind, e.g., specifically bind, to TIGIT. In some embodiments, an anti-TIGIT antibody or antigen-binding fragment disclosed herein may bind, e.g., specifically bind, to one or more amino acids in the extracellular domain of TIGIT, as discussed herein. In some embodiments, the extracellular domain of TIGIT comprises amino acids 24-138 of SEQ ID NO: 22.

As used herein, the term "specific," "specifically binds," or "binds specifically" refers to a binding reaction between an antibody or antigen-binding fragment (e.g., an anti-TIGIT antibody) and a target antigen (e.g., TIGIT) in a heterogeneous population of proteins and other biologics. Antibodies can be tested for specificity of binding by comparing binding to an appropriate antigen with binding to an alternate antigen or antigen mixture under a given set of conditions. If the antibody binds to the appropriate antigen with at least 2, 5, 7, 10 or more times higher affinity than to the alternate antigen or antigen mixture, then it is considered to be specific. A "specific antibody" or a "target-specific antibody" is one that only binds the target antigen (e.g., TIGIT), but does not bind (or exhibits minimal binding) to other antigens. In some embodiments, an antibody or antigen-binding fragment that specifically binds a target antigen (e.g., TIGIT) also has a $K_D$ for that target of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the $K_D$ is 1 μM to 500 μM. In some embodiments, the $K_D$ is between 500 μM to 1 μM, 1 μM to 100 nM, or 100 mM to 10 nM.

The term "epitope" refers to the portion of an antigen capable of being recognized and specifically bound by an antibody. When the antigen is a polypeptide, epitopes can be formed from contiguous amino acids or noncontiguous amino acids juxtaposed by tertiary folding of the polypeptide. The epitope bound by an antibody may be identified using any epitope mapping technique known in the art, including X-ray crystallography for epitope identification by direct visualization of the antigen-antibody complex, as well as monitoring the binding of the antibody to fragments or mutated variations of the antigen, or monitoring solvent accessibility of different parts of the antibody and the antigen. Exemplary methods for mapping antibody epitopes are described in the examples herein (see, e.g., Example 20) and are known in the art. Exemplary strategies include, but are not limited to, array-based oligo-peptide scanning, limited proteolysis, site-directed mutagenesis, high-throughput mutagenesis mapping, hydrogen-deuterium exchange, and mass spectrometry (see, e.g., Gershoni et al. (2007) 21:145-56; and Hager-Braun and Tomer (2005) Expert Rev Proteomics 2:745-56).

Competitive binding and epitope binning can also be used to determine antibodies sharing identical or overlapping epitopes. Competitive binding can be evaluated using a cross-blocking assay, such as the assay described in "Antibodies, A Laboratory Manual," Cold Spring Harbor Laboratory, Harlow and Lane ($1^{st}$ edition 1988, $2^{nd}$ edition 2014). In some embodiments, competitive binding is identified when a test antibody or binding protein reduces binding of a reference antibody or binding protein to a target antigen such as TIGIT (e.g., a binding protein comprising CDRs and/or variable regions selected from those identified in Tables 2 and 3), by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes (see, e.g., Tzartos, Methods in Molecular Biology (Morris, ed. (1998) vol. 66, pp. 55-66)). In some embodiments, competitive binding can be used to sort groups of binding proteins that share similar epitopes. For example, binding proteins that compete for binding can be "binned" as a group of binding proteins that have overlapping or nearby epitopes, while those that do not compete are placed in a separate group (i.e., bin) of binding proteins that do not have overlapping or nearby epitopes.

An "antibody that binds to the same epitope" as a reference antibody refers to an antibody that blocks binding of the reference antibody to its antigen in a competition assay by 50% or more, and/or conversely, the reference antibody blocks binding of the antibody to its antigen in a competition assay by 50% or more. Exemplary competition assays are described and exemplified herein.

The terms "amino acid" and "residue," as used herein, refer to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified in vivo, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., selenocysteine, homoserine, norleucine, and methionine sulfoxide. Such analogs may have modified R groups (e.g., selenocysteine, norleucine) or modified peptide backbones (e.g., homoserine), but retain the same basic chemical structure as a naturally occurring amino acid. Amino acid mimetics refer to chemical compounds that have a structure that is different from the general chemical structure of an amino acid, but that function in a manner similar to a naturally occurring amino acid. The three-letter and one-letter codes for exemplary amino acids are provided in Table 1.

TABLE 1

Three-letter and one-letter codes for exemplary amino acids

| Amino acid | Three-letter code | One-letter code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

An "amino acid modification" at a specified position, for example, in the Fc region of an antibody, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. In some embodiments, an amino acid modification described herein is a substitution.

For amino acid sequences, the term "identity" or "homology" refers to a relationship between the sequences of two or more polypeptides, as determined by comparing the sequences. The term "identity" also means the degree of sequence relatedness between polypeptides, as determined by the number of matches between strings of two or more amino acid residues. The percent "identity" between the two sequences is a function of the number of identical positions shared by the sequences (i.e., percent identity equals number of identical positions/total number of positions ×100), taking into account the number of gaps, and the length of each gap, which need to be introduced for optimal alignment of the two sequences. The comparison of sequences and determination of percent identity between two sequences can be accomplished using a mathematical algorithm. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Additionally, or alternatively, the protein sequences of the disclosure can further be used as a "query sequence" to perform a search against public databases to, for example, identify related sequences. For example, such searches can be performed using the BLAST program of Altschul et al. ((1990) J Mol Biol. 215(3):403-10).

Generally, the amino acid identity or homology between proteins disclosed herein and variants thereof, including variants of TIGIT and variants of antibody variable domains (including individual variant CDRs), are at least 80% identical or homologous to the sequences depicted herein, e.g., identities or homologies of at least 85%, 90%, 91%, 92%, 93%, 94%, 95%, 96%, 97%, 98%, 99%, almost 100%, or 100%.

In a similar manner, percent "nucleic acid sequence identity" with respect to nucleic acid sequences encoding the antibodies and other proteins identified herein is defined as the percentage of nucleotide residues in a candidate sequence that are identical with the nucleotide residues in the coding sequence of the specified antibody or other protein.

As used herein, the term "isolated" refers to a material that is removed from its source environment (e.g., the natural environment if it is naturally-occurring). For example, a naturally-occurring polynucleotide or polypeptide present in a living organism is not isolated, but the same polynucleotide or polypeptide separated from some or all of the coexisting materials in the living organism, is isolated.

An "isolated antibody," as used herein, is an antibody that has been identified and separated from one or more (e.g., the majority) of the components (by weight) of its source environment, e.g., from the components of a hybridoma cell culture or a different cell culture that was used for its production (e.g., producer cells such as mouse myeloma NS0 cells or Chinese hamster ovary cells (e.g., CHO-S cells) that recombinantly express the antibody). In some embodiments, the separation is performed such that it sufficiently removes components that may otherwise interfere with the suitability of the antibody for the desired applications (e.g., for therapeutic use of an anti-TIGIT antibody). Methods for preparing isolated antibodies are known in the art and include, without limitation, protein A chromatography, anion exchange chromatography, cation exchange chromatography, virus retentive filtration, and ultrafiltration.

Binding "affinity" refers to the strength of interaction between antibody and antigen at single antigenic sites. Within each antigenic site, the variable region of the antibody "arm" interacts through weak non-covalent forces with the antigen at numerous sites. In general, the more interactions, the stronger the affinity. $K_D$ and affinity are inversely related. In some embodiments, the anti-TIGIT antibody or antigen-binding fragment of the disclosure retains the ability to bind to TIGIT (e.g., human TIGIT) with a $K_D$ of about $1\times10^{-6}$ M or less.

The term "$K_D$," as used herein, refers to the equilibrium dissociation constant, which is obtained from the ratio of $k_d$ to $k_a$ (i.e., $k_d/k_a$) and is generally expressed as a molar concentration (M). The term "$k_a$," as used herein, is refers to the association rate of a particular antibody-antigen interaction, whereas the term "$k_d$," as used herein, refers to the dissociation rate of a particular antibody-antigen interaction. Exemplary methods for measuring $K_D$ values for antibodies are described in the examples herein (see, e.g., Example 5) and others are known in the art.

An "affinity-matured" antibody is one with one or more alterations in one or more CDRs thereof that result in an improvement in the affinity of the antibody for a target antigen, compared to a parent antibody that does not possess those alteration(s). In some embodiments, an affinity-matured antibody has nanomolar or even picomolar affinities for the target antigen. Exemplary methods for producing affinity-matured antibodies are described in the examples herein (see, e.g., Examples 13, 14, and 17) and are known in the art, including affinity maturation by VH- and VL-domain shuffling, random mutagenesis of CDR and/or framework residues, etc.

The term "Fc region" herein is used to define a C-terminal region of an immunoglobulin heavy chain, including native-sequence Fc regions and variant Fc regions. The C-terminal lysine of the Fc region may be removed, for example, during production or purification of the antibody, or by recombinantly engineering the nucleic acid encoding a heavy chain of the antibody. Accordingly, a composition of intact antibodies may comprise antibody populations with all C-terminal lysine residues removed, antibody populations with no C-terminal lysine residues removed, and antibody populations having a mixture of antibodies with and without the C-terminal lysine residue. Suitable native-sequence Fc regions for use in the antibodies of the invention include human IgG1, IgG2 (e.g., IgG2a, IgG2b), IgG3, and IgG4.

"Fc receptor" or "FcR," as used herein, describes a receptor that binds to the Fc region of an antibody. In some embodiments, an FcR is a native sequence human FcR. In some embodiments, an FcR is one which binds an IgG antibody (a gamma receptor) and includes receptors of the FCγRI, FCγRII, and FCγRIII subclasses, including allelic variants and alternatively spliced forms of these receptors. Other FcRs, including those to be identified in the future, are encompassed by the term "FcR" herein.

"Effector cells" refer to leukocytes that express one or more FcRs and perform effector functions. In some embodiments, the cells express at least FCγRIII and/or perform ADCC effector function(s). Examples of human leukocytes which mediate ADCC include peripheral blood mononuclear cells (PBMC), natural killer (NK) cells, monocytes, cytotoxic T cells, and neutrophils.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or "ADCC" refers to a form of cytotoxicity in which secreted immunoglobulin bound onto Fc receptors present on certain cytotoxic effector cells (e.g., NK cells, monocytes) enable the cytotoxic effector cells to bind specifically to an antigen-bearing target cell and subsequently kill the target cell with cytotoxins. To assess ADCC activity, in some embodiments, an in vitro ADCC assay, such as the ones described in U.S. Pat. No. 5,500,362 or 5,821,337 or 6,737,056, may be performed. Useful effector cells for such assays include PBMC and NK cells. Alternatively, or additionally, ADCC activity may be assessed in vivo, e.g., in an animal model such as that disclosed in Clynes et al. ((1998) PNAS (USA) 95:652-6). An exemplary assay for assessing ADCC activity is also described in the examples herein (see, e.g., Example 19).

As used herein, the term "immune cell" includes cells that are of hematopoietic origin and that play a role in the immune response. Immune cells include lymphocytes, such as B cells and T cells (e.g., cytotoxic T cells, helper T cells); natural killer cells; and myeloid cells, such as monocytes, macrophages, eosinophils, mast cells, basophils, and granulocytes. The term "T cell" includes cytotoxic (CD8+) T cells and helper (CD4+) T cells. The term T cell also includes both T helper 1 type T cells and T helper 2 type T cells. The term "antigen-presenting cell" includes professional antigen-presenting cells (e.g., B lymphocytes, monocytes, dendritic cells, and Langerhans cells) as well as other antigen-presenting cells (e.g., keratinocytes, endothelial cells, astrocytes, fibroblasts, and oligodendrocytes).

As used herein, the term "immune response" includes T cell-mediated and/or B cell-mediated immune responses that are influenced by modulation of T cell costimulation. Exemplary immune responses include B cell responses (e.g., antibody production), T cell responses (e.g., cytokine production, cellular cytotoxicity), and activation of cytokine responsive cells, e.g., macrophages. As used herein, the term "downmodulation" with reference to an immune response includes a diminution in any one or more immune responses, while the term "upmodulation" with reference to an immune response includes an increase, enhancement, or stimulation of any one or more immune responses. It will be understood that upmodulation of one type of immune response may lead to a corresponding downmodulation in another type of immune response. For example, upmodulation of the production of certain cytokines can lead to downmodulation of cellular immune responses.

As used herein, the term "costimulatory receptor" includes receptors which transmit a costimulatory signal to an immune cell, e.g., CD28 or ICOS. As used herein, the term "inhibitory receptor" includes receptors which transmit a negative signal to an immune cell (e.g., CTLA-4 or PD-1).

As used herein, the term "costimulate," with reference to activated immune cells, includes the ability of a costimulatory molecule to provide a second, non-activating, receptor-mediated signal (a "costimulatory signal") that induces proliferation or effector function. For example, a costimulatory signal can result in cytokine secretion, e.g., in a T cell that has received a T cell-receptor-mediated signal. Immune cells that have received a cell receptor-mediated signal, e.g., via an activating receptor, are referred to herein as "activated immune cells."

An inhibitory signal as transduced by an inhibitory receptor can occur even if a costimulatory receptor (such as CD28 or ICOS) in not present on the immune cell and, thus, is not simply a function of competition between inhibitory receptors and costimulatory receptors for binding of costimulatory molecules (Fallarino et al. (1998) J. Exp. Med. 188: 205). Transmission of an inhibitory signal to an immune cell can result in unresponsiveness, anergy, or programmed cell death in the immune cell. In some embodiments, transmission of an inhibitory signal operates through a mechanism that does not involve apoptosis. As used here in the term "apoptosis" includes programmed cell death which can be characterized using techniques which are known in the art. Apoptotic cell death can be characterized, e.g., by cell shrinkage, membrane blebbing, and chromatin condensation culminating in cell fragmentation. Cells undergoing apoptosis also display a characteristic pattern of internucleosomal DNA cleavage.

In some embodiments, provided herein are therapeutic methods and uses for the described antibodies and/or antigen-binding fragments, e.g., in activating and/or killing one or more immune cells. In some embodiments, the therapeutic methods and uses described herein are useful in increasing, enhancing, or stimulating an immune response or function in a subject. In some embodiments, immune response or function is increased, enhanced, and/or stimulated by activating effector cells (e.g., T cells), expanding (increasing) an effector cell population, and/or killing target cells (e.g., target tumor cells) in the subject as a result of treatment with an antibody or antigen-binding fragment of the disclosure.

"Immune cell activation," as used herein, and pluralizations and variations of this root term (e.g., "activating an immune cell"), refers to immune cell proliferation, activating or enhancing expression of one or more markers of immune cells (e.g., CD69, CD71), induction of secretion of a signal substance (e.g. IFN-γ, IL-2), induction of secretion of a cytolytic molecule (e.g., perforin, granzyme B), enhanced cytotoxicity, cytokine production, cell migration, cell proliferation, or combinations of any two or more of these properties. In some embodiments, immune cell activation is characterized by cytokine secretion (e.g., secretion of IFN-γ, IL-2, or both). In some embodiments, immune cell activation is characterized by enhancing T cell function. Immune cell activation may be measured in vitro, e.g., by the assessment of T cell proliferation upon antigen- or TCR-mediated stimulation. Exemplary methods of evaluating immune cell activation are described herein (see, e.g., Examples 7-9) and others are known in the art.

"Enhancing T cell function" means to induce, cause, or stimulate a T cell to have a sustained or amplified biological function, or to renew or reactivate exhausted or inactive T cells. Examples of enhancing T cell function include increased secretion of IFN-γ from cytotoxic T cells, increased proliferation, and increased antigen responsiveness (e.g., viral, pathogen, or tumor clearance) relative to such levels before the intervention. In some embodiments, the level of enhancement is as least 50%, 60%, 70%, 80%, 90%, 100%, 120%, 150%, 200%, and may be measured using methods known to those of ordinary skill in the art.

An "immune-related disease" refers to any pathology that occurs when physiological pathways, which in normal physiology respond to insult or injury, initiate repair from insult or injury, and/or mount innate and acquired defenses, cause additional insult or injury that is directly related to the intensity of the response (e.g., as a consequence of abnormal regulation or excessive stimulation) or as a reaction to self. Particular examples of immune-related diseases described herein include cancer (neoplasia), immune-mediated inflammatory diseases, non-immune-mediated inflammatory diseases, infectious diseases, and immunodeficiency diseases. In some embodiments, an immune-related disease may be a disease, disorder, or condition of T cells characterized by decreased responsiveness to antigenic stimulation. In some embodiments, an immune-related disease may be one in which T cells are anergic or have decreased ability to secrete cytokines, proliferate, or execute cytolytic activity. In some embodiments, the decreased responsiveness results in ineffective control of a pathogen or tumor expressing an immunogen. Examples of immune-related diseases characterized by T cell dysfunction include unresolved acute infection, chronic infection, and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage, and tumor clearance.

"Immunogenicity" or "immunogenic" refers to the ability of a particular agent or composition to elicit an immune response, e.g., a T cell response. The immune response can be antibody- or cell-mediated, or both. Tumors are immunogenic and enhancing tumor immunogenicity may aid in the clearance of the tumor cells by the immune response. In some embodiments, tumor immunogenicity may be enhanced by treatment with an anti-TIGIT antibody or antigen-binding fragment described herein.

As used herein, the term "checkpoint inhibitor" refers to any therapeutic agent, including any small molecule chemical compound, antibody, nucleic acid molecule, or polypeptide, or any fragments thereof, that inhibits one or more of the molecules that dampen the immune response to an immunologic stimulus, thereby allowing more extensive immune activity.

The term "inhibit" or "inhibition of," as used herein, means to reduce by a statistically significant measurable amount compared to a control (e.g., an untreated sample), and can include but does not require complete prevention or inhibition.

As used herein, the terms "cancer" and "tumor" are used interchangeably and, in either the singular or plural form, refer to cells that have undergone a malignant transformation that makes them pathological to the host organism. Primary cancer cells can be readily distinguished from non-cancerous cells by well-established techniques, such as histological examination. The definition of a cancer cell, as used herein, includes not only a primary cancer cell, but any cell derived from a cancer cell ancestor. This includes metastasized cancer cells, and in vitro cultures and cell lines derived from cancer cells. A cancer may manifest as a solid tumor, e.g., a tumor detectable on the basis of tumor mass, e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a subject. Tumors may also be a hematopoietic (or hematologic or hematological or blood-related) cancer, for example, cancers derived from blood cells or immune cells, which may be referred to as "liquid tumors." Particular examples of cancers described herein include colorectal cancer and leukemia. In some embodiments, a cancer is a colorectal cancer or leukemia.

As used herein, the term "infection" refers to the invasion of an organism's body tissues by disease-causing agents, their multiplication, and the reaction of host tissues to the infectious agents and the toxins they produce. The term encompasses both acute and chronic infections. Exemplary infectious agents include pathogens such as viruses and related agents such as viroids and prions; bacteria; fungi; and parasites. An "infectious disease," also known as a transmissible disease or communicable disease, is an illness resulting from an infection. An exemplary infection or infectious disease is a human T cell leukemia virus type 1-associated disease.

The terms "subject" and "patient" are used interchangeably herein to refer to any animal, such as any mammal, including but not limited to, humans, non-human primates, rodents, and the like. In some embodiments, the subject or patient is a mammal. In some embodiments, the subject or patient is a human.

As used herein, the term "agent" refers to a chemical compound, a mixture of chemical compounds, a biological macromolecule, or an extract made from biological materials. The term "therapeutic agent" refers to an agent that is capable of modulating a biological process and/or has biological activity. The anti-TIGIT antibodies and antigen-binding fragments described herein are exemplary therapeutic agents.

A "pharmaceutical composition" refers to a preparation which is in such form as to permit administration and subsequently provide the intended biological activity of the active agent(s) and/or to achieve a therapeutic effect, and which contains no additional components which are unacceptably toxic to a subject to which the formulation would be administered. The pharmaceutical composition may be sterile.

A "pharmaceutically acceptable carrier," as used herein, includes carriers, diluents, excipients, or stabilizers that are nontoxic to the cell or mammal being exposed thereto at the dosages and concentrations employed. In some embodiments, a pharmaceutically acceptable carrier is an aqueous pH buffered solution. Examples of pharmaceutically acceptable carriers include buffers such as phosphate, citrate, and other organic acids; antioxidants including ascorbic acid; low molecular weight (e.g., less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polyethylene glycol (PEG). The use of such carriers for pharmaceutically active substances is well known in the art. Except insofar as any conventional carrier is incompatible with the active agent(s), use thereof in the disclosed compositions is contemplated.

An "effective amount" of, e.g., an antibody or antigen-binding fragment disclosed herein, is an amount sufficient to perform a specifically stated purpose, for example to produce a therapeutic effect after administration, such as an up- or downmodulation of an immune response, activation of one or more immune cells, killing of one or more immune cells, a reduction in tumor growth rate or tumor volume, a reduction in a symptom of an immune-related disease (e.g., a cancer or an infection or infectious disease), or some other indicia of treatment efficacy. The term "therapeutically effective amount" refers to an amount of an antibody or antigen-binding fragment effective to treat a disease or disorder in a subject. In the case of cancer, a therapeutically effective amount of an antibody or antigen-binding fragment can reduce the number of cancer cells, reduce tumor size, inhibit (e.g., slow or stop) tumor metastasis, inhibit (e.g., slow or stop) tumor growth, and/or relieve one or more symptoms. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, the term "treat" or "treatment" or "therapeutic" (and grammatically related terms) refers to any improvement of any consequence of disease, such as prolonged survival, less morbidity, and/or a lessening of side effects which result from an alternative therapeutic modality. As is readily appreciated in the art, full eradication of disease is encompassed but not required for a treatment act. The term "treat" or "treatment," as used herein, may also refer to the administration of a described antibody or antigen-binding fragment to a subject, e.g., a subject having or suspected of having an immune-related disease, e.g., a cancer or an infection or infectious disease. The treatment can be to cure, heal, alleviate, relieve, alter, remedy, ameliorate, palliate, improve, or otherwise affect the disease, the symptoms of the disease, or the subject's predisposition toward the disease. In some embodiments, in addition to treating a subject with a disease, a composition disclosed herein can also be provided prophylactically to prevent or reduce the likelihood of developing that disease.

Anti-TIGIT Antibodies

The present disclosure relates, in some embodiments, to antibodies and antigen-binding fragments thereof that bind to and/or modulate the activity of TIGIT, as well as their use in therapeutic compositions. In some embodiments, the antibodies and antigen-binding fragments disclosed herein specifically bind to TIGIT. In some embodiments, the antibodies and antigen-binding fragments disclosed herein are capable of reducing or blocking the interaction of TIGIT and CD155. In some embodiments, the antibodies and antigen-binding fragments disclosed herein may be used alone or administered as part of pharmaceutical compositions or combination therapies.

In some embodiments, the antibodies and antigen-binding fragments disclosed herein are humanized. In some embodiments, the antibodies and antigen-binding fragments disclosed herein contain minimal sequence derived from a non-human (e.g., mouse) antibody and retain the reactivity of the non-human antibody while being less immunogenic in human. In some embodiments, the antibodies and antigen-binding fragments disclosed herein have one or more improved properties, including, for example, binding affinity, cross-reactivity, T cell activation activity, in vivo anti-cancer activity, or antibody-dependent cell-mediated cytotoxicity, as compared to a reference anti-TIGIT antibody or antigen-binding fragment. Specifically, in some embodiments, the antibodies and antigen-binding fragments disclosed herein may demonstrate one or more of: high binding affinity to human TIGIT; cross-reactivity between human TIGIT, cynomolgus monkey (cyno) TIGIT, and/or mouse TIGIT; effective T cell activation activity; effective in vivo anti-cancer activity; and/or potent antibody-dependent cell-mediated cytotoxicity against TIGIT-expressing regulatory T cells, e.g., as compared to a reference anti-TIGIT antibody or antigen-binding fragment. By virtue of some or all of these improved properties, the disclosed antibodies and antigen-binding fragments may be useful as therapeutic agents, e.g., to treat or delay the progression of an immune-related disease (e.g., a cancer or an infection or infectious disease) in a subject (e.g., a human).

In some embodiments, the antibodies and antigen-binding fragments disclosed herein bind to TIGIT, e.g., as expressed on an immune cell. The antibody or antigen-binding fragment may bind to TIGIT with a dissociation constant ($K_D$) of ≤1 mM, ≤100 nM, ≤10 nM, or any amount in between, as measured by, e.g., flow cytometry analysis. In some embodiments, the $K_D$ is between 0.1 nM to 10 nM, as measured by, e.g., flow cytometry analysis.

In some embodiments, the antibody or antigen-binding fragment is a four-chain antibody (also referred to as an immunoglobulin) comprising two heavy chains and two light chains. In some embodiments, the antibody or antigen-binding fragment is a two-chain half body (one light chain and one heavy chain), or an antigen-binding fragment of an immunoglobulin. In some embodiments, the antibody or antigen-binding fragment is an antigen-binding fragment of an immunoglobulin that retains the ability to bind a target antigen (e.g., TIGIT) and/or provide a function of an immunoglobulin.

In some embodiments, an antibody or antigen-binding fragment disclosed herein may comprise a paired set of heavy and light chain variable regions taken from those listed in Table 3, or the set of six CDR sequences from the paired heavy and light chain set, e.g., a set of CDRs listed in Table 2. In some embodiments, the antibody or antigen-binding fragment further comprises human heavy and light chain frameworks (optionally with one or more back mutations, e.g., to improve binding affinity) and/or human heavy and light chain constant regions or fragments thereof. For instance, the antibody or antigen-binding fragment may comprise a human IgG heavy chain constant region (optionally with one or more mutations, e.g., to modify effector function) and a human kappa or lambda light chain constant region. In some embodiments, the antibody or antigen-binding fragment comprises a human immunoglobulin G subtype 1 (IgG1) heavy chain constant region with a human Ig kappa light chain constant region.

Amino acid sequences of exemplary antibodies of the disclosure are set forth in Tables 2-5.

TABLE 2

Amino acid sequences of Kabat CDRs for anti-TIGIT antibodies

| mAb | Ig chain CDR | SEQ ID NO | Amino acid sequence |
| --- | --- | --- | --- |
| 7D4 | HCDR1 | 1 | YTFTNYWIG |
|  | HCDR2 | 2 | DIYPGSSFTNSNEKFKG |
|  | HCDR3 | 3 | LGRGYWYFDV |
|  | LCDR1 | 4 | SASSSVSYIH |
|  | LCDR2 | 5 | TTSNLAS |
|  | LCDR3 | 6 | HQWSRYPT |

TABLE 2-continued

Amino acid sequences of Kabat CDRs for anti-TIGIT antibodies

| mAb | Ig chain CDR | SEQ ID NO | Amino acid sequence |
|---|---|---|---|
| 2C9 | HCDR1 | 7 | YTFTDSYIN |
|  | HCDR2 | 8 | RFYPGSGNTY |
|  | HCDR3 | 9 | EAWLLFYGMDY |
|  | LCDR1 | 10 | SANSSVSYMY |
|  | LCDR2 | 11 | RTSNLAS |
|  | LCDR3 | 12 | QQYHSYPLT |
| 3A9 | HCDR1 | 13 | YTFTSYWMH |
|  | HCDR2 | 14 | NIDPSDSATH |
|  | HCDR3 | 15 | TGIDYGSSYFDY |
|  | LCDR1 | 16 | RASQSVSTSSYSYIH |
|  | LCDR2 | 17 | YASNLES |
|  | LCDR3 | 18 | QHNWEIPRT |
| hz7D4 | HCDR1 | 1 | YTFTNYWIG |
|  | HCDR2 | 2 | DIYPGSSFTNSNEKFKG |
|  | HCDR3 | 3 | LGRGYWYFDV |
|  | LCDR1 | 4 | SASSSVSYIH |
|  | LCDR2 | 5 | TTSNLAS |
|  | LCDR3 | 6 | HQWSRYPT |
| 1G3 | HCDR1 | 1 | YTFTNYWIG |
|  | HCDR2 | 2 | DIYPGSSFTNSNEKFKG |
|  | HCDR3 | 19 | DMVGYWYFDV |
|  | LCDR1 | 4 | SASSSVSYIH |
|  | LCDR2 | 5 | TTSNLAS |
|  | LCDR3 | 6 | HQWSRYPT |
| 2F1 | HCDR1 | 1 | YTFTNYWIG |
|  | HCDR2 | 2 | DIYPGSSFTNSNEKFKG |
|  | HCDR3 | 20 | VIVGYWYFDV |
|  | LCDR1 | 4 | SASSSVSYIH |
|  | LCDR2 | 5 | TTSNLAS |
|  | LCDR3 | 6 | HQWSRYPT |
| 3H2 | HCDR1 | 1 | YTFTNYWIG |
|  | HCDR2 | 2 | DIYPGSSFTNSNEKFKG |
|  | HCDR3 | 21 | IRLGYWYFDV |
|  | LCDR1 | 4 | SASSSVSYIH |
|  | LCDR2 | 5 | TTSNLAS |
|  | LCDR3 | 6 | HQWSRYPT |
| 1A11 | HCDR1 | 1 | YTFTNYWIG |
|  | HCDR2 | 2 | DIYPGSSFTNSNEKFKG |
|  | HCDR3 | 3 | LGRGYWYFDV |
|  | LCDR1 | 4 | SASSSVSYIH |
|  | LCDR2 | 5 | TTSNLAS |
|  | LCDR3 | 23 | QLFRSGSA |
| 1E3 | HCDR1 | 1 | YTFTNYWIG |
|  | HCDR2 | 2 | DIYPGSSFTNSNEKFKG |
|  | HCDR3 | 3 | LGRGYWYFDV |
|  | LCDR1 | 4 | SASSSVSYIH |
|  | LCDR2 | 5 | TTSNLAS |
|  | LCDR3 | 24 | STFTVINL |

TABLE 3

Amino acid sequences of variable regions for anti-TIGIT antibodies

| mAb | Ig chain | SEQ ID NO | Amino acid sequence |
|---|---|---|---|
| 7D4 | Heavy chain | 25 | QVQLKHSGAELVRPGTSVKMSCKASGYTFTNYWIGWAKQRPGHGLEWIGDIYPGSSFTNSNEKFKGKATLTADKSSSTAYMQFSSLTSEDSAIYYCAKLGRGYWYFDVWGTGTSVTVSA |
|  | Light chain | 26 | DIVLTQSPAIMSASLGEEITLTCSASSSVSYIHWYQQKSGTSPKLLIYTTSNLASGVPSRFSGSGSGTFYSLTISSVEAEDAADYYCHQWSRYPTFGGGTKLEIK |
| 2C9 | Heavy chain | 27 | DIQLKQSGAELVRPGASVKLSCKASGYTFTDSYINWVKQRPGQGLEWIARFYPGSGNTYYNEKFKGKATLTAEKSSSTAYMQLSSLTSEDSAVYFCAREAWLLFYGMDYWGQGTTVTVSS |
|  | Light chain | 28 | DIVLTQSPAIMSASPGEKVTISCSANSSVSYMYWYQQKPGSSPKPWIYRTSNLASGVPARFSGSGSGTSYSLTISSMEAEDAATYYCQQYHSYPLTFGAGTKLELK |
| 3A9 | Heavy chain | 29 | QVQLQQPGAELVRPGSSVKLSCKASGYTFTSYWMHWVKQRPIQGLEWIGNIDPSDSATHYNQKFKDKATLTVDKSSSTAYMHLSSLTSEDSAVYYCARTGIDYGSSYFDYWGQGTILTVSS |
|  | Light chain | 30 | DIVLTQSPASLAVSLGQRATISCRASQSVSTSSYSYIHWYQQKPGQPPKLLIKYASNLESGVPARFSGSGSGTDFTLNIHPVEEDTATYYCQHNWEIPRTFGGGTKLEIK |
| hz7D4 | Heavy chain | 31 | EVQLVQSGGGLVKPGGSLRLSCAASGYTFTNYWIGWVRQTPGKGLEWVGDIYPGSSFTNSNEKFKGRFTISADKSKNTAYLQMNSLRAEDTAVYYCARLGRGYWYFDVWGQGTLVTVSS |
|  | Light chain | 32 | DIVLTQSPATLSASLGERATLSCSASSSVSYIHWYQQKPGQAPKLLIYTTSNLASGVPSRFSGSGSGTDFTLTISSLEAEDFATYYCHQWSRYPTFGGGTKLEIK |
| 1G3 | Heavy chain | 33 | DIQLVQSGGGLVKPGGSLRLSCAASGYTFTNYWIGWVRQTPGKGLEWVGDIYPGSSFTNSNEKFKGRFTISADKSKNTAYLQMNSLRAEDTAVYYCARDMVGYWYFDVWGQGTLVTVSS |
|  | Light chain | 34 | DIVLTQSPATLSASLGERATLSCSASSSVSYIHWYQQKPGQAPKLLIYTTSNLASGVPSRFSGSGSGTDFTLTISSLEAEDFATYYCHQWSRYPTFGGGTKLEIK |
| 2F1 | Heavy chain | 35 | DIQLVQSGGGLVKPGGSLRLSCAASGYTFTNYWIGWVRQTPGKGLEWVGDIYPGSSFTNSNEKFKGRFTISADKSKNTAYLQMNSLRAEDTAVYYCARVIVGYWYFDVWGQGTLVTVSS |
|  | Light chain | 36 | DIVLTQSPATLSASLGERATLSCSASSSVSYIHWYQQKPGQAPKLLIYTTSNLASGVPSRFSGSGSGTDFTLTISSLEAEDFATYYCHQWSRYPTFGGGTKLEIK |
| 3H2 | Heavy chain | 37 | DIQLVQSGGGLVKPGGSLRLSCAASGYTFTNYWIGWVRQTPGKGLEWVGDIYPGSSFTNSNEKFKGRFTISADKSKNTAYLQMNSLRAEDTAVYYCARIRLGYWYFDVWGQGTLVTVSS |
|  | Light chain | 38 | DIVLTQSPATLSASLGERATLSCSASSSVSYIHWYQQKPGQAPKLLIYTTSNLASGVPSRFSGSGSGTDFTLTISSLEAEDFATYYCHQWSRYPTFGGGTKLEIK |
| 1A11 | Heavy chain | 39 | EVQLVQSGGGLVKPGGSLRLSCAASGYTFTNYWIGWVRQTPGKGLEWVGDIYPGSSFTNSNEKFKGRFTISADKSKNTAYLQMNSLRAEDTAVYYCARLGRGYWYFDVWGQGTLVTVSS |
|  | Light chain | 40 | DIVLTQSPATLSASLGERATLSCSASSSVSYIHWYQQKPGQAPKLLIYTTSNLASGVPSRFSGSGSGTDFTLTISSLEAEDFATYYCQLFRSGSAFGGGTKLEIK |

TABLE 3-continued

Amino acid sequences of variable regions for anti-TIGIT antibodies

| mAb | Ig chain | SEQ ID NO | Amino acid sequence |
|---|---|---|---|
| 1E3 | Heavy chain | 41 | EVQLVQSGGGLVKPGGSLRLSCAASGYT FTNYWIGWVRQTPGKGLEWVGDIYPGSS FTNSNEKFKGRFTISADKSKNTAYLQMN SLRAEDTAVYYCARLGRGYWYFDVWGQG TLVTVSS |
| | Light chain | 42 | DIVLTQSPATLSASLGERATLSCSASSS VSYIHWYQQKPGQAPKLLIYTTSNLASG VPSRFSGSGSGTDFTLTISSLEAEDFAT YYCSTFTVINLFGGGTKLEIK |

TABLE 4

Amino acid sequences of constant regions for anti-TIGIT antibodies

| Ig chain | Class | SEQ ID NO | Amino acid sequence |
|---|---|---|---|
| Heavy chain | hIgG1 | 43 | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYNSTYRVV SVLTVLHQDWLNGKEYKCKVSNKALPAPIEK TISKAKGQPREPQVYTLPPSRDELTKNQVSL TCLVKGFYPSDIAVEWESNGQPENNYKTTPP VLDSDGSFFLYSKLTVDKSRWQQGNVFSCSV MHEALHNHYTQKSLSLSPG |
| | hIgG1-DLE | 44 | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPDVF LFPPKPKDTLMISRTPEVTCVVVDVSHEDPE VKFNWYVDGVEVHNAKTKPREEQYNSTYRVV SVLTVLHQDWLNGKEYKCKVSNKALPLPEEK TISKAKGQPREPQVYTLPPSRDELTKNQVSL TCLVKGFYPSDIAVEWESNGQPENNYKTTPP VLDSDGSFFLYSKLTVDKSRWQQGNVFSCSV MHEALHNHYTQKSLSLSPG |
| Light chain | kappa | 45 | RTVAAPSVFIFPPSDEQLKSGTASVVCLLNN FYPREAKVQWKVDNALQSGNSQESVTEQDSK DSTYSLSSTLTLSKADYEKHKVYACEVTHQG LSSPVTKSFNRGEC |

TABLE 5

Amino acid sequences of full-length Ig chains for select anti-TIGIT antibodies

| mAb | Ig chain | SEQ ID NO | Amino acid sequence |
|---|---|---|---|
| 1A11 | Heavy chain (hIgG1) | 46 | EVQLVQSGGGLVKPGGSLRLSCAASGYT FTNYWIGWVRQTPGKGLEWVGDIYPGSS FTNSNEKFKGRFTISADKSKNTAYLQMN SLRAEDTAVYYCARLGRGYWYFDVWGQG TLVTVSSASTKGPSVFPLAPSSKSTSGG TAALGCLVKDYFPEPVTVSWNSGALTSG VHTFPAVLQSSGLYSLSSVVTVPSSSLG TQTYICNVNHKPSNTKVDKKVEPKSCDK THTCPPCPAPELLGGPSVFLFPPKPKDT LMISRTPEVTCVVVDVSHEDPEVKFNWY VDGVEVHNAKTKPREEQYNSTYRVVSVL TVLHQDWLNGKEYKCKVSNKALPAPIEK TISKAKGQPREPQVYTLPPSRDELTKNQ VSLTCLVKGFYPSDIAVEWESNGQPENN YKTTPPVLDSDGSFFLYSKLTVDKSRWQ QGNVFSCSVMHEALHNHYTQKSLSLSPG |
| | Heavy chain (hIgG1-DLE) | 47 | EVQLVQSGGGLVKPGGSLRLSCAASGYT FTNYWIGWVRQTPGKGLEWVGDIYPGSS FTNSNEKFKGRFTISADKSKNTAYLQMN SLRAEDTAVYYCARLGRGYWYFDVWGQG TLVTVSSASTKGPSVFPLAPSSKSTSGG TAALGCLVKDYFPEPVTVSWNSGALTSG VHTFPAVLQSSGLYSLSSVVTVPSSSLG TQTYICNVNHKPSNTKVDKKVEPKSCDK THTCPPCPAPELLGGPDVFLFPPKPKDT LMISRTPEVTCVVVDVSHEDPEVKFNWY VDGVEVHNAKTKPREEQYNSTYRVVSVL TVLHQDWLNGKEYKCKVSNKALPLPEEK TISKAKGQPREPQVYTLPPSRDELTKNQ VSLTCLVKGFYPSDIAVEWESNGQPENN YKTTPPVLDSDGSFFLYSKLTVDKSRWQ QGNVFSCSVMHEALHNHYTQKSLSLSPG |
| | Light chain | 48 | DIVLTQSPATLSASLGERATLSCSASSS VSYIHWYQQKPGQAPKLLIYTTSNLASG VPSRFSGSGSGTDFTLTISSLEAEDFAT YYCQLFRSGSAFGGGTKLEIKRTVAAPS VFIFPPSDEQLKSGTASVVCLLNNFYPR EAKVQWKVDNALQSGNSQESVTEQDSKD STYSLSSTLTLSKADYEKHKVYACEVTH QGLSSPVTKSFNRGEC |
| 1E3 | Heavy chain (hIgG1) | 49 | EVQLVQSGGGLVKPGGSLRLSCAASGYT FTNYWIGWVRQTPGKGLEWVGDIYPGSS FTNSNEKFKGRFTISADKSKNTAYLQMN SLRAEDTAVYYCARLGRGYWYFDVWGQG TLVTVSSASTKGPSVFPLAPSSKSTSGG TAALGCLVKDYFPEPVTVSWNSGALTSG VHTFPAVLQSSGLYSLSSVVTVPSSSLG TQTYICNVNHKPSNTKVDKKVEPKSCDK THTCPPCPAPELLGGPSVFLFPPKPKDT LMISRTPEVTCVVVDVSHEDPEVKFNWY VDGVEVHNAKTKPREEQYNSTYRVVSVL TVLHQDWLNGKEYKCKVSNKALPAPIEK TISKAKGQPREPQVYTLPPSRDELTKNQ VSLTCLVKGFYPSDIAVEWESKGQPENN YKTTPPVLDSDGSFFLYSKLTVDKSRWQ QGNVFSCSVMHEALHNHYTQKSLSLSPG |
| | Heavy chain (hIgG1-DLE) | 50 | EVQLVQSGGGLVKPGGSLRLSCAASGYT FTNYWIGWVRQTPGKGLEWVGDIYPGSS FTNSNEKFKGRFTISADKSKNTAYLQMN SLRAEDTAVYYCARLGRGYWYFDVWGQG TLVTVSSASTKGPSVFPLAPSSKSTSGG TAALGCLVKDYFPEPVTVSWNSGALTSG VHTFPAVLQSSGLYSLSSVVTVPSSSLG TQTYICNVNHKPSNTKVDKKVEPKSCDK THTCPPCPAPELLGGPDVFLFPPKPKDT LMISRTPEVTCVVVDVSHEDPEVKFNWY VDGVEVHNAKTKPREEQYNSTYRVVSVL TVLHQDWLNGKEYKCKVSNKALPLPEEK TISKAKGQPREPQVYTLPPSRDELTKNQ VSLTCLVKGFYPSDIAVEWESNGQPENN YKTTPPVLDSDGSFFLYSKLTVDKSRWQ QGNVFSCSVMHEALHNHYTQKSLSLSPG |
| | Light chain | 51 | DIVLTQSPATLSASLGERATLSCSASSS VSYIHWYQQKPGQAPKLLIYTTSNLASG VPSRFSGSGSGTDFTLTISSLEAEDFAT YYCSTFTVINLFGGGTKLEIKRTVAAPS VFIFPPSDEQLKSGTASVVCLLNNFYPR EAKVQWKVDNALQSGNSQESVTEQDSKD STYSLSSTLTLSKADYEKHKVYACEVTH QGLSSPVTKSFNRGEC |

In some embodiments, an antibody or antigen-binding fragment disclosed herein may comprise any set of heavy and light chain variable regions listed in the tables above, or the set of six CDR sequences from the heavy and light chain set, e.g., by transplanting the six CDRs into a chosen human donor antibody framework. In some embodiments, an antibody or antigen-binding fragment disclosed herein may comprise amino acid sequences that are homologous to the sequences listed in the tables above, so long as the antibody or antigen-binding fragment retains the ability to bind to TIGIT (e.g., with a $K_D$ of less than $1 \times 10^{-8}$ M) and/or retains one or more functional properties of the antibodies and antigen-binding fragments disclosed herein (e.g., ability to reduce or block the interaction of TIGIT and CD155, etc.).

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 3 (HCDR3); and three LCDRs comprising amino acid sequences of SEQ ID NO: 4 (LCDR1), SEQ ID NO: 5 (LCDR2), and SEQ ID NO: 23 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 39, and a light chain variable region comprising an amino acid sequence of SEQ ID NO: 40. In some embodiments, the anti-TIGIT antibody or antigen-binding fragment comprises the heavy chain variable region amino acid sequence of SEQ ID NO: 39 and the light chain variable region amino acid sequence of SEQ ID NO: 40, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 39, and a light chain variable region that is at least 90% identical to an amino acid sequence of SEQ ID NO: 40. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 39; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 40. In some embodiments, the anti-TIGIT antibody or antigen-binding fragment thereof comprises the paired set of heavy and light chain variable regions of 1A11, or the set of six CDR sequences from the paired heavy and light chain set of 1A11.

An exemplary anti-TIGIT antibody or antigen-binding fragment described herein comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the antibody or antigen-binding fragment comprises human germline heavy and light chain framework regions, or human germline heavy and light chain framework regions mutated to comprise one or more amino acid substitutions. In some embodiments, the antibody or antigen-binding fragment comprises a heavy chain variable region that is at least 90%, at least 91%, at least 92%, at least 93%, at least 94%, at least 95%, at least 96%, at least 97%, at least 98%, at least 99%, or 100% identical to an amino acid sequence of SEQ ID NO: 39, and a light chain variable region that is at least 90%, at least 91%, at least 92%, at least 93%, at least 94%, at least 95%, at least 96%, at least 97%, at least 98%, at least 99%, or 100% identical to an amino acid sequence of SEQ ID NO: 40. In some embodiments, the antibody or antigen-binding fragment comprises a heavy chain variable region comprising an amino acid sequence of SEQ ID NO: 39, and a light chain variable region comprising an amino acid sequence of SEQ ID NO: 40.

In some embodiments, the antibody or antigen-binding fragment comprises a heavy chain comprising an amino acid sequence of SEQ ID NO: 46, and a light chain comprising an amino acid sequence of SEQ ID NO: 48. In some embodiments, the antibody or antigen-binding fragment comprises a heavy chain that is at least 90% identical to an amino acid sequence of SEQ ID NO: 46, and a light chain that is at least 90% identical to an amino acid sequence of SEQ ID NO: 48. In some embodiments, the antibody or antigen-binding fragment comprises a heavy chain amino acid sequence that is at least 90%, at least 91%, at least 92%, at least 93%, at least 94%, at least 95%, at least 96%, at least 97%, at least 98%, at least 99%, or 100% identical to SEQ ID NO: 46; and/or a light chain amino acid sequence that is at least 90%, at least 91%, at least 92%, at least 93%, at least 94%, at least 95%, at least 96%, at least 97%, at least 98%, at least 99%, or 100% identical to SEQ ID NO: 48. In some embodiments, the heavy chain further comprises a C-terminal lysine (K).

In some embodiments, the antibody or antigen-binding fragment comprises a heavy chain comprising an amino acid sequence of SEQ ID NO: 47, and a light chain comprising an amino acid sequence of SEQ ID NO: 48. In some embodiments, the antibody or antigen-binding fragment comprises a heavy chain that is at least 90% identical to an amino acid sequence of SEQ ID NO: 47, and a light chain that is at least 90% identical to an amino acid sequence of SEQ ID NO: 48. In some embodiments, the antibody or antigen-binding fragment comprises a heavy chain amino acid sequence that is at least 90%, at least 91%, at least 92%, at least 93%, at least 94%, at least 95%, at least 96%, at least 97%, at least 98%, at least 99%, or 100% identical to SEQ ID NO: 47; and/or a light chain amino acid sequence that is at least 90%, at least 91%, at least 92%, at least 93%, at least 94%, at least 95%, at least 96%, at least 97%, at least 98%, at least 99%, or 100% identical to SEQ ID NO: 48. In some embodiments, the heavy chain further comprises a C-terminal lysine (K).

An exemplary anti-TIGIT antibody or antigen-binding fragment described herein comprises a heavy chain constant region comprising an amino acid sequence of SEQ ID NO: 44, and a light chain constant region comprising an amino acid sequence of SEQ ID NO: 45. In some embodiments, the antibody or antigen-binding fragment comprises a heavy chain comprising an amino acid sequence of SEQ ID NO: 47, and a light chain comprising an amino acid sequence of SEQ ID NO: 48. In some embodiments, the heavy chain constant region or heavy chain further comprises a C-terminal lysine (K). In some embodiments, the anti-TIGIT antibody or antigen-binding fragment thereof is 1A11.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 3 (HCDR3); and three LCDRs comprising amino acid sequences of SEQ ID NO: 4 (LCDR1), SEQ ID NO: 5 (LCDR2), and SEQ ID NO: 24 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 41, and a light chain variable region comprising an amino acid sequence of SEQ ID NO: 42. In some embodiments, the anti-TIGIT antibody or antigen-binding fragment comprises the heavy chain variable region amino acid sequence of SEQ ID NO: 41 and the light chain variable region amino acid sequence of SEQ ID NO: 42, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 41, and a light chain variable region that is at least 90% identical to an amino acid sequence of SEQ ID NO: 42. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 41; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 42. In some embodiments, the anti-TIGIT antibody or antigen-binding fragment thereof comprises the paired set of heavy and light chain variable regions of 1E3, or the set of six CDR sequences from the paired heavy and light chain set of 1E3. In some embodiments, the anti-TIGIT antibody or antigen-binding fragment thereof is 1E3.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 3 (HCDR3); and three LCDRs comprising amino acid sequences of SEQ ID NO: 4 (LCDR1), SEQ ID NO: 5 (LCDR2), and SEQ ID NO: 6 (LCDR3).

In some embodiments, the anti-TIGIT antibody or antigen-binding fragment comprises a heavy chain variable region comprising an amino acid sequence of SEQ ID NO: 25, and a light chain variable region comprising an amino acid sequence of SEQ ID NO: 26. In some embodiments, the anti-TIGIT antibody or antigen-binding fragment comprises the heavy chain variable region amino acid sequence of SEQ ID NO: 25 and the light chain variable region amino acid sequence of SEQ ID NO: 26, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 25, and a light chain variable region that is at least 90% identical to an amino acid sequence of SEQ ID NO: 26. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 25; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 26. In some embodiments, the anti-TIGIT antibody or antigen-binding fragment thereof comprises the paired set of heavy and light chain variable regions of 7D4, or the set of six CDR sequences from the paired heavy and light chain set of 7D4. In some embodiments, the anti-TIGIT antibody or antigen-binding fragment thereof is 7D4.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 3 (HCDR3); and three LCDRs comprising amino acid sequences of SEQ ID NO: 4 (LCDR1), SEQ ID NO: 5 (LCDR2), and SEQ ID NO: 6 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 31, and a light chain variable region comprising an amino acid sequence of SEQ ID NO: 32. In some embodiments, the anti-TIGIT antibody or antigen-binding fragment comprises the heavy chain variable region amino acid sequence of SEQ ID NO: 31 and the light chain variable region amino acid sequence of SEQ ID NO: 32, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 31, and a light chain variable region that is at least 90% identical to an amino acid sequence of SEQ ID NO: 32. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 31; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 32. In some embodiments, the anti-TIGIT antibody or antigen-binding fragment thereof comprises the paired set of heavy and light chain variable regions of hz7D4, or the set of six CDR sequences from the paired heavy and light chain set of hz7D4. In some embodiments, the anti-TIGIT antibody or antigen-binding fragment thereof is hz7D4.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 19 (HCDR3); and three LCDRs comprising amino acid sequences of SEQ ID NO: 4 (LCDR1), SEQ ID NO: 5 (LCDR2), and SEQ ID NO: 6 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 33, and a light chain variable region comprising an amino acid sequence of SEQ ID NO: 34. In some embodiments, the anti-TIGIT antibody or antigen-binding fragment comprises the heavy chain variable region amino acid sequence of SEQ ID NO: 33 and the light chain variable region amino acid sequence of SEQ ID NO:

34, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 33, and a light chain variable region that is at least 90% identical to an amino acid sequence of SEQ ID NO: 34. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 33; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 34. In some embodiments, the anti-TIGIT antibody or antigen-binding fragment thereof comprises the paired set of heavy and light chain variable regions of 1G3, or the set of six CDR sequences from the paired heavy and light chain set of 1G3. In some embodiments, the anti-TIGIT antibody or antigen-binding fragment thereof is 1G3.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 20 (HCDR3); and three LCDRs comprising amino acid sequences of SEQ ID NO: 4 (LCDR1), SEQ ID NO: 5 (LCDR2), and SEQ ID NO: 6 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 35, and a light chain variable region comprising an amino acid sequence of SEQ ID NO: 36. In some embodiments, the anti-TIGIT antibody or antigen-binding fragment comprises the heavy chain variable region amino acid sequence of SEQ ID NO: 35 and the light chain variable region amino acid sequence of SEQ ID NO: 36, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 35, and a light chain variable region that is at least 90% identical to an amino acid sequence of SEQ ID NO: 36. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 35; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 36. In some embodiments, the anti-TIGIT antibody or antigen-binding fragment thereof comprises the paired set of heavy and light chain variable regions of 2F1, or the set of six CDR sequences from the paired heavy and light chain set of 2F1. In some embodiments, the anti-TIGIT antibody or antigen-binding fragment thereof is 2F1.

In some embodiments, an anti-TIGIT antibody or antigen-binding fragment thereof comprises three HCDRs comprising amino acid sequences of SEQ ID NO: 1 (HCDR1), SEQ ID NO: 2 (HCDR2), and SEQ ID NO: 21 (HCDR3); and three LCDRs comprising amino acid sequences of SEQ ID NO: 4 (LCDR1), SEQ ID NO: 5 (LCDR2), and SEQ ID NO: 6 (LCDR3).

In some embodiments, the anti-TIGIT antibody or antigen-binding fragment comprises human germline heavy and light chain framework regions, or human germline heavy and light chain framework regions mutated to comprise one or more amino acid substitutions. In some embodiments, the anti-TIGIT antibody or antigen-binding fragment comprises a heavy chain variable region comprising an amino acid sequence of SEQ ID NO: 37, and a light chain variable region comprising an amino acid sequence of SEQ ID NO: 38. In some embodiments, the anti-TIGIT antibody or antigen-binding fragment comprises the heavy chain variable region amino acid sequence of SEQ ID NO: 37 and the light chain variable region amino acid sequence of SEQ ID NO: 38, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 37, and a light chain variable region that is at least 90% identical to an amino acid sequence of SEQ ID NO: 38. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 37; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 38. In some embodiments, the anti-TIGIT antibody or antigen-binding fragment thereof comprises the paired set of heavy and light chain variable regions of 3H2, or the set of six CDR sequences from the paired heavy and light chain set of 3H2. In some embodiments, the anti-TIGIT antibody or antigen-binding fragment thereof is 3H2.

In some embodiments, an anti-TIGIT antibody or antigen-binding fragment thereof comprises three HCDRs comprising amino acid sequences of SEQ ID NO: 7 (HCDR1), SEQ ID NO: 8 (HCDR2), and SEQ ID NO: 9 (HCDR3); and three LCDRs comprising amino acid sequences of SEQ ID NO: 10 (LCDR1), SEQ ID NO: 11 (LCDR2), and SEQ ID NO: 12 (LCDR3).

In some embodiments, the anti-TIGIT antibody or antigen-binding fragment comprises a heavy chain variable region comprising an amino acid sequence of SEQ ID NO: 27, and a light chain variable region comprising an amino acid sequence of SEQ ID NO: 28. In some embodiments, the anti-TIGIT antibody or antigen-binding fragment comprises the heavy chain variable region amino acid sequence of SEQ ID NO: 27 and the light chain variable region amino acid sequence of SEQ ID NO: 28, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 27, and a light chain variable region that is at least 90% identical to an amino acid sequence of SEQ ID NO: 28. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 27; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 28. In some embodiments, the anti-TIGIT antibody or antigen-binding fragment thereof comprises the paired set of heavy and light chain variable regions of 2C9, or the set of six CDR sequences from the paired heavy and light chain set of 2C9. In some embodiments, the anti-TIGIT antibody or antigen-binding fragment thereof is 2C9.

In some embodiments, an anti-TIGIT antibody or antigen-binding fragment thereof comprises three HCDRs comprising amino acid sequences of SEQ ID NO: 13 (HCDR1), SEQ ID NO: 14 (HCDR2), and SEQ ID NO: 15 (HCDR3); and three LCDRs comprising amino acid sequences of SEQ ID NO: 16 (LCDR1), SEQ ID NO: 17 (LCDR2), and SEQ ID NO: 18 (LCDR3).

In some embodiments, the anti-TIGIT antibody or antigen-binding fragment comprises a heavy chain variable region comprising an amino acid sequence of SEQ ID NO: 29, and a light chain variable region comprising an amino acid sequence of SEQ ID NO: 30. In some embodiments, the anti-TIGIT antibody or antigen-binding fragment comprises the heavy chain variable region amino acid sequence of SEQ ID NO: 29 and the light chain variable region amino acid sequence of SEQ ID NO: 30, or sequences that are at least 90% identical to the disclosed sequences. In some embodiments, the anti-TIGIT antibody or antigen-binding fragment comprises a heavy chain variable region that is at least 90% identical to an amino acid sequence of SEQ ID NO: 29, and a light chain variable region that is at least 90% identical to an amino acid sequence of SEQ ID NO: 30. In some embodiments, the anti-TIGIT antibody or antigen-binding fragment comprises a heavy chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 29; and/or a light chain variable region amino acid sequence that is at least 90%, at least 91%, at least 92%, at least 93%, at least 94%, at least 95%, at least 96%, at least 97%, at least 98%, at least 99%, or 100% identical to SEQ ID NO: 30. In some embodiments, the anti-TIGIT antibody or antigen-binding fragment thereof comprises the paired set of heavy and light chain variable regions of 3A9, or the set of six CDR sequences from the paired heavy and light chain set of 3A9. In some embodiments, the anti-TIGIT antibody or antigen-binding fragment thereof is 3A9.

In some embodiments, an anti-TIGIT antibody or antigen-binding fragment described herein (e.g., any of the exemplary antibodies or antigen-binding fragments discussed above) comprises an IgG1 heavy chain constant region, or an IgG1 heavy chain constant region mutated to modify effector function. In some embodiments, the heavy chain constant region is a human IgG1 heavy chain constant region. In some embodiments, the anti-TIGIT antibody or antigen-binding fragment comprises a heavy chain constant region comprising an amino acid sequence of SEQ ID NO: 43. In some embodiments, the anti-TIGIT antibody or antigen-binding fragment comprises a heavy chain constant region comprising an amino acid sequence of SEQ ID NO: 43 mutated to comprise amino acid substitutions at positions 239, 330, and 332. In some embodiments, the S at position 239 of SEQ ID NO: 43 is substituted with D; the A at position 330 of SEQ ID NO: 43 is substituted with L; and the I at position 332 of SEQ ID NO: 43 is substituted with E. In some embodiments, the anti-TIGIT antibody or antigen-binding fragment comprises a heavy chain constant region comprising an amino acid sequence of SEQ ID NO: 44. In some embodiments, the heavy chain constant region further comprises a C-terminal lysine (K).

In some embodiments, an anti-TIGIT antibody or antigen-binding fragment described herein (e.g., any of the exemplary antibodies or antigen-binding fragments discussed above) comprises an IgG2 (e.g., IgG2a, IgG2b), IgG3, or IgG4 heavy chain constant region, or an IgG2 (e.g., IgG2a, IgG2b), IgG3, or IgG4 heavy chain constant region mutated to modify effector function. In some embodiments, the heavy chain constant region is a human IgG2 (e.g, IgG2a, IgG2b), IgG3, or IgG4 heavy chain constant region.

In some embodiments, an anti-TIGIT antibody or antibody or antigen-binding fragment described herein (e.g., any of the exemplary antibodies or antigen-binding fragments discussed above) comprises an Ig kappa light chain constant region. In some embodiments, the Ig kappa light chain constant region is a human Ig kappa light chain constant region. In some embodiments, the anti-TIGIT antibody or antigen-binding fragment comprises a light chain constant region comprising an amino acid sequence of SEQ ID NO: 45.

In some embodiments, an anti-TIGIT antibody or antibody or antigen-binding fragment described herein (e.g., any of the exemplary antibodies or antigen-binding fragments discussed above) comprises an Ig lambda light chain constant region. In some embodiments, the Ig lambda light chain constant region is a human Ig lambda light chain constant region.

In some embodiments, an antibody or antigen-binding fragment disclosed herein specifically binds to human TIGIT, wherein the antibody or antigen-binding fragment binds to a region of human TIGIT comprising the Y at position 106 of SEQ ID NO: 22. In some embodiments, the region further comprises one or more of: the Q at position 56 of SEQ ID NO: 22; the G at position 74 of SEQ ID NO: 22; the Y at position 110 of SEQ ID NO: 22; and the H at position 111 of SEQ ID NO: 22. In some embodiments, the region further comprises the Q at position 56 of SEQ ID NO: 22. In some embodiments, the region further comprises the G at position 74 of SEQ ID NO: 22. In some embodiments, the region further comprises the Y at position 110 of SEQ ID NO: 22. In some embodiments, the region further comprises the H at position 111 of SEQ ID NO: 22. In some embodiments, the region comprises all of: the Q at position 56 of SEQ ID NO: 22; the G at position 74 of SEQ ID NO: 22; the Y at position 106 of SEQ ID NO: 22; the Y at position 110 of SEQ ID NO: 22; and the H at position 111 of SEQ ID NO: 22.

In some embodiments, the region comprises at least: the Q at position 56 of SEQ ID NO: 22; and the Y at position 106 of SEQ ID NO: 22. In some embodiments, the region comprises at least: the Q at position 56 of SEQ ID NO: 22; the G at position 74 of SEQ ID NO: 22; the Y at position 106 of SEQ ID NO: 22; and the Y at position 110 of SEQ ID NO: 22. In some embodiments, the region is non-linear.

In some embodiments, the antibody or antigen-binding fragment competes for binding to human TIGIT with a reference antibody or antigen-binding fragment, wherein the reference antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the antibody or antigen-binding fragment binds to the same region of human TIGIT as a reference antibody or antigen-binding fragment, wherein the reference antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3). In some embodiments, the reference antibody or antigen-binding fragment comprises human germline heavy and light chain framework regions, or human germline heavy and light chain framework regions mutated to comprise one or more amino acid substitutions. In some embodiments, the reference antibody or antigen-binding fragment comprises a heavy chain variable region comprising an amino acid sequence of SEQ ID NO: 39, and a light chain variable region comprising an amino acid sequence of SEQ ID NO: 40. In some embodiments, the reference antibody or antigen-binding fragment comprises a heavy chain constant region comprising an amino acid sequence of SEQ ID NO: 44, and a light chain constant region comprising an amino acid sequence of SEQ ID NO: 45. In some embodiments, the reference antibody or antigen-binding fragment comprises a heavy chain comprising an amino acid sequence of SEQ ID NO: 47, and a light chain comprising an amino acid sequence of SEQ ID NO: 48. In some embodiments, the heavy chain constant region or heavy chain further comprises a C-terminal lysine (K). In some embodiments, the reference antibody or antigen-binding fragment is 1A11. In some embodiments, the reference antibody or antigen-binding fragment is another exemplary antibody or antigen-binding fragment disclosed herein.

The antibodies and antigen-binding fragments disclosed herein may include further modifications (e.g., one or more amino acid substitutions, deletions, and/or insertions) while maintaining the ability to bind to TIGIT. In some embodiments, an antibody or antigen-binding fragment comprises specified modifications (e.g., relative to a reference sequence) and, optionally, comprises about 1 to 10 amino acid modifications, such as 1, 2, 3, 4, 5, 6, 7, 8, 9, or 10 amino acid modifications in addition to the specified modifications. In some embodiments, an antibody or antigen-binding fragment comprises a heavy chain variable region comprising up to about 2, up to about 5, or up to about 10 amino acid modifications in addition to any specified amino acid modifications. In some embodiments, an antibody or antigen-binding fragment comprises a heavy chain constant region comprising up to about 2, up to about 5, or up to about 10 amino acid modifications in addition to any specified amino acid modifications. In some embodiments, an antibody or antigen-binding fragment comprises a light chain variable region comprising up to about 2, up to about 5, or up to about 10 amino acid modifications in addition to any specified amino acid modifications. In some embodiments, an antibody or antigen-binding fragment comprises a light chain constant region comprising up to about 2, up to about 5, or up to about 10 amino acid modifications in addition to any specified amino acid modifications.

In some embodiments, amino acid substitutions are of single residues. Insertions usually will be on the order of from about 1 to about 20 amino acid residues, although considerably larger insertions may be tolerated as long as biological function is retained (e.g., binding to TIGIT). Deletions usually range from about 1 to about 20 amino acid residues, although in some cases deletions may be much larger as long as biological function is retained (e.g., binding to TIGIT). Substitutions, deletions, insertions, or any combination thereof may be used to arrive at a final derivative or variant. Generally, these changes are done on as few amino acids as possible to minimize the alteration of the molecule, particularly the immunogenicity and specificity of the antigen-binding protein. However, larger changes may be tolerated in certain circumstances as long as biological function is retained (e.g., binding to TIGIT). Conservative substitutions are generally made in accordance with tables providing functionally similar amino acids, such as the exemplary table depicted below as Table 6 and others are known in the art.

TABLE 6

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

In some embodiments, substantial changes in function or immunological identity may be made by selecting substitutions that are less conservative than those shown in Table 6. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general may produce the greatest changes in the properties of a polypeptide are those in which (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine.

In some embodiments where variant antibody sequences are used in an antibody or antigen-binding fragment, the variants typically exhibit the same qualitative biological activity and will elicit the same immune response, although variants may also be selected to modify the characteristics of the antigen-binding proteins as needed. Furthermore, an antibody of the disclosure may, in some embodiments, be chemically modified (e.g., one or more chemical moieties can be attached to the antibody) or be modified to alter its glycosylation, e.g., to alter one or more functional properties of the antibody or antigen-binding fragment.

Alterations (e.g., substitutions) may be made within the framework or CDR regions, e.g., to maintain or improve antibody affinity. Such alterations may be made in "hotspots," i.e., residues encoded by codons that undergo mutation at high frequency during the somatic maturation process (see, e.g., Chowdhury (2008) Methods Mol. Biol. 207:179-96), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. HCDR3 and LCDR3 in particular are often targeted. Exemplary methods for affinity maturation are described in the examples herein (see, e.g., Examples 13, 14, and 17).

In addition to modifications made within the framework or CDR regions, an antibody of the disclosure may be engineered to include modifications within the Fc region, typically to alter one or more functional properties of the antibody or antigen-binding fragment, such as serum half-life, complement fixation, Fc receptor binding, and/or antigen-dependent cellular cytotoxicity. Such antibodies are described and exemplified herein. In some embodiments, one or more amino acid modifications are introduced into the Fc region of an antibody or antigen-binding fragment of the disclosure, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions. Amino acid positions within the Fc region may be described, e.g., using the EU numbering system (Kabat et al. "Sequences of Proteins of Immunological Interest," U.S. Department of Health and Human Services, U.S. Government Printing Office (1991)). In some embodiments, such a variant comprises an Fc region with one or more amino acid substitutions to modify effector function, e.g., to improve or enhance ADCC, e.g., substitutions at positions 239, 330, and/or 332 of the Fc region (EU numbering of residues) (see, e.g., Lazar et al. (2006) Proc Natl Acad Sci USA 103(11):4005-10).

Amino acid substitutions described herein may be indicated by listing the absolute residue position followed by the three-letter or one-letter code for the substituted (i.e., replacement) amino acid. For example, the substitution of an aspartic acid for the serine at position 239 of SEQ ID NO: 43 (EU numbering of residues) may be expressed as "Ser239Asp" or "S239D." In this example, serine is the amino acid being replaced (or the "replaced" amino acid), and aspartic acid is the amino acid being substituted for serine (or the "replacement" amino acid).

In some embodiments, an antibody or antigen-binding fragment described herein is capable of binding to human TIGIT, cynomolgus monkey (cyno) TIGIT, and/or mouse TIGIT. In some embodiments, an antibody or antigen-binding fragment described herein is capable of binding to mouse TIGIT, in addition to human TIGIT. In some embodiments, an antibody or antigen-binding fragment described herein is capable of binding to cyno TIGIT, in addition to human TIGIT. In some embodiments, an antibody or antigen-binding fragment described herein is capable of binding to human TIGIT, but not mouse or cyno TIGIT. In some embodiments, an antibody or antigen-binding fragment described herein is capable of binding to human TIGIT, cyno TIGIT, and mouse TIGIT.

In some embodiments, an antibody or antigen-binding fragment disclosed herein may be useful alone (e.g., as an antibody or antigen-binding fragment), linked to one or more additional agents (e.g., as an antibody-drug conjugate), or as part of a larger macromolecule (e.g., a bispecific antibody or multispecific antibody). For instance, in some embodiments, the antibody or antigen-binding fragment is an antigen-binding domain in and/or is part of a bispecific or multispecific antibody. In some embodiments, an antigen-binding domain is an antigen-binding fragment. In some embodiments, the antigen-binding domain and/or antigen-binding fragment is a single chain variable fragment (scFv) or a Fab fragment. In some embodiments, the antibodies and antigen-binding fragments disclosed herein, for use alone or as part of a larger macromolecule, may include further modifications (e.g., one or more amino acid substitutions, deletions, and/or insertions) while retaining TIGIT-binding function.

In some embodiments, the present disclosure provides isolated and/or substantially purified nucleic acid molecules (also referred to as polynucleotides) which encode full-length polypeptides or polypeptides comprising segments of the antibodies and antigen-binding fragments described herein. In some embodiments, a single nucleic acid may comprise both the coding sequence for a heavy chain variable region and a light chain variable region, and optionally also comprise coding sequences for one or more constant regions, of an antibody or antigen-binding fragment disclosed herein. Alternatively, some or all of these coding sequences may reside on separate nucleic acid molecules. When expressed from appropriate expression vectors, polypeptides encoded by these polynucleotides are capable of binding to TIGIT (e.g., human TIGIT).

Also provided herein are polynucleotides which encode at least one CDR region, and usually all three CDR regions, from the heavy and/or light chain of an exemplary anti-TIGIT antibody or antigen-binding fragment of the disclosure. Further provided herein are polynucleotides which encode all or substantially all of the variable region sequence of the heavy chain and/or the light chain of an exemplary anti-TIGIT antibody or antigen-binding fragment of the disclosure. Because of the degeneracy of the genetic code, a variety of nucleic acid sequences will encode each of the exemplary amino acid sequences disclosed herein.

Also provided herein are expression vectors, host cells, and methods for producing the anti-TIGIT antibodies and antigen-binding fragments of the disclosure.

In some embodiments, the present disclosure provides an isolated nucleic acid encoding an antibody or antigen-binding fragment disclosed herein. In some embodiments, the present disclosure provides an isolated vector comprising an isolated nucleic acid encoding an antibody or antigen-binding fragment disclosed herein. In some embodiments, the present disclosure provides an isolated cell or cell population comprising an isolated nucleic acid, or a vector comprising an isolated nucleic acid, encoding an antibody or antigen-binding fragment disclosed herein. In some embodiments, the present disclosure provides a method of producing an antibody or antigen-binding fragment by culturing a host cell or cell population modified to comprise one or more nucleic acid sequences encoding an antibody or antigen-binding fragment described herein under conditions suitable to produce the antibody or antigen-binding fragment. In some embodiments, the method further comprises a step of isolating, purifying, and/or recovering the produced antibody or antigen-binding fragment.

The term "vector" is intended to refer to a polynucleotide molecule capable of transporting and/or controlling the expression of another polynucleotide to which it has been linked. One type of vector is a "plasmid," which refers to a circular double-stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors can direct the expression of genes to which they are operatively linked. Such vectors are referred to herein as "expression vectors" or "recombinant expression vectors." In general, expression vectors of utility in recombinant DNA techniques are often in the form of plasmids. The present disclosure is intended to include plasmids, as well as other forms of expression vectors, such as viral vectors (e.g., replication defective retroviruses or lentiviruses, adenoviruses, and adeno-associated viruses), which serve equivalent functions.

Vectors to be used to receive sequences encoding anti-TIGIT antibody heavy and/or light chain variable regions or antigen-binding fragments thereof sometimes also encode constant regions or parts thereof. Such vectors allow expression of the variable regions or fragments thereof as fusion proteins with the constant regions, thereby leading to production of full-length antibodies or antigen-binding fragments thereof. In some embodiments, such constant regions are human. In some embodiments, the constant region is a human IgG1 heavy chain constant region. In some embodiments, the constant region is a human Ig kappa light chain constant region. In other embodiments, the constant region is a mouse IgG2 (e.g., IgG2a) heavy chain constant region. In some embodiments, the constant region is a mouse Ig kappa light chain constant region.

The term "host cell" refers to a cell (or cell population) artificially engineered to comprise nucleic acids encoding the sequence of a peptide and which will transcribe and translate, and optionally, secrete the peptide into the cell growth medium. For recombinant production purposes, a nucleic acid encoding the amino acid sequence of the peptide would typically be synthesized or cloned by conventional methods and integrated into an expression vector. The term "host cell" refers not only to the particular subject cell but to the progeny of such a cell. Because certain modifications may occur in succeeding generations due to either mutation or environmental influences, such progeny may not, in fact, be identical to the parent cell, but are still included within the scope of the term as used herein.

The host cells for harboring and expressing nucleic acids encoding anti-TIGIT antibody chains or antigen-binding fragments can be either prokaryotic or eukaryotic. In some embodiments, mammalian host cells are used to express and produce the anti-TIGIT polypeptides of the disclosure. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various COS cell lines, HeLa cells, myeloma cell lines, transformed B cells, and hybridomas. Exemplary host cells include but are not limited to Chinese hamster ovary (CHO) cells (e.g., CHO-S), human embryonic kidney (HEK) cells (e.g., 293T), monkey kidney (COS) cells (e.g., COS-1, COS-7), baby hamster kidney (BHK) cells (e.g., BHK-21), African green monkey kidney cells (e.g. BSC-1), HeLa cells, human hepatocellular carcinoma cells (e.g., Hep G2), myeloma cells (e.g., NS0, 653, SP2/0), and lymphoma cells, or any derivative, immortalized, or transformed cell thereof. In some embodiments, a host cell or cell population comprises one or more CHO cells (e.g., CHO-S). In some embodiments, a host cell or cell population comprises one or more myeloma cells (e.g., NS0).

In some embodiments, one or more nucleic acid molecules encoding the heavy and/or light chains of an anti-TIGIT antibody or antigen-binding fragment, or one or more expression vectors comprising such nucleic acid molecules, can be introduced into a suitable host cell (e.g., one or more CHO-S cells or one or more NS0 cells) to create a recombinant host cell using any method appropriate to the host cell selected (e.g., transformation, transfection, electroporation, infection), such that the nucleic acid molecules are operably linked to one or more expression control elements (e.g., in a vector, in a construct created by processes in the cell, or integrated into the host cell genome). In some embodiments, the resulting recombinant host cell can be maintained under conditions suitable for expression or production (e.g., in the presence of an inducer, in a suitable non-human animal, or in suitable culture media supplemented with appropriate salts, growth factors, antibiotics, nutritional supplements, etc.), whereby the encoded polypeptides are produced. If desired, the encoded protein can be isolated or recovered (e.g., from the animal, the host cell, or medium). This process encompasses expression in a host cell of a transgenic non-human animal (see, e.g., Intl. Pub. No. WO 1992/003918). Further, expression of antibody chains or antigen-binding fragments thereof from production cell lines can be enhanced using known techniques. For example, the glutamine synthetase and DHFR gene expression systems are common approaches for enhancing expression under certain conditions. High expressing cell clones can be identified using conventional techniques, such as limited dilution cloning, gel micro-drop technology, or any other methods known in the art.

Pharmaceutical Compositions

In some embodiments, the present disclosure provides pharmaceutical compositions comprising one or more antibodies and/or one or more antigen-binding fragments disclosed herein and at least one pharmaceutically acceptable carrier.

Suitable carriers include any material that, when combined with the therapeutic composition, retains the function of the therapeutic composition and is generally non-reactive with a patient's immune system. Pharmaceutically acceptable carriers include any and all solvents, dispersion media, coatings, antibacterial and antifungal agents, isotonic and absorption delaying agents, and the like that are physiologically compatible. Examples of pharmaceutically acceptable carriers include one or more of water, saline, phosphate-buffered saline (PBS), histidine, dextrose, glycerol, ethanol, mesylate salt, and the like, as well as combinations thereof. In some embodiments, isotonic agents, for example, sugars, polyalcohols such as mannitol, sorbitol, or sodium chloride, are included in the composition. Pharmaceutically acceptable carriers may further comprise minor amounts of auxiliary substances such as wetting or emulsifying agents, preservatives, or buffers, which enhance the shelf life or effectiveness of the antibody or antigen-binding fragment.

In some embodiments, the pharmaceutical compositions described herein comprise multiple copies of an antibody or antigen-binding fragment. In some embodiments, the pharmaceutical compositions described herein comprise at least one additional agent. In some embodiments, a pharmaceutical composition may comprise one or more additional therapeutic agents, e.g., one or more agents capable of treating or delaying the progression of an immune-related disease (e.g., a cancer or an infection or infectious disease). Non-limiting examples of such therapeutic agents include checkpoint inhibitors, such as checkpoint inhibitors targeted at PD-1, PD-L1, CTLA-4, OX40, CD40, LAG3, TIM3, GITR, and/or KIR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule. In some embodiments, the checkpoint inhibitor is targeted at PD-1 and/or PD-L1.

Therapeutic Uses and Compositions

The antibodies, antigen-binding fragments, and/or pharmaceutical compositions disclosed herein may be employed in various therapeutic applications. Disclosed herein are methods of using the disclosed antibodies, antigen-binding fragments, and/or pharmaceutical compositions in treating a subject for an immune-related disease (e.g., a cancer or an infection or infectious disease). The antibodies and/or antigen-binding fragments may be administered alone or in combination with one or more additional therapeutic agents, and may be administered in any pharmaceutically acceptable formulation, dosage, and dosing regimen. The antibody or antigen-binding fragment treatments described herein may be evaluated for toxicity as well as indicators of efficacy and adjusted accordingly.

In some embodiments, provided herein are therapeutic methods and uses for the described antibodies and/or antigen-binding fragments, e.g., in activating and/or killing one or more immune cells. In some embodiments, the therapeutic methods and uses described herein are useful for increasing, enhancing, or stimulating an immune response or function in a subject. In some embodiments, at least one immune response or function is increased, enhanced, and/or stimulated, e.g., by activating effector cells (e.g., T cells), expanding an effector cell population, and/or killing target cells (e.g., target tumor cells) in the subject as a result of treatment with an antibody or antigen-binding fragment of the disclosure.

In some embodiments, one or more immune cells (e.g., T or NK cells, e.g., cytotoxic T cells) in a subject treated with an antibody, antigen-binding fragment, and/or composition of the disclosure have one or more increased or enhanced properties, such as priming, activation, proliferation, cytokine release and/or cytolytic activity, as compared to these properties before treatment. In some embodiments, the number of immune cells (e.g., T or NK cells, e.g., cytotoxic T cells) in a subject treated with an antibody, antigen-binding fragment, and/or composition of the disclosure is elevated as compared to the number before treatment. In some embodiments, the number of activated immune cells (e.g., activated T or NK cells, e.g., activated cytotoxic T cells) in a subject treated with an antibody, antigen-binding fragment, and/or composition of the disclosure is elevated as compared to the number before treatment. In some embodiments, activated immune cells may be characterized by IFN-γ producing CD4+ and/or CD8+ T cells and/or enhanced cytolytic activity as compared to the activity before treatment. In some embodiments, activated immune cells may exhibit increased release of cytokines (e.g., IFN-γ, TNF-α, and interleukins (e.g., IL-2)) as compared to the release before treatment.

In some embodiments, the present disclosure provides a method of activating and/or killing one or more immune cells in a subject in need thereof, comprising administering to the subject an effective amount of an antibody or antigen-binding fragment described herein, or a pharmaceutical composition described herein. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides an antibody or antigen-binding fragment described herein, or a pharmaceutical composition described herein, for use in activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein, or a pharmaceutical composition described herein, for activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein in the manufacture of a medicament for activating and/or killing one or more immune cells in a subject in need thereof. In some embodiments, activating one or more immune cells comprises activating one or more natural killer cells, one or more cytotoxic T cells, one or more helper T cells, and/or one or more monocyte cells. In some embodiments, the one or more immune cells comprise one or more natural killer cells and/or one or more cytotoxic T cells. In some embodiments, killing one or more immune cells comprises killing one or more regulatory T cells. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, provided herein are therapeutic methods and uses for the described antibodies and/or antigen-binding fragments, e.g., in treating a cancer. A variety of cancers may be treated and/or their progression may be delayed. In some embodiments, the cancer is a colorectal cancer or leukemia. The cancer (e.g., colorectal cancer) may be at an early, intermediate, or late stage.

In some embodiments, the present disclosure provides a method of treating a cancer in a subject in need thereof, comprising administering to the subject a therapeutically effective amount of an antibody or antigen-binding fragment described herein, or a pharmaceutical composition described herein. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides an antibody or antigen-binding fragment described herein, or a pharmaceutical composition described herein, for use in treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein, or a pharmaceutical composition described herein, for treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein in the manufacture of a medicament for treating a cancer in a subject in need thereof. In some embodiments, the cancer expresses CD155. In some embodiments, the cancer is a solid tumor. In some embodiments, the cancer is a colorectal cancer or leukemia. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, provided herein are therapeutic methods and uses for the described antibodies and/or antigen-binding fragments, e.g., in treating an infection or infectious disease. In some embodiments, the infection or infectious disease is an acute or chronic infection (e.g., an acute or chronic viral infection). In some embodiments, the infection or infectious disease is a retroviral infection, e.g., a retroviral infection affecting T cells, e.g., a human T cell leukemia virus type 1-associated disease. In some embodiments, the infection or infectious disease is a human T cell leukemia virus type 1-associated disease.

In some embodiments, the present disclosure provides a method of treating an infection or infectious disease in a subject in need thereof, comprising administering to the subject a therapeutically effective amount of an antibody or antigen-binding fragment described herein, or a pharmaceutical composition described herein. In some embodiments, the infection or infectious disease is a human T cell leukemia virus type 1-associated disease. In some embodiments, the antibody or antigen-binding fragment or pharmaceutical composition is administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides an antibody or antigen-binding fragment described herein, or a pharmaceutical composition described herein, for use in treating an infection or infectious disease in a subject in need thereof. In some embodiments, the infection or infectious disease is a human T cell leukemia virus type 1-associated disease. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein, or a pharmaceutical composition described herein, for treating an infection or infectious disease in a subject in need thereof. In some embodiments, the infection or infectious disease is a human T cell leukemia virus type 1-associated disease. In some embodiments, the antibody or antigen-binding fragment or pharmaceutical composition is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

In some embodiments, the present disclosure provides a use of an antibody or antigen-binding fragment described herein in the manufacture of a medicament for treating an infection or infectious disease in a subject in need thereof. In some embodiments, the infection or infectious disease is a human T cell leukemia virus type 1-associated disease. In some embodiments, the antibody or antigen-binding fragment is to be administered in combination with at least one additional therapeutic agent. In some embodiments, the at least one additional therapeutic agent comprises a checkpoint inhibitor. In some embodiments, the checkpoint inhibitor is a PD-1 inhibitor. In some embodiments, the checkpoint inhibitor is an anti-PD-1 antagonist antibody. In some embodiments, the checkpoint inhibitor is pembrolizumab.

An anti-TIGIT antibody, antigen-binding fragment, and/or composition of the disclosure (and/or any additional therapeutic agent) may be administered by any suitable means, including parenteral, intrapulmonary, and intranasal, and, if desired for local treatment, intralesional administration. Exemplary parenteral administration routes include intramuscular, intravenous, intraarterial, intraperitoneal, and subcutaneous. Dosing can be by any suitable route, for example, by injections, such as intravenous or subcutaneous injections, depending in part on whether the administration is acute or chronic. Various dosing schedules including but not limited to single or multiple administrations over various time-points, bolus administration, and pulse infusion are contemplated herein. In some embodiments, an anti-TIGIT antibody, antigen-binding fragment, and/or composition of the disclosure is administered after the subject has been diagnosed with a disease, and before the disease has been cured or eliminated. In some embodiments, the subject is in the early stages of disease. In some embodiments, the subject is in the intermediate stages of disease. In some embodiments, the subject is in the late stages of disease. In some embodiments, an anti-TIGIT antibody, antigen-binding fragment, and/or composition of the disclosure is administered when a subject is identified as being at risk but before the subject has developed symptoms of the disease.

An anti-TIGIT antibody, antigen-binding fragment, and/or composition of the disclosure may be administered alone or in combination with at least one additional therapeutic agent (e.g., a checkpoint inhibitor, an anti-cancer agent, etc.). When administered in combination with an additional therapeutic agent, the additional therapeutic agent may be administered according to its standard dosage and/or dosing regimen. Alternatively, the additional therapeutic agent may be administered at a higher or lower amount and/or frequency, as compared to its standard dosage and/or dosing regimen. In some embodiments, the additional therapeutic agent is administered at a lower amount and/or frequency as compared to its standard dosage and/or dosing regimen.

Additional therapeutic agents (e.g., those which may be administered in combination with an anti-TIGIT antibody or antigen-binding fragment described herein) may comprise any active agents suitable for the particular indication being treated (e.g., a cancer or an infection or infectious disease), e.g., those with complementary activities that do not adversely affect each other. In some embodiments, an additional therapeutic agent is a checkpoint inhibitor, an immunomodulatory agent, a cytotoxic agent, or a cytostatic agent. In some embodiments, the additional therapeutic agent is a checkpoint inhibitor.

As discussed herein, checkpoint inhibitor treatment strategies are generally based on the hypothesis that treatment facilitates and/or enhances priming of T cell responses to weakly or poorly antigenic tumors (e.g., CTLA-4) or that treatment restores and/or reinvigorates T cells that respond to antigens, but have become "exhausted" due to the chronic nature of the antigen presentation (e.g., PD-1, PD-L1) (Chen and Mellman (2013) Immunity 39(1):1-10). Examples of suitable checkpoint inhibition therapies and agents, e.g., anti-PD-1, anti-PD-L1, and anti-CTLA-4 antibodies, are known in the art. See, e.g., WO 2001/014424. WO 2013/173223, WO 2016/007235.

In some embodiments, a checkpoint inhibitor (e.g., one which may be administered in combination with an anti-TIGIT antibody or antigen-binding fragment described herein) is an inhibitor of the cytotoxic T lymphocyte-associated antigen (CTLA-4) pathway. CTLA-4, also known as CD152, is a protein receptor that downregulates immune responses. CTLA-4 is constitutively expressed in regulatory T cells, but only upregulated in conventional T cells after activation. As used herein, the term "CTLA-4 inhibitor" is meant to refer to any inhibitor of CTLA-4 and/or the CTLA-4 pathway. Exemplary CTLA-4 inhibitors include but are not limited to anti-CTLA-4 antibodies. Exemplary anti-CTLA-4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the checkpoint inhibitor is ipilimumab. In some embodiments, the checkpoint inhibitor is tremelimumab.

In some embodiments, a checkpoint inhibitor (e.g., one which may be administered in combination with an anti-TIGIT antibody or antigen-binding fragment described herein) is an inhibitor of the programmed death-1 (PD-1) pathway. The programmed cell death 1 (PD-1) pathway represents an immune control switch which may be engaged by tumor cells to overcome active T cell immune surveillance. The ligands for PD-1 (PD-L1 and PD-L2) are constitutively expressed or can be induced in various tumors. As used herein, the term "PD-1 inhibitor" is meant to refer to any inhibitor of PD-1 and/or the PD-L1 pathway. Exemplary PD-1 inhibitors include but are not limited to anti-PD-1 and anti-PD-L1 antibodies. In some embodiments, the checkpoint inhibitor is an anti-PD-1 antibody. Exemplary anti-PD-1 antibodies include but are not limited to nivolumab and pembrolizumab (MK-3475). Nivolumab, for example, is a fully human immunoglobulin G4 (IgG4) PD-1 immune checkpoint inhibitor antibody that disrupts the interaction of the PD-1 receptor with its ligands PD-L1 and PD-L2, thereby inhibiting the cellular immune response (Guo et al. (2017) J Cancer 8(3):410-6). In some embodiments, the checkpoint inhibitor is nivolumab. Pembrolizumab, for example, is a potent and highly-selective humanized monoclonal antibody of the IgG4/kappa isotype designed to directly block the interaction between PD-1 and its ligands, PD-L1 and PD-L2. Pembrolizumab enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFN-γ), and other cytokines. In some embodiments, the checkpoint inhibitor is pembrolizumab. Exemplary anti-PD-L1 antibodies include but are not limited to atezolizumab, avelumab, and durvalumab. Atezolizumab, for example, is an IgG1 humanized monoclonal antibody that is reported to block the PD-1/PD-L1 interaction, by targeting the expressed PD-L1 on numerous kinds of malignant cells. This blockage of the PD-1/PD-L1 pathway may stimulate the immune defense mechanisms against tumors (Abdin et al. (2018) Cancers (Basel) 10(2):32). In some embodiments, the checkpoint inhibitor is atezolizumab, avelumab, or durvalumab.

In some embodiments, a checkpoint inhibitor (e.g., one which may be administered in combination with an anti-TIGIT antibody or antigen-binding fragment described herein) is targeted at PD-1/PD-L1, CTLA-4, OX40, CD40, LAG3, TIM3, GITR, and/or KIR. In some embodiments, a checkpoint inhibitor is targeted at CTLA-4, OX40, CD40, and/or GITR. In some embodiments, a checkpoint inhibitor is targeted with an inhibitory antibody or other similar inhibitory molecule (e.g., an inhibitory anti-CTLA-4 or anti-PD-1/PD-L1 antibody). In some other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T cell suppression, while enhancing effector T cell functions. Agonist anti-GITR antibodies have also been shown to make effector T cells more resistant to the inhibition induced by regulatory T cells (Karaki et al. (2016) Vaccines (Basel) 4(4):37). Likewise, agonist CD40 antibodies demonstrate T cell-dependent anti-tumor activity. Activation of CD40 on dendritic cells increases cross-presentation of tumor antigens and consequently the number of activated tumor-directed effector T cells (Ellmark et al. (2015) Oncoimmunol. 4(7):e1011484).

The terms "combination" or "combination therapy," as used herein, refer to the administration of at least one anti-TIGIT antibody, antigen-binding fragment, or composition together with an additional agent or therapy (e.g., a checkpoint inhibitor), as part of a treatment regimen intended to provide a beneficial effect from the co-action of one or more of the administered agents. In some embodiments, the combination may also include one or more additional agents, including but not limited to chemotherapeutic agents and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a disease, disorder, or condition (e.g., a cancer or an infection or infectious disease). This includes concurrent administration of the two or more treatments, as well as consecutive administration in any order. For example, in some embodiments, the two or more treatments are delivered after the subject has been diagnosed with a disease, and before the disease has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., an anti-TIGIT antibody, antigen-binding fragment, or composition disclosed herein and a checkpoint inhibitor) are comprised in the same composition. Such compositions may be administered in any appropriate form and by any suitable route. In other embodiments, the two treatments (e.g., an anti-TIGIT antibody, antigen-binding fragment, or composition disclosed herein and a checkpoint inhibitor) are administered in separate compositions, in any appropriate form and by any suitable route. For example, in some embodiments, a composition comprising an anti-TIGIT antibody or antigen-binding fragment and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease, is greater than what would be observed with the first treatment delivered in the absence of the second treatment. In other embodiments, an analogous situation is observed with the second treatment.

Typically, a therapeutically effective amount of an anti-TIGIT antibody or antigen-binding fragment is employed in the pharmaceutical compositions of the disclosure. The antibody or antigen-binding fragment may be formulated into a pharmaceutically acceptable dosage form by conventional methods known in the art.

Exemplary dosage regimens for anti-TIGIT antibodies or antigen-binding fragments alone or in combination with at least one additional therapeutic agent include, for example, a single bolus of one or both agents at one time or several divided doses over a predetermined period of time. For any particular subject, specific dosage regimens may be adjusted over time according to the individual's need, and the professional judgment of the treating physician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active agent calculated to produce the desired therapeutic effect in association with the required pharmaceutically acceptable carrier.

Dosage values for compositions comprising an anti-TIGIT antibody or antigen-binding fragment and/or any additional therapeutic agent(s) may be selected based on the unique characteristics of the active agent(s), and the particular therapeutic effect to be achieved. A physician or veterinarian can start doses of the antibody or antigen-binding fragment employed in the pharmaceutical composition at levels lower than that required to achieve the desired therapeutic effect and gradually increase the dosage until the desired effect is achieved. In general, effective doses of the compositions of the disclosure, for the treatment of an immune-related disease (e.g., a cancer or an infection or infectious disease) may vary depending upon many different factors, including the particular disorder being treated, the particular subject being treated, the physiological state of the subject, the cause of the disorder, the site of delivery of the agent, whether the subject is human or an animal, whether treatment is prophylactic or therapeutic, and other factors known to medical practitioners. The selected dosage level may also depend upon a variety of pharmacokinetic factors including the activity of the particular compositions of the disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject being treated, and like factors.

A therapeutically effective amount of the antibodies and antigen-binding fragments described herein will generally provide therapeutic benefit without causing substantial toxicity. Toxicity and therapeutic efficacy of an antibody or antigen-binding fragment can be determined by standard pharmaceutical procedures, e.g., in cell culture or in animal models. Cell culture assays and animal studies can be used to determine the LD50 (the dose lethal to 50% of a population) and the ED50 (the dose therapeutically effective in 50% of a population). The dose ratio between toxic and therapeutic effects is the therapeutic index, which can be expressed as the ratio LD50/ED50. In some embodiments, an antibody or antigen-binding fragment exhibits a high therapeutic index. The data obtained from cell culture assays and animal studies (e.g., in mice and/or primates) be used in formulating a range of dosages suitable for use in humans. In some embodiments, the dosage lies within a range of circulating concentrations that include the ED50 with minimal or no toxicity. The dosage may vary within this range depending upon a variety of factors, such as those described above. The exact formulation, route of administration, and dosage can be chosen by the treating physician in view of the subject's condition.

In some embodiments, an anti-TIGIT antibody, antigen-binding fragment, or composition described herein is administered on a single occasion. In other embodiments, an anti-TIGIT antibody, antigen-binding fragment, or composition described herein is administered on multiple occasions. Intervals between single dosages can be, e.g., hourly, daily, weekly, bi-weekly, monthly, or yearly. Intervals can also be irregular, based on measuring blood levels of the administered active agent (e.g., the antibody or antigen-binding fragment) in the subject in order to maintain a relatively consistent plasma concentration of the agent. The dosage and frequency of administration of an anti-TIGIT antibody or antigen-binding fragment may also vary depending on whether the treatment is prophylactic or therapeutic. In prophylactic applications, a relatively low dosage may be administered at relatively infrequent intervals over a long period of time. Some subjects may continue to receive treatment for the rest of their lives. In therapeutic applications, a relatively higher dosage at relatively shorter intervals is sometimes required until progression of the disease is reduced or terminated, and/or until the subject shows partial or complete amelioration of one or more symptoms of disease. Thereafter, the subject may be administered a lower, e.g., prophylactic, dosage regime.

In some embodiments, kits for use in the therapeutic applications described herein are also provided. In some embodiments, the present disclosure provides a kit comprising an anti-TIGIT antibody or antigen-binding fragment. In some embodiments, the kit further comprises one or more additional components, including but not limited to: instructions for use; other reagents, e.g., an additional therapeutic agent (e.g., a checkpoint inhibitor), pharmaceutically acceptable carriers, etc.; and devices, containers, or other materials for preparing the antibody or antigen-binding fragment for administration. Instructions for use can include guidance for therapeutic applications including suggested dosages and/or modes of administration, e.g., in a subject having or suspected of having an immune-related disease (e.g., a cancer or an infection or infectious disease).

In some embodiments, the present disclosure provides a kit including an anti-TIGIT antibody or antigen-binding fragment and a package insert comprising instructions for using the antibody or antigen-binding fragment for treating or delaying progression of an immune-related disease in a subject (e.g., a cancer or an infection or infectious disease). In some embodiments, the disclosure provides a kit including an anti-TIGIT antibody or antigen-binding fragment, at least one additional therapeutic agent (e.g., a checkpoint inhibitor), and a package insert comprising instructions for using the combination for treating or delaying progression of an immune-related disease in a subject (e.g., a cancer or an infection or infectious disease). The subject may, for example, be a human. Any of the exemplary anti-TIGIT antibodies or antigen-binding fragments described herein, alone or in combination with one or more additional therapeutic agents, may be included in the kit.

In some embodiments, the present disclosure provides a kit including an anti-TIGIT antibody or antigen-binding fragment and a package insert comprising instructions for using the antibody or antigen-binding fragment for activating and/or killing one or more immune cells in a subject. In some embodiments, the disclosure provides a kit including an anti-TIGIT antibody or antigen-binding fragment, at least one additional therapeutic agent (e.g., a checkpoint inhibitor), and a package insert comprising instructions for using the combination for activating and/or killing one or more immune cells in a subject. In some embodiments, the subject is a human. Any of the exemplary anti-TIGIT antibodies or antigen-binding fragments described herein, alone or in combination with one or more additional therapeutic agents, may be included in the kit.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

Example 1: Production of TIGIT Immunogens cDNA fragments encoding the human and mouse TIGIT IgV domains were separately synthesized (Integrated DNA Technologies, Inc.) and subcloned into a mammalian expression vector pSecTag2/Hygro (Invitrogen). The recombinant proteins were produced by transfecting each of the expression constructs into mouse myeloma NS0 cells (European Collection of Authenticated Cell Cultures (ECACC)) using Effectene (Qiagen). After selection with hygromycin B (400 µg/ml) for 2 weeks, cells were cultured in shaker flasks at an initial seeding density of $5 \times 10^5$ cells/ml in a chemically-defined medium HyQNS0 (Hyclone) without serum addition. Medium was harvested 5 days later and the human and mouse TIGIT IgV domains were purified separately from the supernatant by Strep-Tactin XT Superflow chromatography (IBA Technology, Inc.). The purities of the recombinant human and mouse TIGIT IgV domains were analyzed by SDS-PAGE (FIG. 1). The purified proteins were used for animal immunization.

Example 2: Generation of Monoclonal Antibodies Against TIGIT

Ten 6- to 12-week-old SJL/J mice were immunized by intraperitoneal injection with a mixture of 50 µg each of recombinant human and mouse TIGIT IgV domains in the presence of complete Freund's adjuvant at a volume ratio of 1:1 (v/v). Animals were boosted by injection with the same immunogens in the presence of incomplete Freund's adjuvant at a volume ratio of 1:1 (v/v). A total of one- to four-boosters, depending on the serum antibody titer via ELISA, were administered at a time interval of once per week.

Splenocytes and lymphoid cells from eight mice with the highest serum antibody titer against either the human or mouse TIGIT IgV domain were used for fusion with myeloma NS0 cells (ECACC). Hybridoma cells were screened against both human and mouse TIGIT IgV, fused with a human Fc domain (Sino Biological Inc.). Competition ELISA, which applied a fixed concentration of 0.5 µg/ml of recombinant CD155-human Fc fusion protein (Sino Biological Inc.), was used to identify hybridoma clones capable of blocking the interaction of TIGIT and CD155. Five hybridoma monoclones with TIGIT/CD155 blockade potency were selected and further evaluated by AlphaLISA competition assays.

Example 3: AlphaLISA Competition Assays

To evaluate inhibition of binding of TIGIT to CD155 by anti-TIGIT antibodies, AlphaLISA assays were performed using a TIGIT:CD155 Homogeneous Assay Kit (PBS Biosciences, #72029). Aliquots (6 µl) of solution containing TIGIT-biotin (final concentration 0.2 ng/µl) and 4-fold serial dilution of the test antibodies (final volume 2 µl) were added into a 384-well plate. The plates were covered with a lid and incubated at room temperature for 30 min. Then, 2 µl of histidine-tagged CD155 were added (final concentration 0.05 ng/µl) into each well and incubated at room temperature for 60 min. Finally, aliquots (5 µl) of streptavidin-conjugated donor beads (final concentration 10 µg/ml) and 5 µl of anti-His tag acceptor beads (final concentration 20 µg/ml) were added and the plate was incubated at room temperature for 30 min in the dark. AlphaLISA signals were measured on an EnSpire Alpha 2390 (Perkin-Elmer Life Sciences). 15A6 (U.S. Pat. No. 10,189,902) and MBSA43 (Thermo Fisher Scientific, #16-9500-82) were used as reference antibodies.

The results are shown in FIG. 2A-2E. The three anti-TIGIT monoclonal antibodies, 7D4, 2C9, and 3A9, exhibited TIGIT/CD155 blockade potencies ($IC_{50}$) of 0.32, 0.40, and 0.55 nM, respectively. These antibodies were selected for further functional studies.

Example 4: V Gene Sequencing of Anti-TIGIT Monoclonal Antibodies

Total RNA from approximately $10^6$ cells of hybridoma clones 7D4, 2C9, and 3A9, which secrete anti-TIGIT IgGs, were isolated and the cDNA fragments encoding the heavy chain and light chain variable regions of each antibody were obtained by RT-PCR using the SMARTer RACE 5'/3' Kit (Takara Bio USA, Inc., #634913), following the manufacturer's protocol. Amino acid sequences of the 7D4, 2C9, and 3A9 antibodies are listed in Tables 2-5.

Example 5: Binding of Anti-TIGIT Antibodies to Jurkat Cells Expressing Human TIGIT Sequential dilutions of Protein A column-purified 7D4, 2C9, and 3A9 antibodies were separately incubated with $5 \times 10^5$ of human TIGIT-expressing Jurkat cells (TIGIT/Jurkat) in 50 µl of FACS buffer (0.2% BSA in Dulbecco's phosphate-buffered saline (DPBS) containing 0.09% sodium azide) on ice for 1 hour. After washing, the cells were stained with anti-mouse IgG conjugated with PE dyes and antibody binding strength was analyzed by flow cytometry.

Figure 3A:
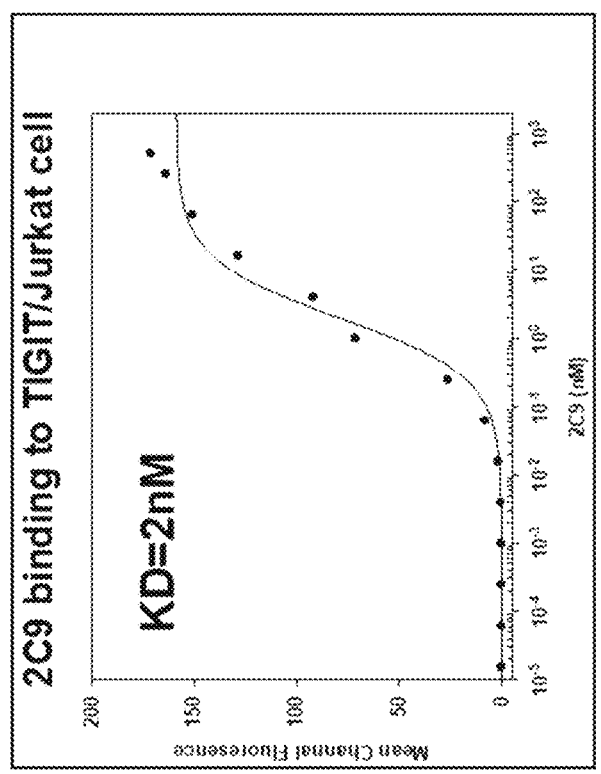
FIG. 3A-3C show graphs showing the flow cytometric binding of anti-TIGIT antibodies 7D4 (FIG. 3A), 2C9 (FIG. 3B), and 3A9 (FIG. 3C) to Jurkat cells expressing human TIGIT (TIGIT/Jurkat). The levels of antibody binding, as measured by median fluorescence intensity (MFI), are plotted against antibody concentrations. The equilibrium binding constant ($K_D$) of each antibody is indicated.
Figure 3B:
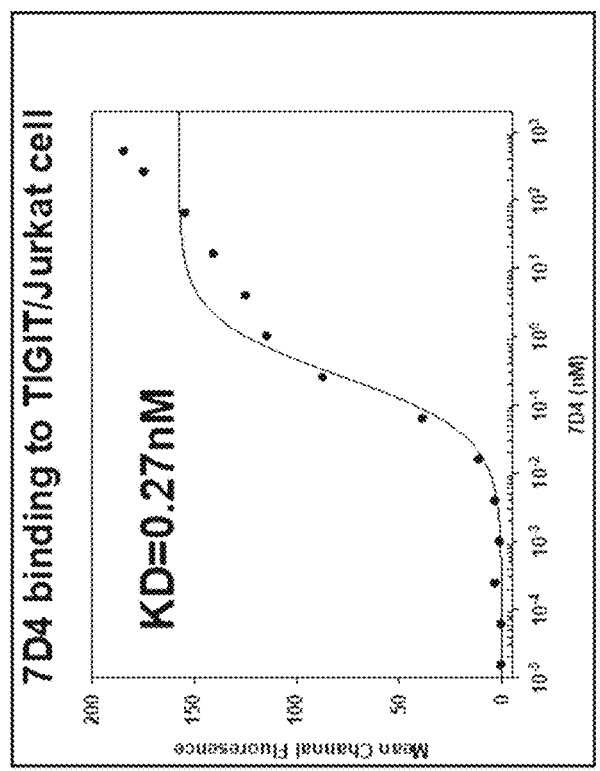
Figure 3C:
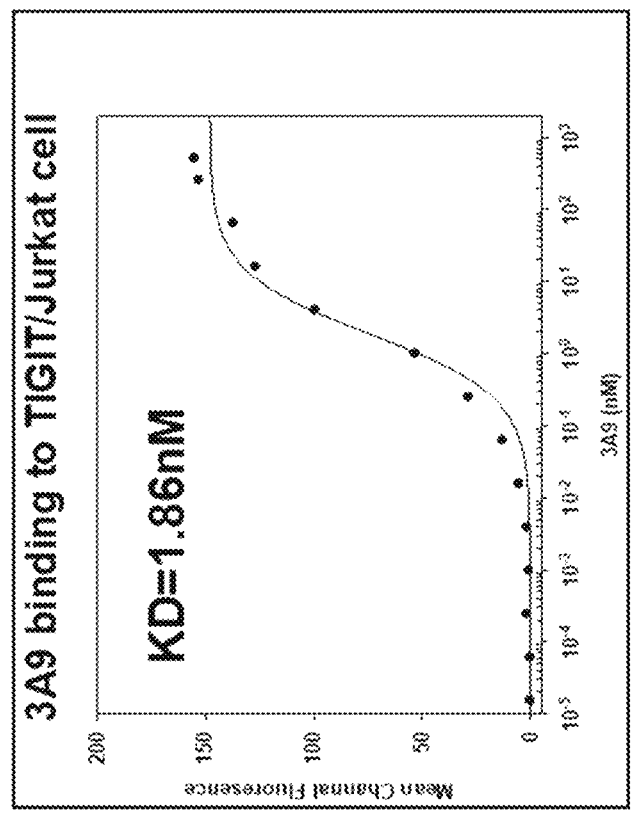

The results are shown in FIG. 3A-3C. 7D4, 2C9, and 3A9 exhibited equilibrium binding constants ($K_D$) of 0.27, 2.0, and 1.86 nM to TIGIT/Jurkat cells, respectively.

Example 6: Binding of Anti-TIGIT Antibodies to Human, Cynomolgus Monkey (Cyno), and Mouse TIGIT To assess species cross-reactivity of anti-TIGIT antibodies 7D4, 2C9, and 3A9, ELISA binding assays to human, cynomolgus monkey, and mouse TIGIT were performed. 1 µg/ml each of human, cyno (R&D Systems, Inc., #9380-TG), and mouse TIGIT in 50 µl of DPBS were coated on 96-well plates at 4° C. for overnight. After washing the plates with phosphate-buffered saline containing 0.05% of Tween 20 (PBST), a sequential dilution of 7D4, 2C9, and 3A9 antibodies was added separately and the plates were incubated at 37° C. for 1 hour. After washing the plates three times with PBST, the plates were incubated with an anti-mouse Fcγ polyclonal antibody conjugated with horseradish peroxidase (HRP) at 37° C. for 1 hour. After washing the plates three times with PBST, 100 µl of 3,3',5,5'-tetramethylbenzidine (TMB) substrate (Thermo Fisher Scientific, #34018) were added into each well. After 5 to 10 min of color development, 50 µl of stop solution (2 N of HCl) were added into each well and plates were read by spectrophotometer at a wavelength of 450 nm.

Figure 4:
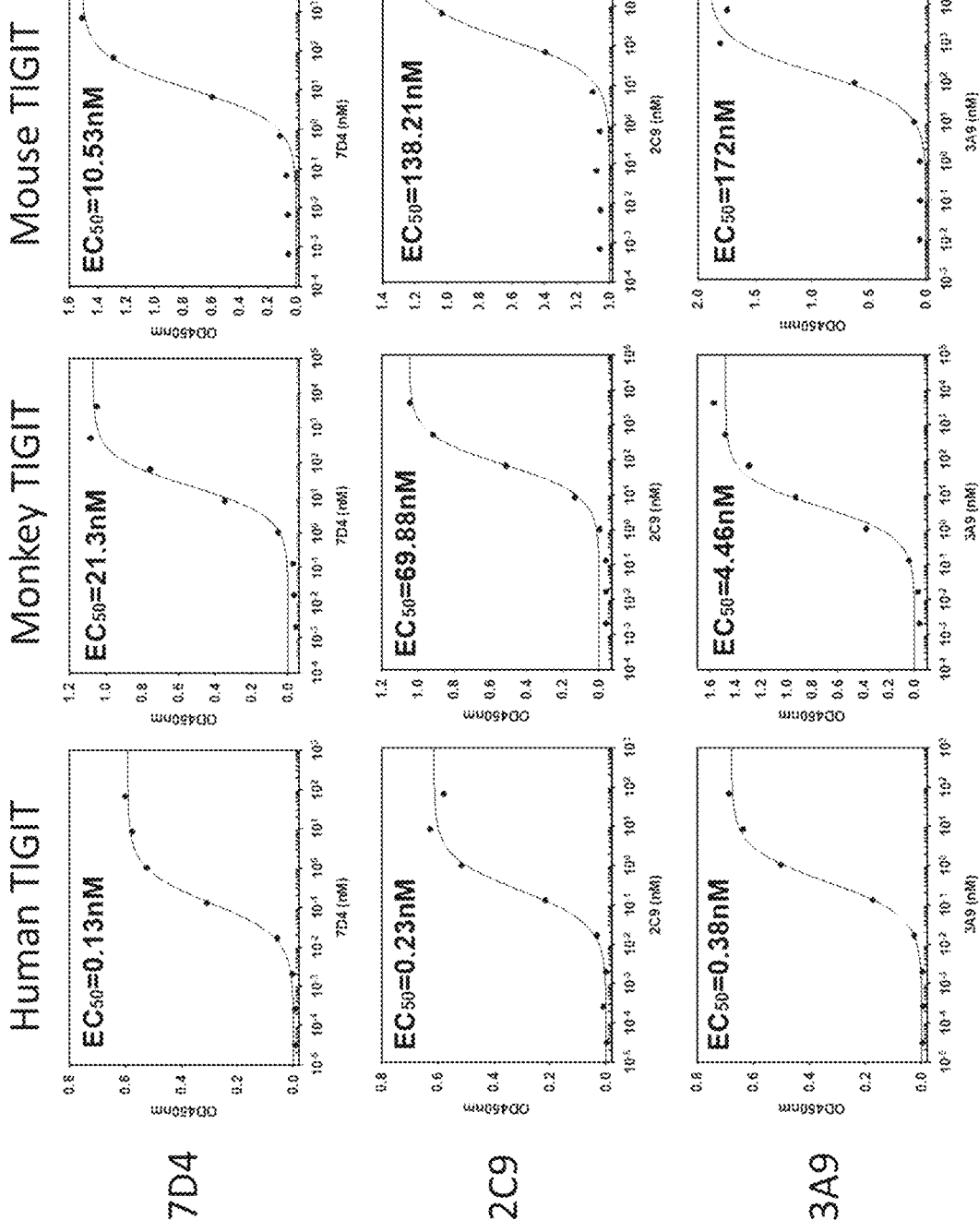
FIG. 4 shows a graph showing species cross-reactivity of anti-TIGIT antibodies 7D4, 2C9, and 3A9 to human, cyno monkey, and mouse TIGIT. An ELISA-based assay was performed by coating plates with the recombinant TIGIT IgV domain of each species. After incubating with a sequential dilution of the antibodies, the binding potency of each anti-TIGIT antibody was measured by a detecting anti-mouse Fcγ polyclonal antibody conjugated with HRP. Binding curves were plotted by a four-parameter logistic fit equation and the binding potencies ($EC_{50}$) were determined.

The results are shown in FIG. 4. 7D4, 2C9, and 3A9 exhibited $EC_{50}$ values to human TIGIT in the sub-nM range. 7D4 exhibited an $EC_{50}$ value of 10.53 nM to mouse TIGIT.

Example 7: TIGIT/CD155 Blockade Assay

The potency of anti-TIGIT antibodies to inhibit TIGIT:CD155 cellular signaling was performed by a cell-based, luciferase reporter gene assay using a TIGIT/CD155 Blockade Bioassay Kit (Promega, #J2405) according to the manufacturer's protocol. Briefly, frozen CHO-K1 cells expressing CD155 (CD155/CHO) and Jurkat cells expressing TIGIT (TIGIT/Jurkat) cells were thawed and recovered with fresh media and incubated at 37° C. overnight. The next day, CD155/CHO cells were seeded in a 96-well plate at a density of $4\times10^4$ cells/well in 100 µl of culture media. A series dilution of anti-TIGIT antibodies (40 µl in volume) was added into each well, followed by adding 40 µl of TIGIT/Jurkat cells at a density of $1.5\times10^5$ cells/well. Cells were co-cultured at 37° C. for 6 hours. Subsequently, 80 µl of One Glo reagent were added and the plate was incubated at room temperature for 15 min. The reaction solution was then transferred into a white plate for luminescence measurement.

Figure 5A:
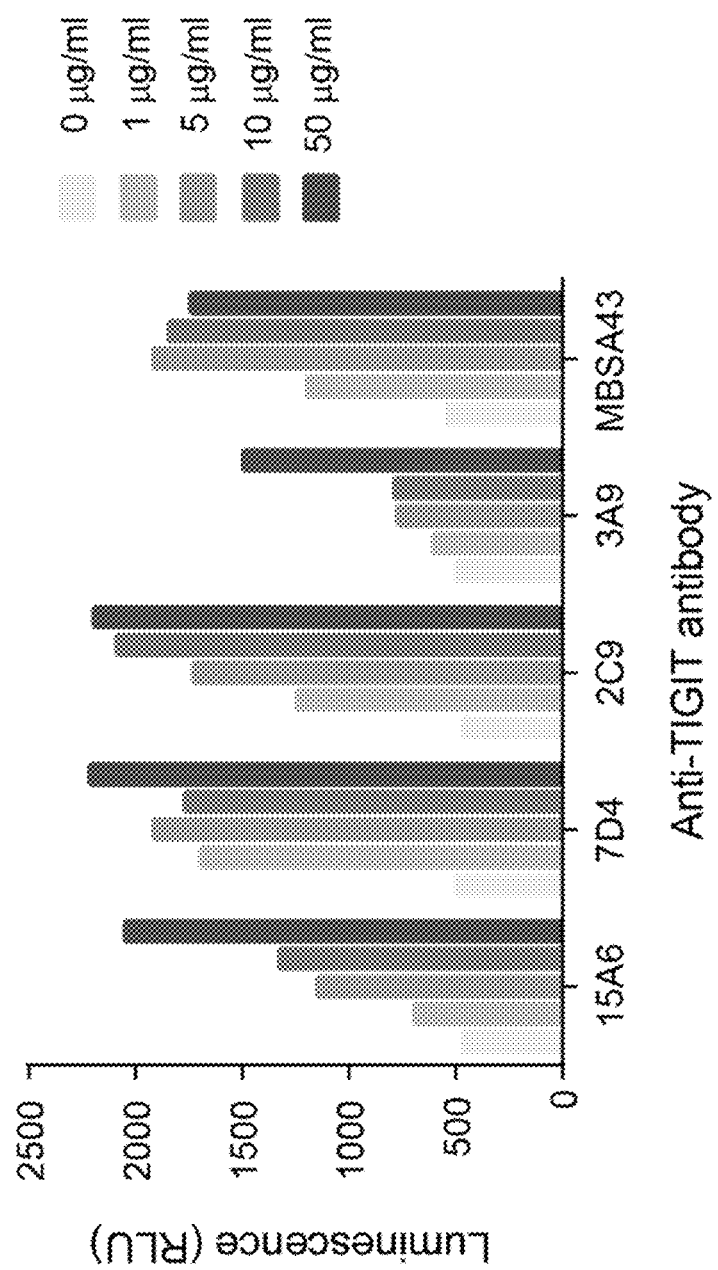
FIG. 5A shows the results of a human TIGIT/CD155 blockade bioassay by different anti-human TIGIT antibodies, including reference antibodies 15A6 and MBSA43, and antibodies 7D4, 2C9, and 3A9.
Figure 5B:
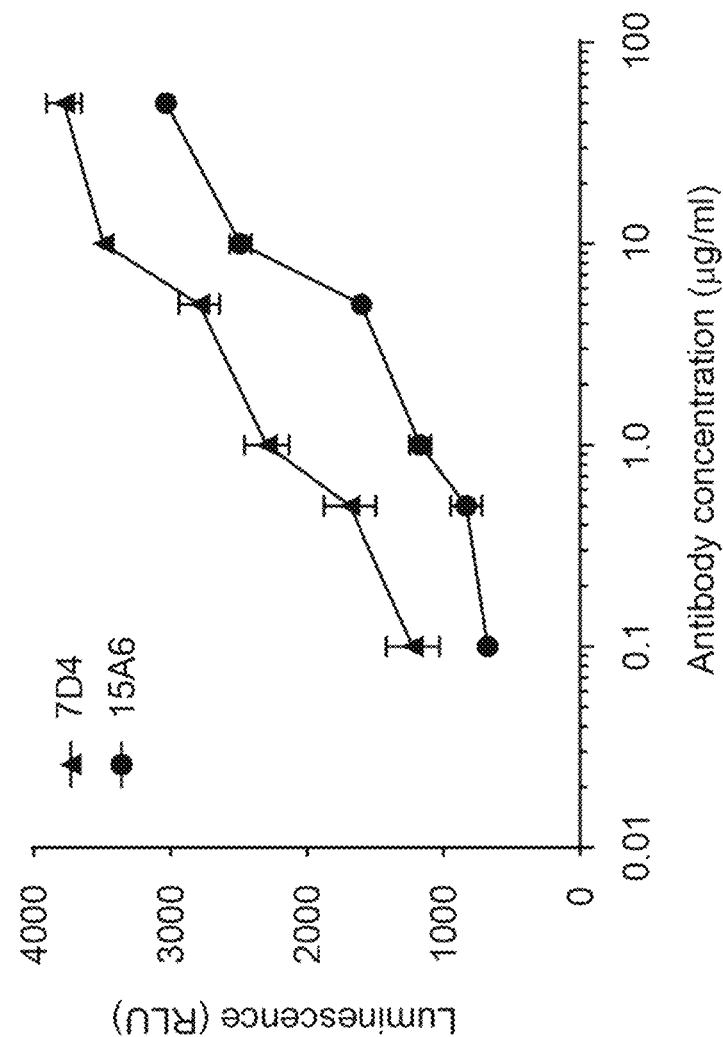
FIG. 5B shows a comparison between antibodies 7D4 and 15A6 for inhibition of CD155/CHO binding to TIGIT/Jurkat cells. Assays were performed using a TIGIT/CD155 cell-based reporter system.

The results are shown in FIG. 5A-5B. Anti-TIGIT antibodies 7D4, 2C9, and 3A9 blocked the interaction of TIGIT and CD155, resulting in the activation of T cells in a dose-dependent manner (FIG. 5A). Furthermore, in a TIGIT/CD155 blockade assay, 7D4 exhibited greater enhancement of T cell activation than the reference antibody 15A6 (FIG. 5B).

Example 8: PD-1/PD-L1 and TIGIT/CD155 Combination Blockade Assay

To assess the potency of the anti-TIGIT antibody 7D4 and the reference antibody 15A6, in combination with an anti-PD-1 antagonist antibody (pembrolizumab), a cell-based, luciferase reporter gene assay was performed using a PD-1+ TIGIT Combination Bioassay Kit (Promega, #J2120) according to the manufacturer's protocol. Briefly, frozen PD-L1+CD155-expressing CHO-K1 cells were thawed and seeded in a 96-well plate at a density of $4\times10^4$ cells/well in 100 µl of culture media. Cells were incubated at 37° C. to allow cells to attach. The next day, the medium was removed and a series dilution of anti-TIGIT and anti-PD-1 antibodies was added into each well (40 µl in volume). Finally, $1\times10^5$ of the frozen recovered PD-1+TIGIT/Jurkat cells were added to each well (40 µl in volume). After a 6-hour incubation, 80 µl of Bio-Glo reagent were added to each well and luminescence was quantified using a luminometer.

Figure 6:
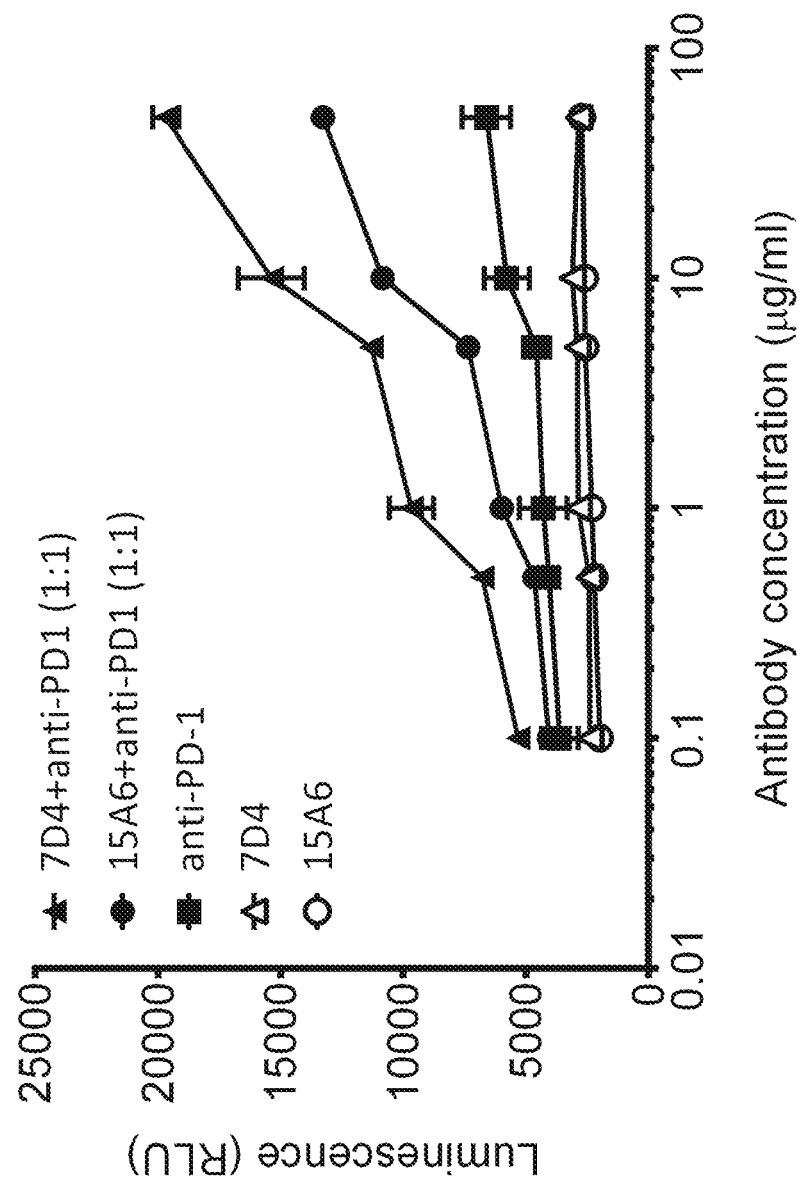
FIG. 6 shows the results of an assay combining 15A6 (reference antibody) or antibody 7D4 with an antagonistic anti-PD-1 antibody (pembrolizumab) to evaluate T cell activation. Assays were performed using a PD-1/PD-L1+ TIGIT/CD155 combination cell-based reporter system (Promega). T cell activation was measured by luminescence intensity.

The results are shown in FIG. 6. The combination of the anti-PD-1 antibody, pembrolizumab, with either 7D4 or the reference 15A6 at an anti-PD-1:anti-TIGIT antibody concentration ratio of 1:1 (ranging from 0.1 to 100 µg/ml), had a greater T cell activation activity than pembrolizumab alone. Moreover, the combination of 7D4 and pembrolizumab exhibited greater enhancement of T cell activation than the reference antibody 15A6.

Example 9: T Cell Activation by 7D4, 2C9, and 3A9

For the assessment of T cell activation by anti-TIGIT antagonist antibodies, both a Jurkat cell line expressing human TIGIT and human T cells were adopted for the measurement of IL-2 and IL-2/IFN-γ cytokine secretion upon antibody treatments, respectively. CD155/CHO cells were seeded in a 96-well plate at a density of $4\times10^4$ cells/well in 100 µl of RPMI 1640 culture media and incubated overnight. The next day, after removing the culture supernatant, a series dilution of anti-TIGIT antibodies (7D4, 2C9, and 3A9) and reference antibodies (15A6 and MBSA43) was added (40 µl/well) separately, followed by the addition of TIGIT/Jurkat cells at a density of $1.5\times10^5$ cells/well in 40 µl of culture media. After co-cultivation for 26 hours, plates were centrifuged at 4000 rpm for 5 min and the concentrations of IL-2 from the supernatant were analyzed by ELISA.

Figure 7:
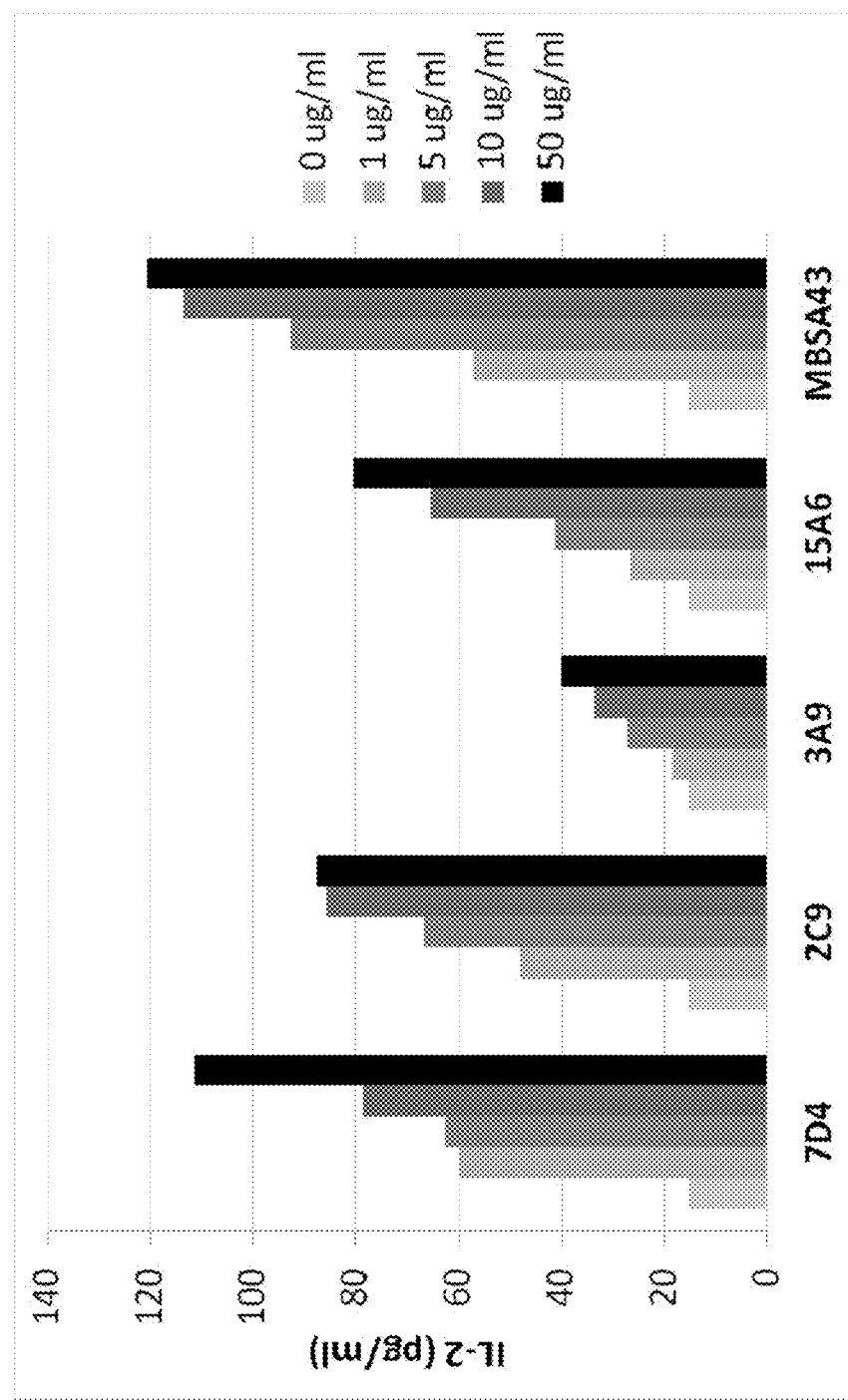
FIG. 7 shows an induction of IL-2 secretion of Jurkat cells expressing human TIGIT by incubation of a sequential dilution of different anti-TIGIT antibodies, including reference antibodies 15A6 and MBSA43, and the antibodies 7D4, 2C9, and 3A9.

The results are shown in FIG. 7. The different anti-TIGIT antibodies increased the secretion of IL-2 by TIGIT/Jurkat cells in a concentration-dependent manner.

To evaluate the activation of TIGIT-expressing cells from human peripheral blood mononuclear cells (PBMCs), PBMCs ($5\times10^4$ cells/well) from 3 separate healthy donors were treated with plate-coated recombinant human CD155-Fc fusion protein (1 µg/ml in DPBS in 96-well culture plates), in the presence of a 10-fold serial dilution of 7D4 at 37° C. for 1 hour. Anti-human CD3 antibody (OKT3) was added to each well at a final concentration of 1 µg/ml. After 48 hours of incubation, the plates were centrifuged for 3 min at 1500 rpm, and the supernatant concentrations of IL-2 and IFN-γ were analyzed by ELISA.

Figure 8A:
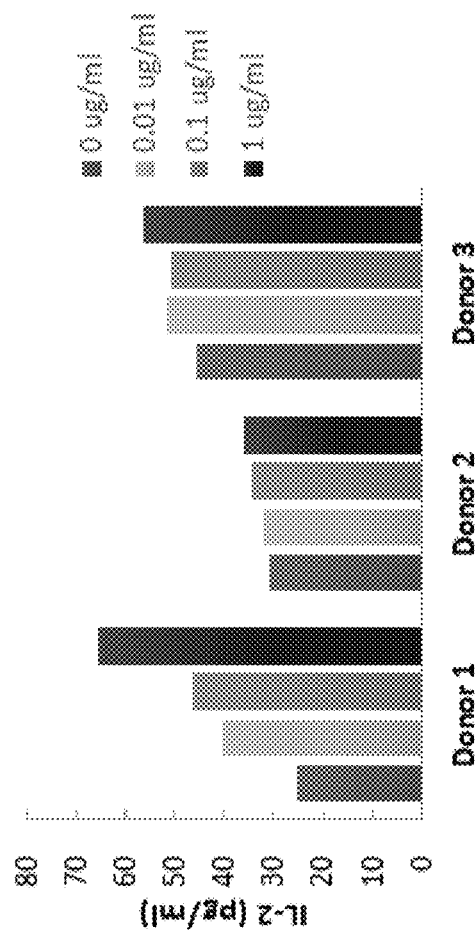
FIG. 8A-8B show interleukin-2 (IL-2) (FIG. 8A) and interferon-γ (IFN-γ) (FIG. 8B) secretion from incubation of a sequential dilution of the 7D4 antibody with PBMCs from three separate healthy human donors, in the presence of immobilized CD155 and a T cell-activating anti-CD3 antibody.
Figure 8B:
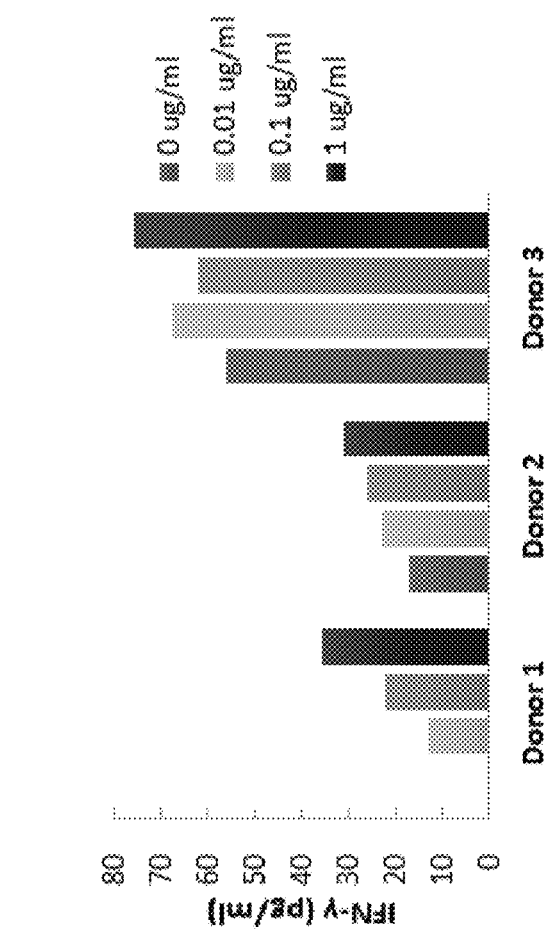

The results are shown in FIG. 8A-8B. In PBMCs from three different healthy human donors and in the presence of T cell-activating anti-CD3 antibody OKT3, 7D4 blocked the T cell suppression signal resulting from the interaction between TIGIT-expressing T cells and CD155. The activated T cells also secreted the proinflammatory cytokines IL-2 and IFN-γ. Donors 1-3 showed dose-dependent T cell activation in response to the addition of 7D4, with Donor 1 showing the strongest response. Basal levels (at 0 µg/ml of 7D4) of T cell activation by anti-CD3 antibody were higher in Donors 2 and 3 than in Donor 1.

Example 10: Construction, Expression, and Purification of Recombinant Anti-TIGIT Antibodies For the expression of recombinant mouse antibodies, cDNA fragments encoding the heavy and light chain variable regions of each antibody were subcloned into mammalian expression vectors pFUSEss-CHIg-mG2a (Invivogen) and pSecTag2/Hygro (Thermo Fisher Scientific). Plasmids containing the heavy and light chain cDNAs of each antibody were co-transfected into mouse myeloma NS0 cells using Effectene (Qiagen). After selection with hygromycin B (400 µg/ml) and G418 (800 µg/ml) for 4 weeks, culture media from several stable clones were screened by ELISA with recombinant human TIGIT IgV domain as coating and anti-mouse IgG Fcγ-HRP as detection reagents. High-expressing clones from each antibody were picked and cultured in shaker flasks at an initial seeding density of $5\times10^5$ cells/ml in a chemically-defined medium HyQNS0 (Hyclone) without serum addition. The medium was harvested after 5 days, and the antibodies were purified from the supernatant by Protein A (MabSelect SuRe) columns (Cytiva).

Example 11: Antibody Humanization of 7D4

Homology modeling was performed according to the procedures of Fan et al. ((2017) Biochem Biophys Rep 9: 51-60). The CDR regions of the mouse $V_H$ and $V_L$ regions of anti-TIGIT antibody 7D4 were grafted onto a human germline family of IGHV3-11 and IGKV3-11 framework regions, respectively. Several amino acid residues within the human framework regions were back mutated to the original mouse residues to maintain antibody binding affinity. Amino acid sequences of the hz7D4 antibody are listed in Tables 2-5.

The nucleotide sequences of the $V_H$ and $V_L$ regions of hz7D4 were synthesized and subcloned into mammalian expression vectors pFUSE-CHIg-hIG1 (Invivogen) harboring a signal peptide sequence and pSecTag2/Hygro (Invitrogen) containing the human kappa chain constant region, respectively. The reference human IgG1 antibodies, 15A6 and 1D3, were produced based on the $V_H$ and $V_L$ sequences in U.S. Pat. Nos. 10,189,902 and 10,017,572, respectively. The recombinant hz7D4, 15A6, and 1D3 hIgG1 antibodies were produced in CHO-S cells (Thermo Fisher Scientific) and were purified by Protein A (MabSelect SuRe) columns.

Figure 9A:
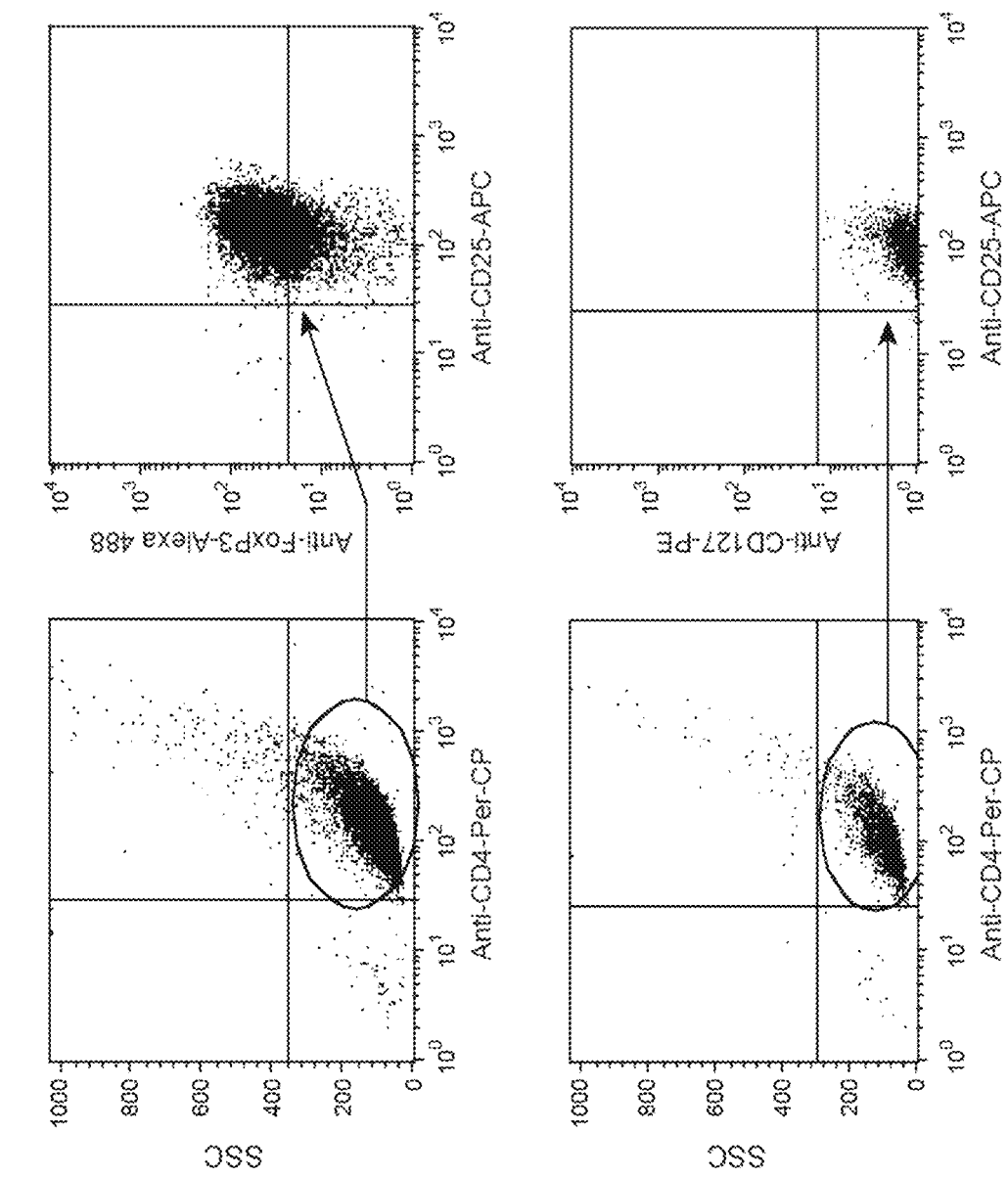
FIG. 9A-9B show exemplary characterizations of MJ[G11] cells.
Figure 9B:
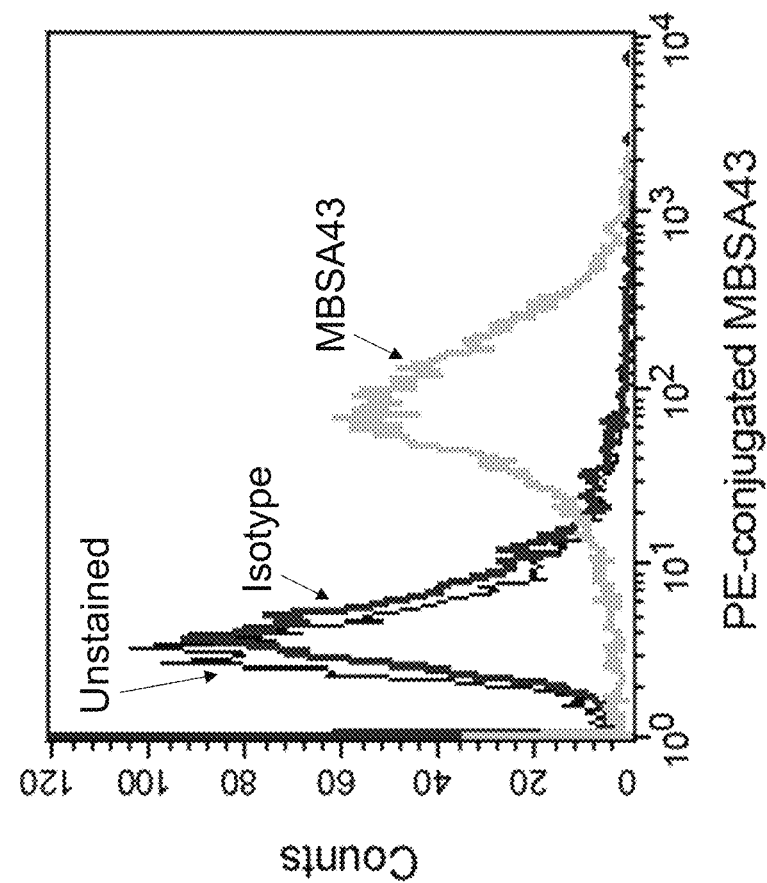

Example 12: Cell Competitive Binding Assays of the Humanized 7D4 (hz7D4) Antibody Anti-TIGIT antibodies, including hz7D4, and reference antibodies (15A6 and 1D3) were used to compete with CD155 for binding to cells expressing human TIGIT. MJ[G11](American Type Culture Collection (ATCC), CRL-8294) is a CD3+CD4+T lymphoma cell line carrying human T cell leukemia virus (HTLV-1). MJ[G11] cells were characterized by immunostaining with regulatory T cell phenotypic antibody markers, including CD4, CD25, CD127, and FoxP3, and found to be a regulatory T cell-like cell line (FIG. 9A). Moreover, MJ[G11] cells express human TIGIT constitutively, as shown by immunostaining with PE-conjugated anti-human TIGIT, MBSA43 antibody (FIG. 9B). A sequential 3-fold dilution of anti-TIGIT antibodies was added to $5\times10^5$ of human TIGIT-expressing Jurkat cells or $3\times10^5$ of MJ[G11] cells in 50 µl FACS buffer (0.2% BSA in DPBS containing 0.09% sodium azide) and incubated on ice for 30 min. Then, 10 µl of DyLight 650-conjugated CD155-human Fc fusion protein were added to the cells, to reach a final concentration of 1 µg/ml for human TIGIT-Jurkat cells and 1.5 µg/ml for MJ[G11] cells, and incubated for 30 min at 4° C. Cells were washed and analyzed by a FACSCalibur cytometer (Becton Dickinson). $IC_{50}$ values were calculated based on normalized median fluorescence intensity (MFI) values.

Figure 10A:
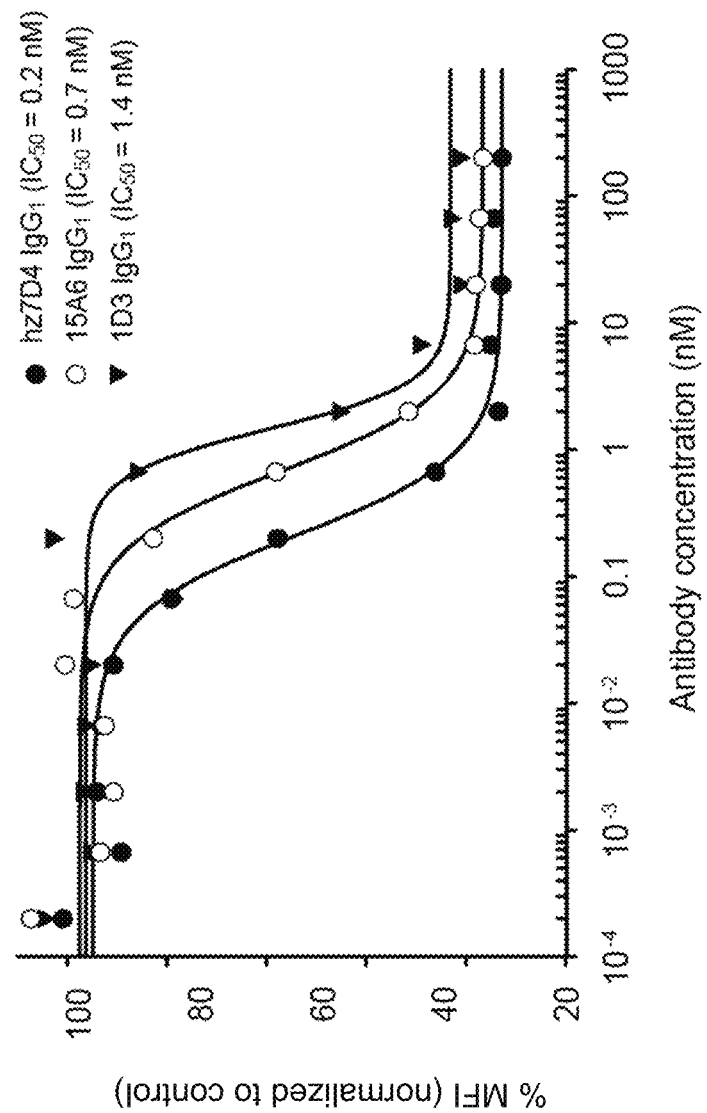
FIG. 10A-10B show diagrams showing the results of a competition assay between recombinant anti-TIGIT antibodies (hz7D4 human IgG1 ("hIgG1"), 15A6 hIgG1, and 1D3 hIgG1) and human CD155 for binding to Jurkat cells expressing human TIGIT (FIG. 10A) and MJ[G11] cells (FIG. 10B). After incubation and washing, the remaining bound DyLight 650-conjugated CD155-human Fc fusion was quantified by flow cytometry. The data are presented as percent of maximal fluorescence intensity, which is defined as the mean fluorescence intensity obtained by staining cells with DyLight 650-conjugated CD155-human Fc fusion in the absence of blocking antibodies (controls). The concentration of each antibody required to inhibit half the maximal fluorescence intensity ($IC_{50}$) was calculated.
Figure 10B:
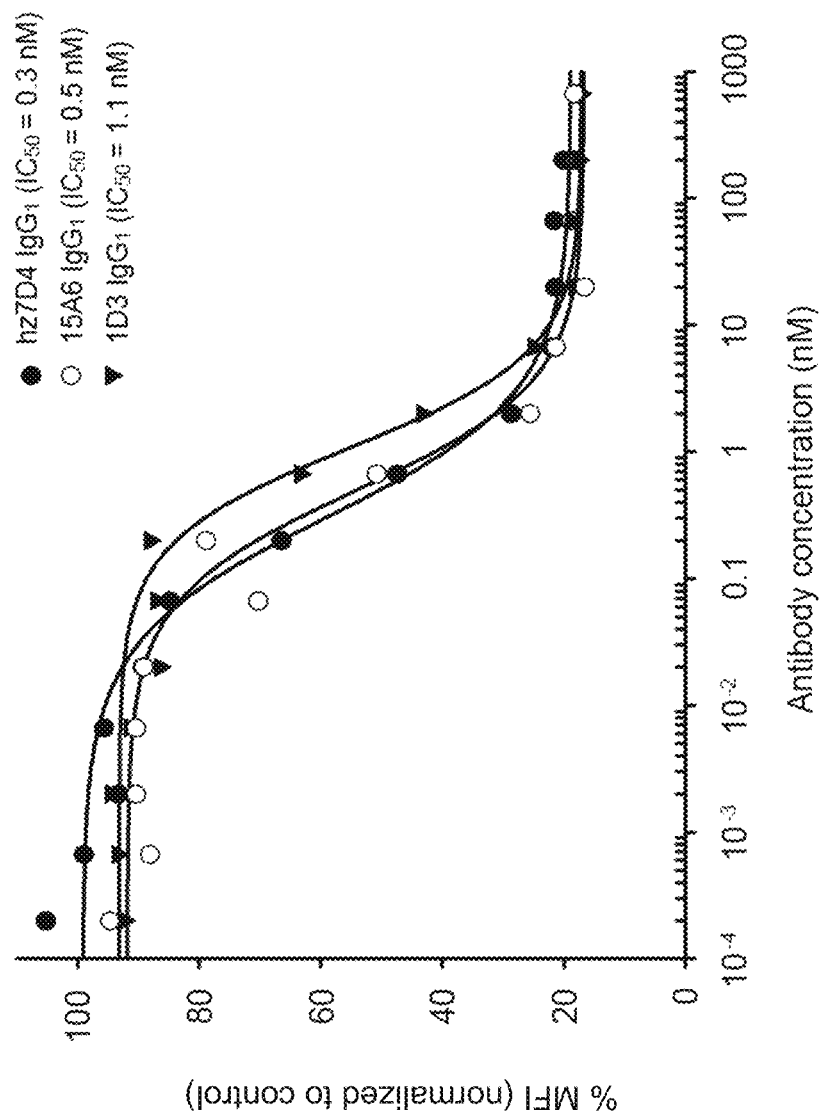

The results are shown in FIG. 10A-10B. Anti-TIGIT hIgG1 antibodies, hz7D4, 15A6 and 1D3, blocked CD155 from binding to both TIGIT/Jurkat and MJ[G11] cells. The concentration of blocking antibody required for achieving 50% CD155 binding inhibition ($IC_{50}$) of hz7D4 was 0.2 nM for TIGIT/Jurkat cells (FIG. 10A) and 0.3 nM for MJ[G11] cells (FIG. 10B).

Example 13: Phage-Display Antibody Library Construction and Affinity Maturation of hz7D4

The humanized 7D4 (hz7D4) scFv gene was cloned into the phagemid vector pKH at Nco I and Not I restriction sites. The amino acid sequences coding for the CDR3 regions of the heavy and light chains were mutated randomly with primers containing a stretch of NNK sequences. The heavy chain CDR3 (HCDR3) and the light chain CDR3 (LCDR3) libraries were each amplified by overlapping extension-PCR in a 50 µl reaction solution through the fusion of two fragments in equal molar amounts and 25 µmol of vector-cloning primers for 30 cycles at 95° C. for 30 sec, 60° C. for 30 sec, and 72° C. for 1 min. The amplified products were gel purified, digested with Nco I and Not I, and subcloned into pKH phagemid. The plasmid library was transformed into *Escherichia coli* TG1 cells by electroporation. The final M13 phage libraries carrying either the heavy chain CDR3 (HCDR3) or the light chain CDR3 (LCDR3) repertoire of hz7D4 scFv were rescued separately with KM13 helper phages.

Example 14: Affinity Maturation of hz7D4 Against Mouse TIGIT

For affinity maturation of hz7D4 scFv against mouse TIGIT, phages ($10^9$ cfu) from the heavy chain CDR3 (HCDR3) library were incubated with 1 nM of biotinylated mouse TIGIT IgV domain in 1 ml PBS/0.1% Tween-20 containing 3% non-fat milk for 1 hour at room temperature. The phages were captured by incubation with 50 µl of M280 streptavidin magnetic beads (Thermo Fisher Scientific, #11205D) for 15 min. Non-specific phages were eliminated by ten washes with PBS/0.1% Tween-20, followed by 10 washes with PBS for 5 min each. Bound phages were eluted with 0.1 M glycine (pH 2.0), neutralized with 1 M Tris-HCl (pH 8.0) and re-infected into log-phase TG1 cells. In the second panning round, phages ($10^9$ cfu) were used against 0.1 nM of the biotinylated mouse TIGIT IgV domain.

The nucleotide sequences of the phage clones that bind to mouse TIGIT IgV domain were determined. Three clones, designated 1G3, 2F1, and 3H2, were selected. The CDR amino acid sequences, including HCDR3, are listed in Table 2.

The selected three scFv clones with different amino acid sequences in the HCDR3 region were converted into mouse IgG2a isotype with DLE mutations at the Fc region (mIgG2a-DLE) and recombinant antibodies were expressed and purified in CHO-S cells as described above. Antibody Fc variants with S239D/A330U/1332E (DLE) mutations have been reported to enhance the effector function (Lazar et al. (2006) Proc Natl Acad Sci USA 103:4005-10). The ELISA binding of the human and mouse TIGIT, as well as the competition of mouse TIGIT/CD155 by the three hz7D4-derived antibody clones (1G3, 2F1, and 3H2) were analyzed and are summarized in Table 7. hz7D4 and a reference antibody, 1G9 (Bio X Cell, #BE0150), were included as comparators.

TABLE 7

ELISA binding measurements for hz7D4-derived antibodies, 1G3, 2F1, and 3H2

| Mouse isotype | hz7D4 mIgG2a | 1G3 mIgG2a-DLE | 2F1 mIgG2a-DLE | 3H2 mIgG2a-DLE | 1G9 IgG1 |
|---|---|---|---|---|---|
| hTIGIT binding $EC_{50}$ (nM) | 0.3 | 9.4 | 463.6 | 0.9 | No binding |
| mTIGIT binding $EC_{50}$ (nM) | 217 | 3.6 | 1.1 | 0.7 | 0.3 |
| mTIGIT/mCD155 competition $IC_{50}$ (nM) | No competition | 61.7 | 33.8 | 12.4 | 1.5 |

Example 15: Binding of Anti-TIGIT Antibodies to Mouse TIGIT-Expressing CHO Cells The Protein A column-purified anti-TIGIT antibodies listed in Table 7 were separately incubated with $5\times10^5$ of mouse TIGIT-expressing CHO cells (mTIGIT/CHO) in 50 µl of FACS buffer (0.2% BSA in Dulbecco's phosphate-buffered saline (DPBS) containing 0.09% sodium azide) at a final concentration of 2 µg/ml on ice for 1 hour. After washing, the cells were stained with anti-mouse IgG conjugated with PE dyes and antibody binding strength was analyzed by flow cytometry.

Figure 11:
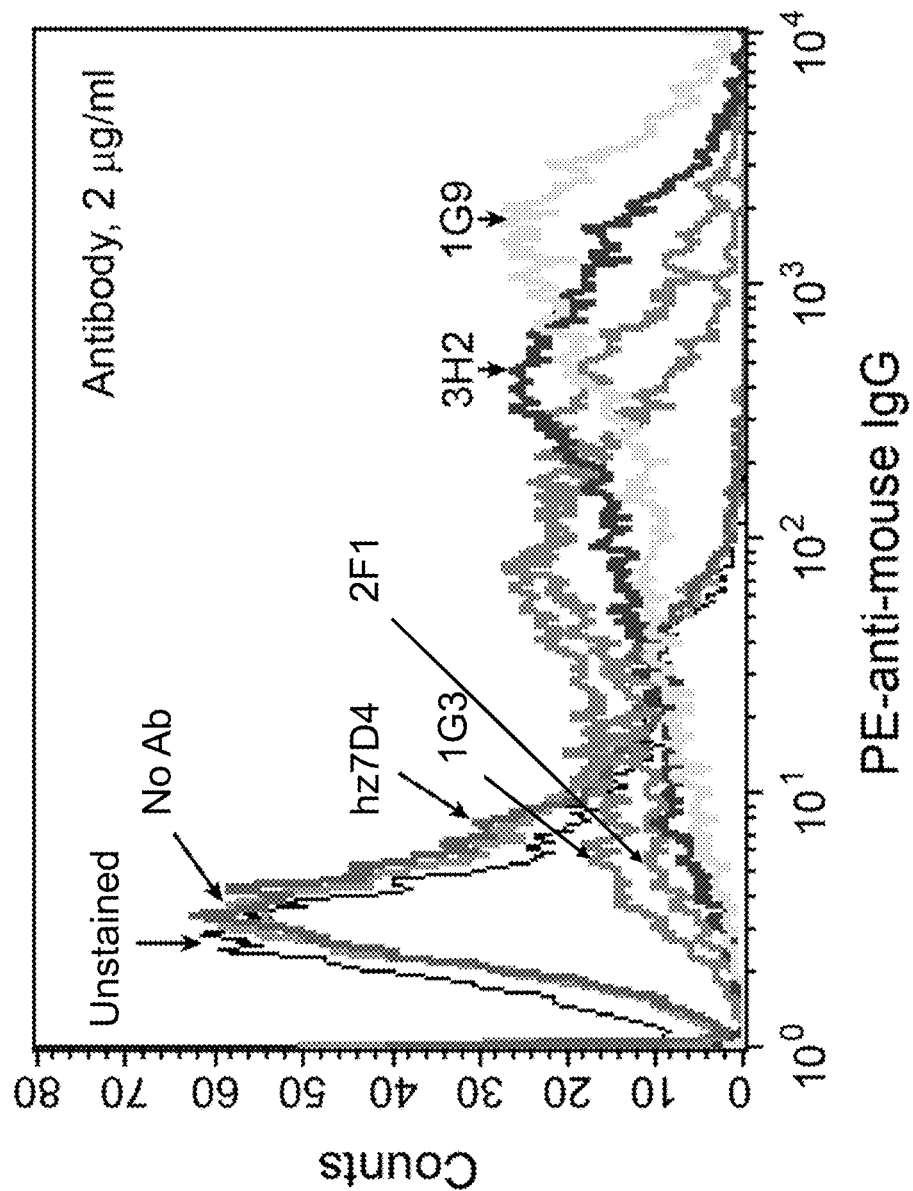
FIG. 11 shows a flow cytometry plot showing the binding of different anti-TIGIT antibodies to mouse TIGIT-expressing CHO cells (mTIGIT/CHO).

FIG. 11 shows a flow cytometry plot showing the binding of mTIGIT/CHO cells by different anti-TIGIT antibodies. Cell binding levels were consistent with the ELISA binding data shown in Table 7.

Example 16: Anti-Tumor Efficacy in a Syngeneic Colon Carcinoma Tumor Model

For syngeneic tumor model experiments, 6- to 8-week-old BALB/c mice were subcutaneously (s.c.) injected with $2\times10^5$ cells of CT26 colon cancer cells (ATCC, CRL-2638). When tumors reached an average of ~80 mm$^3$, mice were grouped (n=9) and treated with 200 µg of antibodies (1G9, 2F1, and 3H2) or PBS control by intraperitoneal (i.p.) injection twice weekly for 3 weeks. Tumor growth was monitored, and tumor volumes were measured.

Figure 12A:
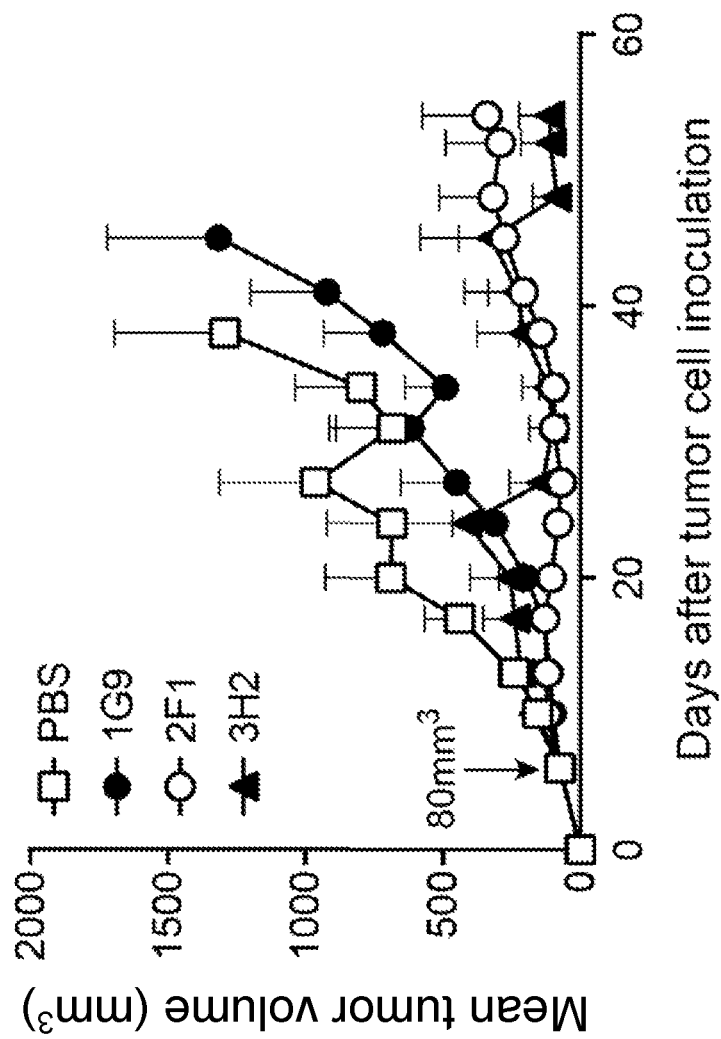
FIG. 12A-12B show CT26 tumor cell growth curves for mice treated with anti-TIGIT antibodies in monotherapy. The tumor size (mean±SE) (FIG. 12A) and individual tumor growth curves (FIG. 12B) were plotted for each treatment group. Mice were sacrificed when tumor volume exceeded 2,000 mm$^3$.
Figure 12B:
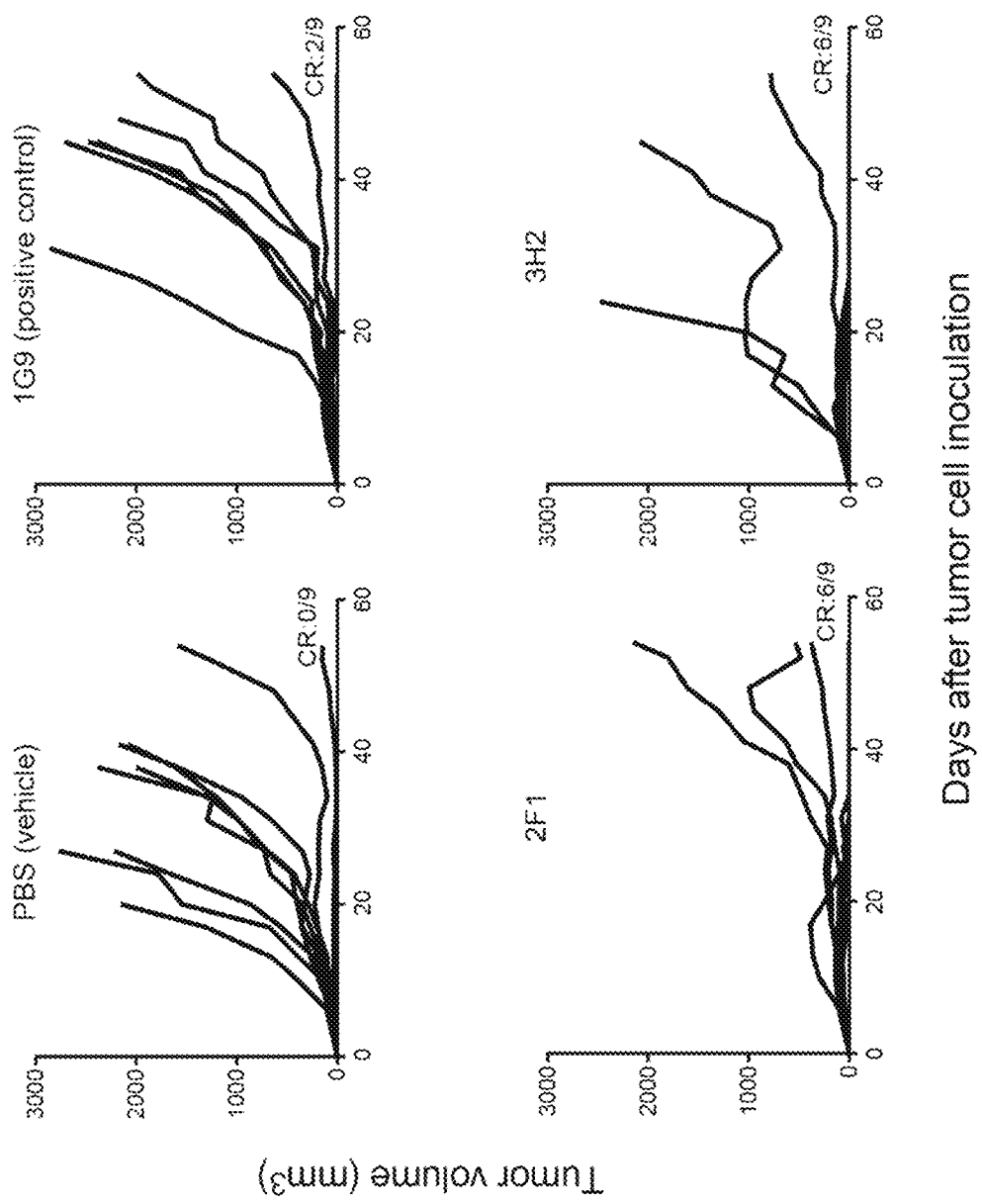

The results are shown in FIG. 12A-12B. hz7D4-derived, mouse affinity-matured 2F1 and 3H2 mIgG2a-DLE antibodies inhibited CT26 tumor growth in BALB/c mice. Tumor growth delay was observed in groups treated with 2F1 and 3H2. Six out of 9 mice treated with both the 2F1 and 3H2 antibodies had a complete response for up to 120 days (clinical endpoint).

Example 17: Affinity Maturation of hz7D4 Against Human and Cyno Monkey TIGIT

For affinity maturation of hz7D4 scFv against human and cyno TIGIT, phages ($10^9$ cfu) from the heavy and light chain CDR3 libraries were incubated separately with 0.1 nM of biotinylated human TIGIT IgV domain in 1 ml PBS/0.1% Tween-20 containing 3% non-fat milk for 1 hour at room temperature. The phages were captured by incubation with 50 µl of M280 streptavidin magnetic beads (Thermo Fisher Scientific) for 15 min. Non-specific phages were eliminated by ten washes with PBS/0.1% Tween-20, followed by 10 washes with PBS for 5 min each. Bound phages were eluted with 0.1 M glycine (pH 2.0), neutralized with 1 M Tris-HCl (pH 8.0) and re-infected into log-phase TG1 cells. In the second panning round, phages ($10^9$ cfu) were used against 0.1 nM of the biotinylated cyno TIGIT IgV domain.

The nucleotide sequences of the phage clones that bind to both human and cyno TIGIT IgV domains were determined. All heavy chain CDR3 (HCDR3) clones contain the wild type HCDR3 amino acid sequence of LGRGYWYFDV (SEQ ID NO: 3). Two light chain CDR3 (LCDR3) clones screened by the light chain library, designated 1A11 and 1E3, contain LCDR3 amino acid sequences of QLFRSGSA (SEQ ID NO: 23) and STFTVINL (SEQ ID NO: 24), respectively.

Selected scFv clones 1A11 and 1E3, with different amino acid sequences in the LCDR3 region, were converted into human IgG1 isotype with DLE mutations at the Fc region (hIgG1-DLE) in order to enhance ADCC effector function. The two recombinant antibodies, 1A11 hIgG1-DLE and 1E3 hIgG1-DLE, were expressed in CHO-S cells and purified by Protein A (MabSelect SuRe) columns. Amino acid sequences of the humanized 1A11 hIgG1-DLE and 1E3 hIgG1-DLE antibodies are listed in Tables 2-5.

Example 18: Binding of Anti-TIGIT Antibodies to CHO Cells Expressing Cyno TIGIT

Figure 13:
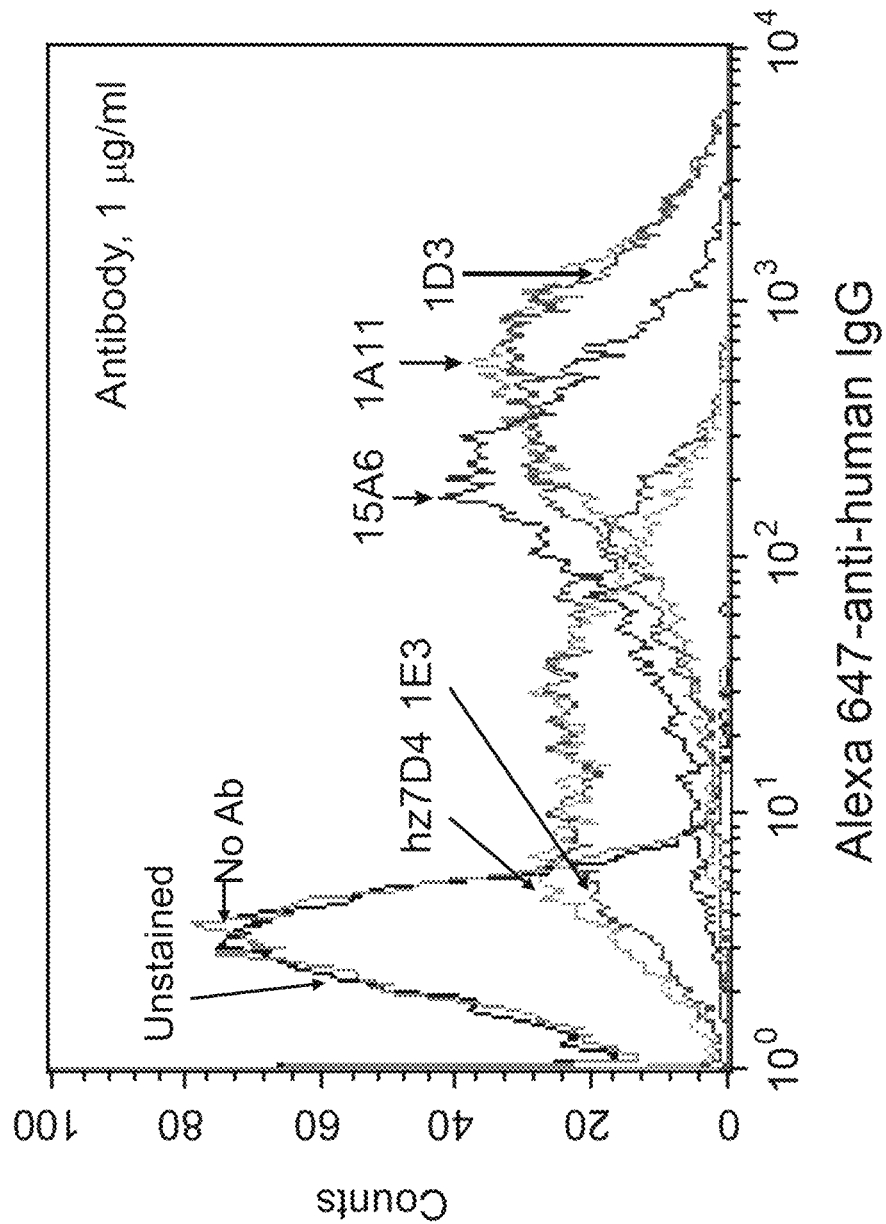
FIG. 13 shows a flow cytometric plot showing the binding of anti-TIGIT antibodies hz7D4, 1E3, 1A11, 15A6 and 1D3 to cyno TIGIT-expressing CHO cells (cynoTIGIT/CHO) at an antibody concentration of 1 μg/ml.

Anti-TIGIT antibodies, including hz7D4 hIgG1, 1A11 hIgG1-DLE, 1E3 hIgG1-DLE, and reference antibodies (15A6 hIgG1 and 1D3 hIgG1) were separately incubated with $5\times10^5$ of CHO cells expressing cyno TIGIT (cyno-TIGIT/CHO) in 50 µl of FACS buffer (0.2% BSA in Dulbecco's phosphate-buffered saline (DPBS) containing 0.09% sodium azide) at a final concentration of 1 µg/ml on ice for 1 hour. After washing, the cells were stained with anti-human IgG conjugated with Alexa-647 dyes and antibody binding strength was analyzed by flow cytometry. The results are shown in FIG. 13.

Example 19: Antibody-Dependent Cell-Mediated Cytotoxicity Function of hz7D4 hIgG1, 1A11 hIgG1-DLE, and 1E3 hIgG1-DLE The T lymphoma cell line MJ[G11] (ATCC, CRL-8294) was used to evaluate antibody-dependent cell-mediated cytotoxicity (ADCC) by the FcRyIIIa (F176V)-expressing human NK92 cell line (ATCC, PTA-6967), in the presence of different anti-TIGIT antibodies, including hz7D4 hIgG1, 1A11 hIgG1-DLE, and 1E3 hIgG1-DLE, and reference antibodies (15A6 hIgG1 and 1D3 hIgG1). MJ[G11] cell membranes were first stained with 10 µM of calcein AM fluorescent dye and then incubated at 37° C. for 30 min. The cells were washed three times with culture medium. The cell number was counted by trypan blue and cell density was adjusted to $2\times10^5$ cells/mi. A sequential dilution of different anti-TIGIT antibodies was added into a 96-well V-bottom microtiter plate at a volume of 20 µl for each concentration, ranging from $10^{-5}$ to 10 µg/ml. NK92 cells were washed and adjusted to $1.6\times10^5$ cells/ml of culture medium. 50 µl each of 8,000 of NK92 (effector cells, E) and 10,000 MJ[G11] (target cells, T) cells were added into the same wells to make an E:T ratio=0.8:1. The plate was then incubated for 4 hours at 37° C. The plate was centrifuged at 500×g for 5 min to pellet down the cells. 100 µl of the supernatant from each sample well were then transferred into a 96-well black microtiter plate, and the fluorescence (excitation: 488 nm, emission: 518 nm) was analyzed by a plate reader. The fluorescence intensity of the target cell without antibody was used as target cell spontaneous release. Addition of 20 µl of 1% Triton X-100 to achieve complete lysis of the target cells was used as maximum release. The percentage of lysis of the target cells by NK92 cells in the presence of treated antibodies was calculated on the basis of fluorescence intensity by the following equation:

$$\% \text{ Lysis} = \frac{\text{Experimental release} - \text{Target cell spontaneous release}}{\text{Maximum release} - \text{Target cell spontaneous release}} \times 100\%$$

Figure 14:
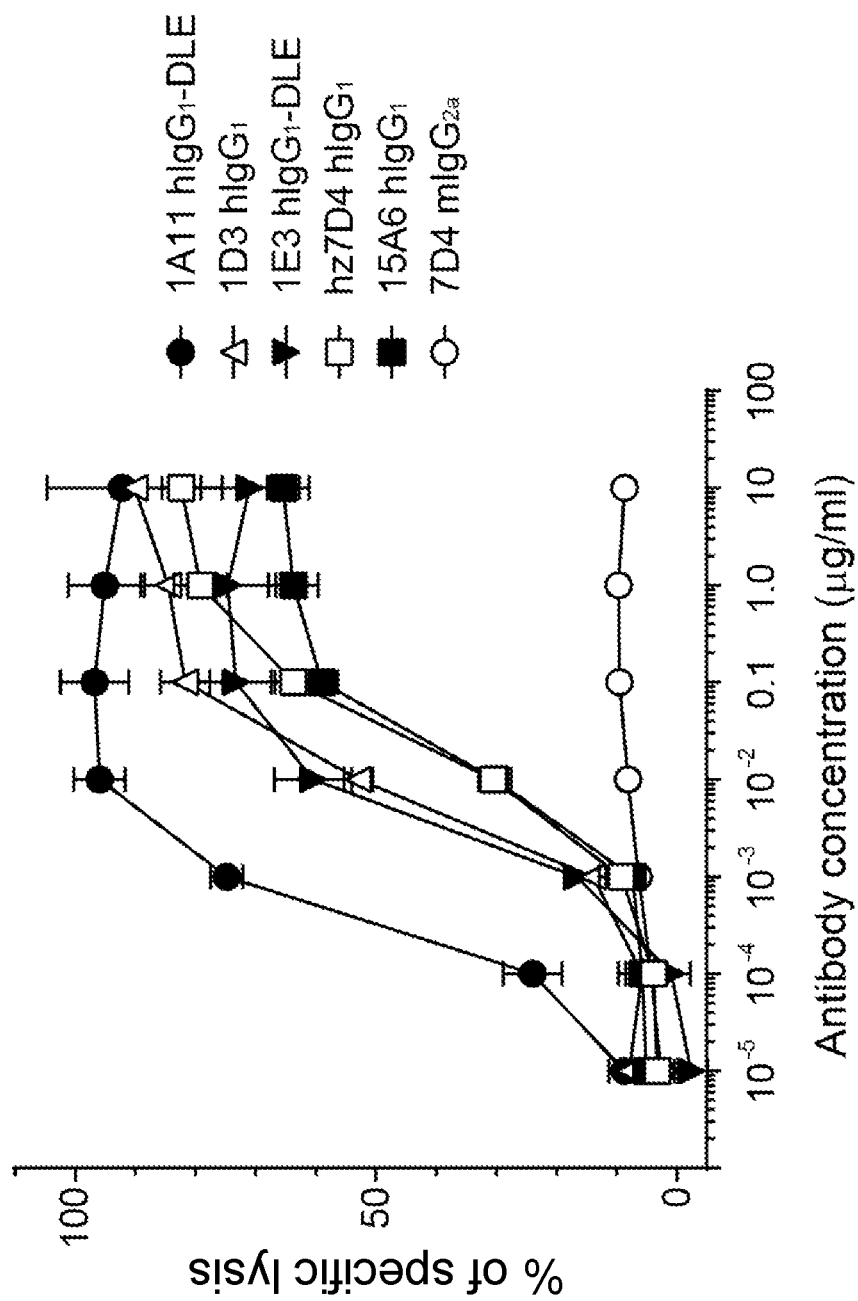
FIG. 14 shows a graph showing antibody-dependent cell-mediated cytotoxicity (ADCC) activity of different anti-TIGIT antibodies, including parental antibody hz7D4 hIgG1, Fc-engineered hz7D4 variants 1A11 and 1E3 hIgG1-DLE, and reference antibodies 15A6 hIgG1 and 1D3 hIgG1. NK cells and calcein AM-stained MJ[G11] cells were co-cultured with different concentrations of the antibodies for 4 hours. The mouse IgG2a isotype of 7D4 (7D4 mIgG2a) was used as a negative control.

The results are shown in FIG. 14. Both of the Fc-engineered variant of 1A11 and 1E3 (hIgG1-DLE) enhanced antibody-dependent cell-mediated cytotoxicity (ADCC) by human natural killer cells to kill TIGIT-expressing MJ[G11] cells, with 1A11 hIgG1-DLE exhibiting the strongest ADCC activity of the tested antibodies. 7D4 mIgG2a in the control group, with its lack of human Fc, exhibited a basal level of ADCC activity (i.e., the level of the co-cultured effector and target cells without any antibodies).

Example 20: Epitope Mapping of 7D4 and the Humanized 7D4 Variant, 1A11

Figure 15A:
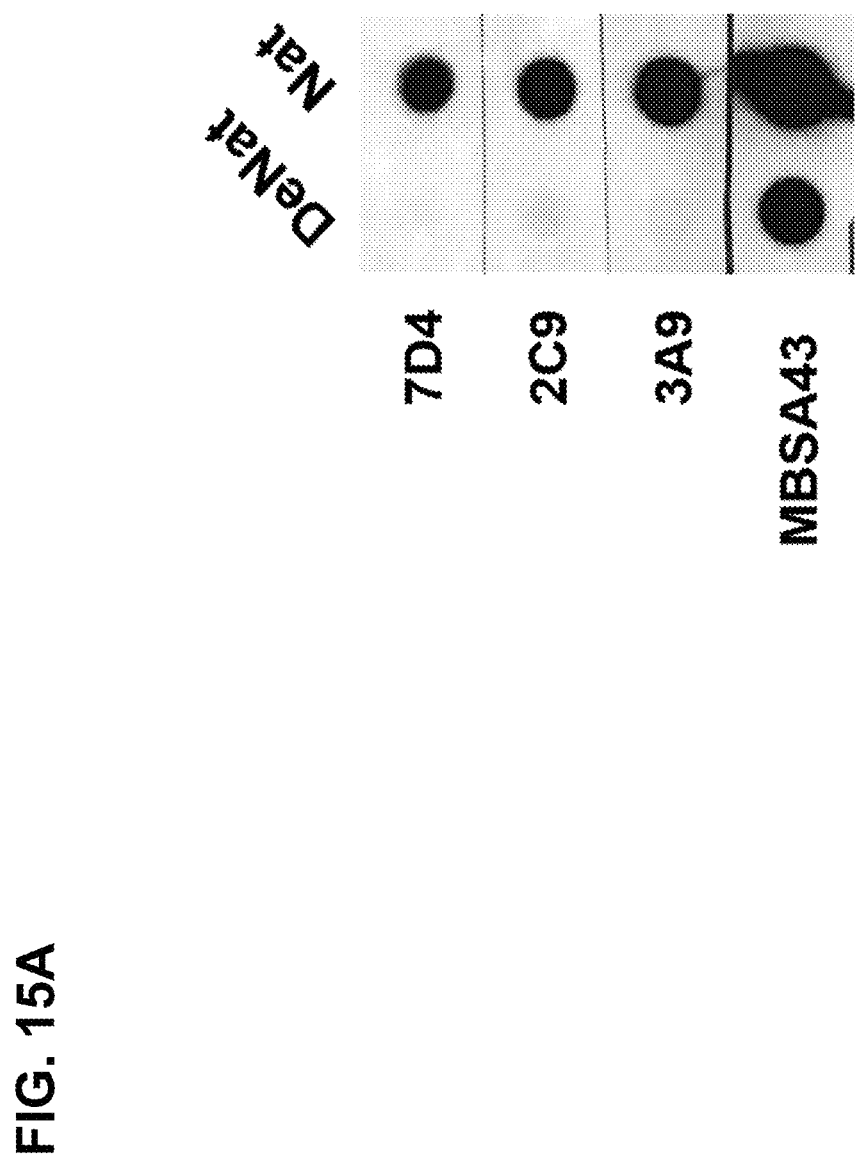
FIG. 15A-15B show the results from epitope binding analyses.

To determine whether the selected anti-TIGIT antibodies recognize a continuous (linear) or discontinuous (conformational) epitope of human TIGIT, 0.1 µg of the recombinant human TIGIT IgV protein, with or without denaturation with SDS and reducing agent, was transferred onto a nitrocellulose membrane directly using a dot blot transferring apparatus. After blocking and washing steps, the membrane strips were immunoblotted with 7D4, 2C9, 3A9, and MBSA43 antibodies and detected by anti-mouse Fcγ-HRP, separately. The results are shown in FIG. 15A. Anti-TIGIT monoclonal antibodies, 7D4, 2C9, and 3A9, only bound to native form human TIGIT protein, indicating that they recognize TIGIT conformational epitopes. In contrast, antibody MBSA43 bound to both native and denatured TIGIT, indicating that it recognizes a TIGIT linear epitope.

Figure 15B:
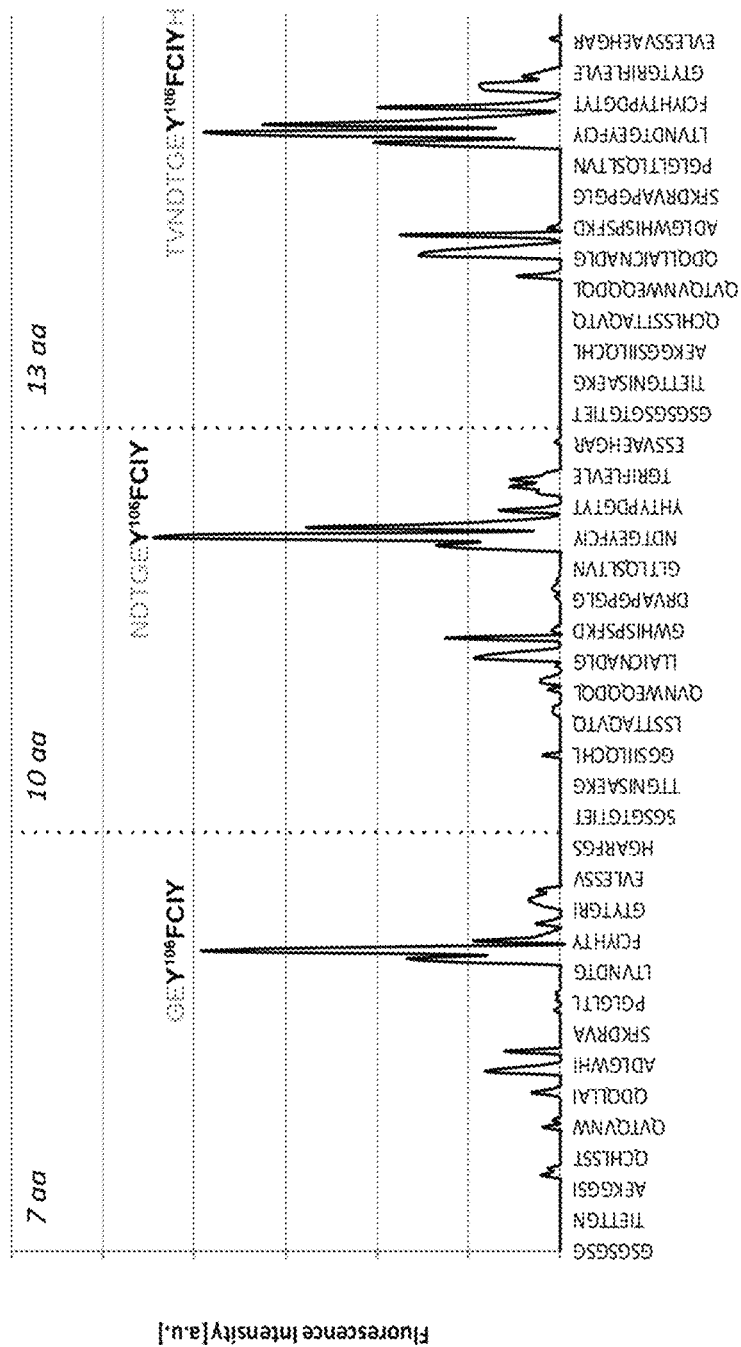

PEPperMAP Conformational Epitope Mapping was used to identify the binding regions of human TIGIT (SEQ ID NO: 22) by recombinant 7D4 antibody (in mouse IgG2a isotype). A peptide synthesizer was used to synthesize cyclic peptides covering the entire TIGIT IgV domain (SEQ ID NO: 22, underline) with a loop peptide length of 7, 10, or 13 amino acid residues on a microchip. The overlapping peptide sequences for each spot differed by one amino acid residue. Next, the microchip was hybridized with recombinant 7D4 antibody. After washing, spot intensities were quantified by anti-mouse IgG conjugated with Dylight 680. As shown in FIG. 15B, 7D4 showed the strongest binding signals with 7, 10, and 13 amino acid cyclic peptides containing a consensus motif, YFCIY (SEQ ID NO: 52).

```
Human TIGIT (IgV domain underlined)
                                    (SEQ ID NO: 22)
MRWCLLLIWAQGLRQAPLASGMMTGTIETTGNISAEKGGSIILQCHL

SSTTAQVTQVNWEQQDQLLAICNADLGWHISPSFKDRVAPGPGLGLT

LQSLTVNDAGEYFCIYHTYPDGTYTGRIFLEVLESSVAEHGARFQIP

LLGAMAATLVVICTAVIVVVALTRKKKALRIHSVEGDLRRKSAGQEE

WSPSAPSPPGSCVQAEAAPAGLCGEQRGEDCAELHDYFNVLSYRSLG

NCSFFTETG
```

To further identity the amino acid residues of TIGIT that interact with the recombinant 7D4 mIgG2a antibody, single alanine substitution mutants were generated in the human TIGIT IgV domain by site-directed mutagenesis using standard molecular techniques. ELISA binding assays were then performed to assess 7D4 binding strength.

Figure 16:
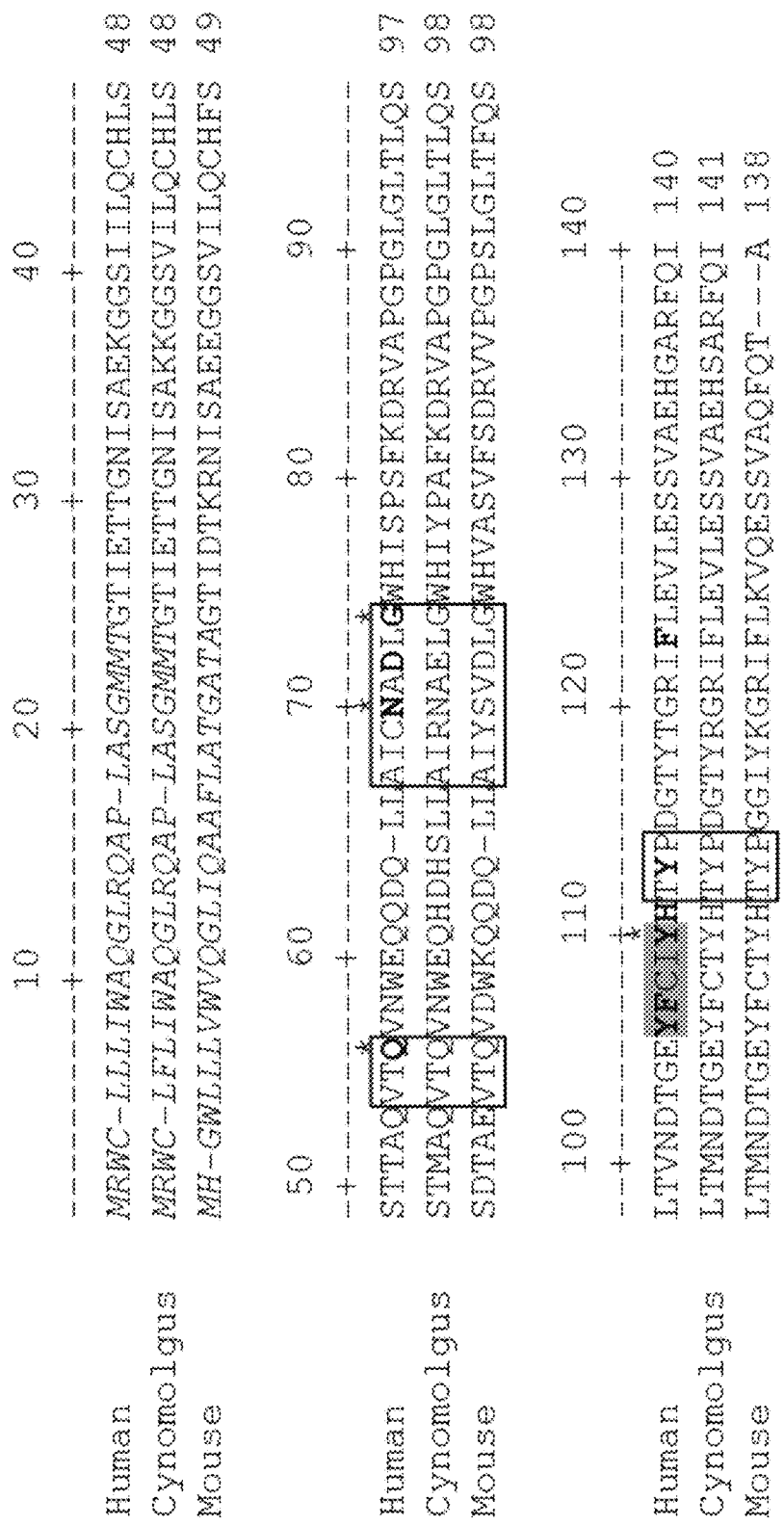
FIG. 16 shows an amino acid sequence alignment of human, cynomolgus monkey, and mouse TIGIT IgV domains containing signal peptides (shown in italics). The conserved (V/I)(S/T)Q, AX6G, and T(F/Y)P motifs located at the interface of TIGIT/PVR are boxed. The amino acid residues of Q56, N70, G74, and Y110 are indicated by asterisk (*). The conserved 7D4 binding peptide loop, YFCIY (SEQ ID NO: 52), is highlighted in gray box. The individual amino acid residues that were mutated into alanine for evaluating TIGIT/7D4 binding are indicated in boldface.

FIG. 16 shows an amino acid sequence alignment of human, cynomolgus monkey, and mouse TIGIT IgV domains. The individual amino acid residues that were mutated into alanine for studying the TIGIT/7D4 bindings are indicated in boldface. For 7D4 epitope mapping, the following 10 mutants were used for ELISA binding assays: Q56A, N70A, D72A, G74A, Y106A, F107A, Y110A, H111, Y113A, and F123A. Amino acid residues of Q56, N70, D72, G74, and Y113 are near the interface of the TIGIT/CD155 complex (Stengel et al. (2012) Proc. Natl. Acad. Sci. USA 109:5399-5404), whereas Y106, F107 and Y110 are located at the parental mouse 7D4 antibody binding consensus motif, YFCIY (SEQ ID NO: 52), in TIGIT. Based on the fluorescence signal intensities of the microarray data shown in FIG. 15B, recombinant TIGIT IgV point substitution mutants were produced in Expi293F cells (Thermo Fisher Scientific, #A14527) following the manufacturer's protocol and were purified separately from culture supernatant by Strep-Tactin XT Superflow chromatography (IBA Technology, Inc.).

Figure 17:
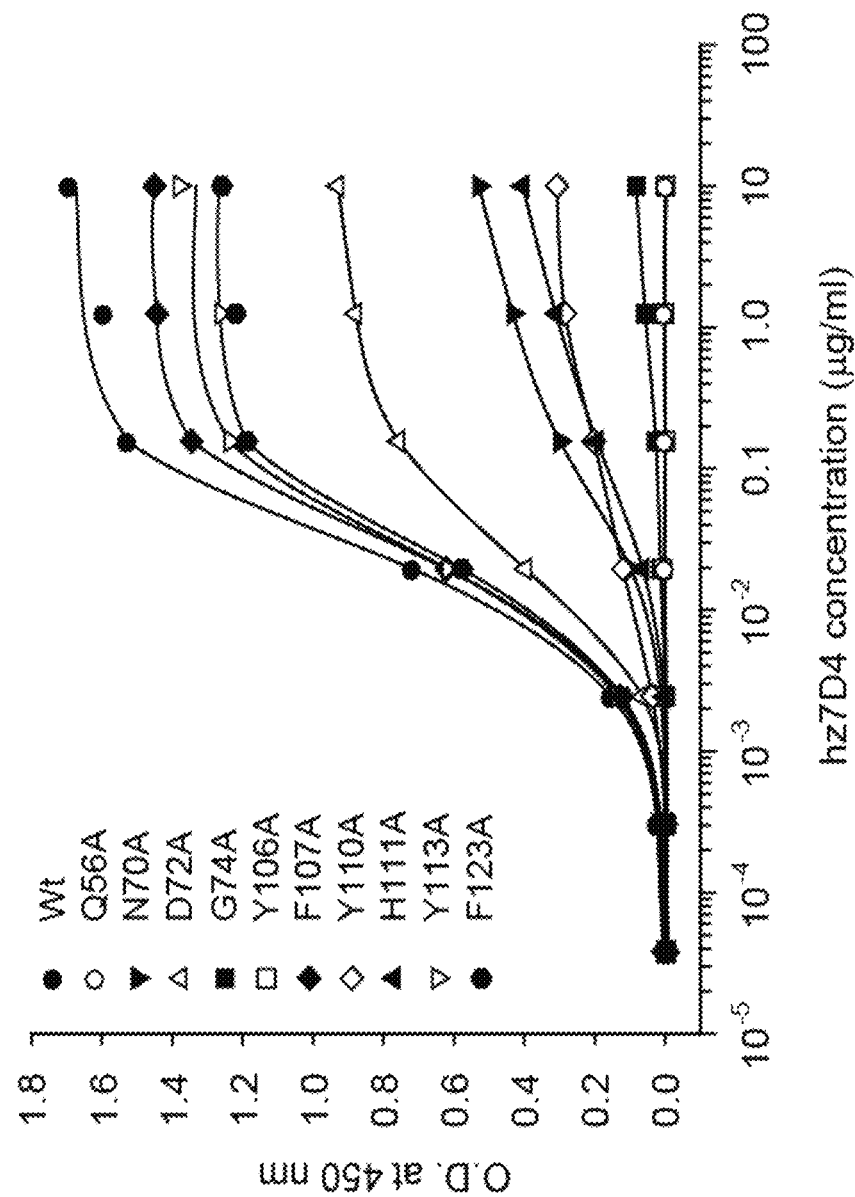
FIG. 17 shows an ELISA binding analysis of 7D4 against different point mutations of the human TIGIT IgV domain.
Figure 18:
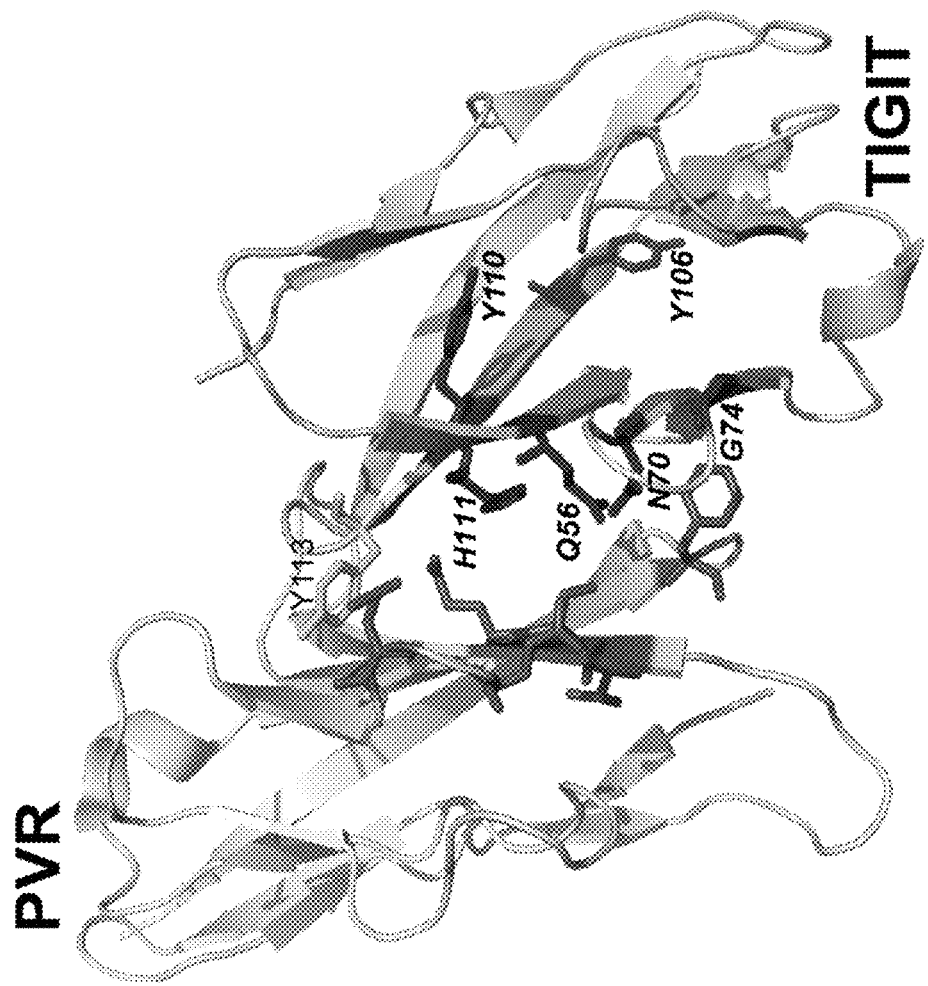
FIG. 18 shows a ribbon diagram showing the interaction of the human TIGIT/PVR (CD155) complex. Amino acid residues Q56, N70, G74, and Y113 of TIGIT are located at the interface of TIGIT/PVR. Amino acid residues Q56, N70, G74, Y106, Y110, and H111, which are involved in 1A11 binding as identified by ELISA binding assays of the point mutations of the human TIGIT IgV domain, are indicated by numbers in bold italics. The amino acid residue Y106 is located at a p-sheet structure facing out of the TIGIT/PVR interface.

FIG. 17 shows the ELISA binding results of 7D4 to TIGIT mutants. Q56 and Y106 single alanine substitution mutants completely abolished the binding of 7D4. G74, and Y110, and H111 single alanine substitution mutants showed a significant reduction in 7D4 binding (more than 50% of the wild type) at a concentration up to 10 µg/ml. These data demonstrate that three amino acid residues, Y106, Y110, and H111, located at a p-sheet facing out of the TIGIT/PVR interface, are involved in hz7D4 binding to TIGIT. FIG. 18 shows a molecular structure model for analyzing the co-crystallization of human PVR (CD155) and TIGIT according to Stengel et al. ((2012) Proc Natl Acad Sci USA 109: 5399-5404).

Figure 19:
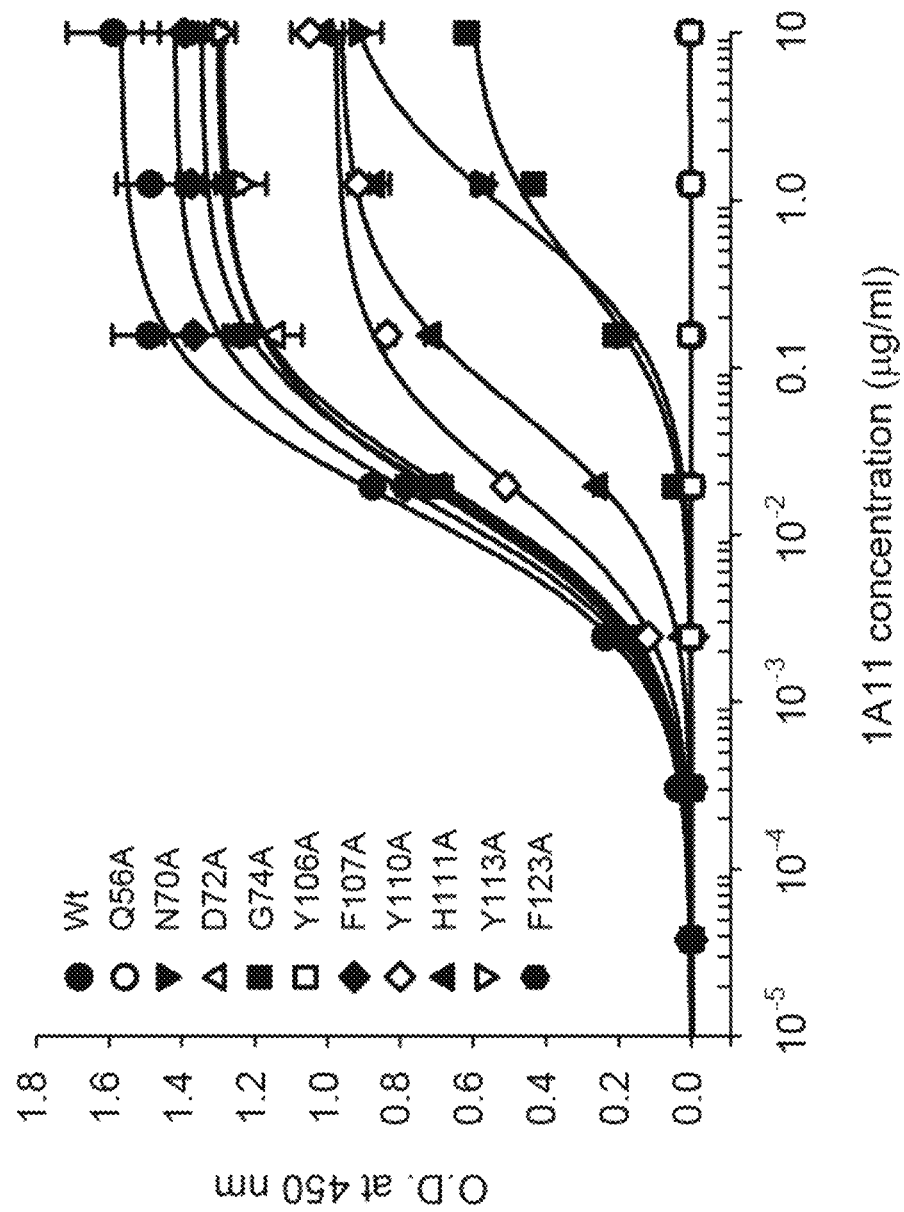
FIG. 19 shows an ELISA binding analysis of 1A11 against different point mutations of the human TIGIT IgV domain.

To identify the amino acid residues of TIGIT that interact with the humanized 7D4 variant, 1A11 (in human IgG1-DLE isotype), ELISA binding assays with the single alanine substitution mutants were performed to assess 1A11 binding strength. FIG. 19 shows the ELISA binding results of 1A11 to various TIGIT mutants. Similar to the parental mouse 7D4 antibody, Q56 and Y106 single alanine substitution mutants completely abolished the binding of 1A11, G74, Y110, and H111 single alanine substitution mutants showed a significant reduction in 1A11 binding (more than 40% of the wild type) at a concentration up to 10 µg/ml.

The invention claimed is:

1. An isolated antibody or antigen-binding fragment that specifically binds to human T cell immunoglobulin and ITIM domain (TIGIT), wherein the antibody or antigen-binding fragment comprises:

(a) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3);
(b) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 24 (LCDR3);
(c) three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);
(d) three heavy chain complementarity determining regions (HCDRs) comprising amino acid sequences of SEQ ID NO: 1 (HCDR1), SEQ ID NO: 2 (HCDR2), and SEQ ID NO: 19 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);
(e) three heavy chain complementarity determining regions (HCDRs) comprising amino acid sequences of SEQ ID NO: 1 (HCDR1), SEQ ID NO: 2 (HCDR2), and SEQ ID NO: 20 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);
(f) three heavy chain complementarity determining regions (HCDRs) comprising amino acid sequences of SEQ ID NO: 1 (HCDR1), SEQ ID NO: 2 (HCDR2), and SEQ ID NO: 21 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3);
(g) three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3); or
(h) three heavy chain complementarity determining regions (HCDRs) comprising amino acid sequences of SEQ ID NO: 13 (HCDR1), SEQ ID NO: 14 (HCDR2), and SEQ ID NO: 15 (HCDR3); and three light chain complementarity determining regions (LCDRs) comprising amino acid sequences of SEQ ID NO: 16 (LCDR1), SEQ ID NO: 17 (LCDR2), and SEQ ID NO: 18 (LCDR3).

2. The antibody or antigen-binding fragment of claim 1, wherein the antibody or antigen-binding fragment comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 23 (LCDR3).

3. The antibody or antigen-binding fragment of claim 1, wherein the antibody or antigen-binding fragment comprises human germline heavy and light chain framework regions, or human germline heavy and light chain framework regions mutated to comprise one or more amino acid substitutions.

4. The antibody or antigen-binding fragment of claim 1, wherein the antibody or antigen-binding fragment comprises a heavy chain variable region that is at least 90% identical to an amino acid sequence of SEQ ID NO: 39, and a light chain variable region that is at least 90% identical to an amino acid sequence of SEQ ID NO: 40.

5. The antibody or antigen-binding fragment of claim 1, wherein the antibody or antigen-binding fragment comprises a heavy chain variable region comprising an amino acid sequence of SEQ ID NO: 39, and a light chain variable region comprising an amino acid sequence of SEQ ID NO: 40.

6. The antibody or antigen-binding fragment of claim 1, wherein the antibody or antigen-binding fragment comprises a human IgG1 heavy chain constant region, or a human IgG1 heavy chain constant region mutated to modify effector function.

7. The antibody or antigen-binding fragment of claim 1, wherein the antibody or antigen-binding fragment comprises a heavy chain constant region comprising an amino acid sequence of SEQ ID NO: 43, or a heavy chain constant region comprising an amino acid sequence of SEQ ID NO: 43 mutated to comprise amino acid substitutions at positions 239, 330, and 332.

8. The antibody or antigen-binding fragment of claim 7, wherein:
the S at position 239 of SEQ ID NO: 43 is substituted with D;
the A at position 330 of SEQ ID NO: 43 is substituted with L; and
the I at position 332 of SEQ ID NO: 43 is substituted with E.

9. The antibody or antigen-binding fragment of claim 1, wherein the antibody or antigen-binding fragment comprises a heavy chain constant region comprising an amino acid sequence of SEQ ID NO: 44.

10. The antibody or antigen-binding fragment of claim 1, wherein the antibody or antigen-binding fragment comprises a human Ig kappa light chain constant region.

11. The antibody or antigen-binding fragment of claim 1, wherein the antibody or antigen-binding fragment comprises a light chain constant region comprising an amino acid sequence of SEQ ID NO: 45.

12. The antibody or antigen-binding fragment of claim 1, wherein the antibody or antigen-binding fragment comprises a heavy chain constant region comprising an amino acid sequence of SEQ ID NO: 44, and a light chain constant region comprising an amino acid sequence of SEQ ID NO: 45; and/or wherein the antibody or antigen-binding fragment comprises a heavy chain comprising an amino acid sequence of SEQ ID NO: 47, and a light chain comprising an amino acid sequence of SEQ ID NO: 48.

13. The antibody or antigen-binding fragment of claim 12, wherein the heavy chain constant region or heavy chain further comprises a C-terminal lysine (K).

14. A pharmaceutical composition comprising the antibody or antigen-binding fragment of claim 1 and a pharmaceutically acceptable carrier.

15. A method of activating and/or killing one or more immune cells in a subject in need thereof, comprising administering to the subject an effective amount of the antibody or antigen-binding fragment of claim 1.

16. The method of claim 15, wherein activating one or more immune cells comprises activating one or more natural killer cells, one or more cytotoxic T cells, one or more helper T cells, and/or one or more monocyte cells.

17. The method of claim 15, wherein killing one or more immune cells comprises killing one or more regulatory T cells.

18. The method of claim 15, wherein the antibody or antigen-binding fragment or pharmaceutical composition is administered in combination with at least one additional therapeutic agent.

19. The method of claim 18, wherein the at least one additional therapeutic agent comprises a checkpoint inhibitor.

20. A method of treating a cancer in a subject in need thereof, comprising administering to the subject a therapeutically effective amount of the antibody or antigen-binding fragment of claim 1.

21. The method of claim 20, wherein the cancer expresses CD155.

22. The method of claim 20, wherein the cancer is a colorectal cancer or leukemia.

23. The method of claim 20, wherein the antibody or antigen-binding fragment or pharmaceutical composition is administered in combination with at least one additional therapeutic agent.

24. The method of claim 23, wherein the at least one additional therapeutic agent comprises a checkpoint inhibitor.

25. A method of treating an infection or infectious disease in a subject in need thereof, comprising administering to the subject a therapeutically effective amount of the antibody or antigen-binding fragment of claim 1.

26. The method of claim 25, wherein the infection or infectious disease is a human T cell leukemia virus type 1-associated disease.

27. The method of claim 25, wherein the antibody or antigen-binding fragment or pharmaceutical composition is administered in combination with at least one additional therapeutic agent.

28. The method of claim 27, wherein the at least one additional therapeutic agent comprises a checkpoint inhibitor.

29. An isolated nucleic acid encoding the antibody or antigen-binding fragment of claim 1.

30. An isolated vector comprising the nucleic acid of claim 29.

31. An isolated cell or cell population comprising the nucleic acid of claim 29.

32. A method of producing an antibody or antigen-binding fragment, comprising culturing the cell or cell population of claim 31 under conditions suitable to produce the antibody or antigen-binding fragment.

33. The method of claim 32, further comprising isolating, purifying, and/or recovering the produced antibody or antigen-binding fragment.

\* \* \* \* \*